(12) United States Patent
Breslav et al.

(10) Patent No.: US 7,205,384 B2
(45) Date of Patent: Apr. 17, 2007

(54) PROCESS FOR PREPARING PEPTIDYL HETEROCYCLIC KETONE DERIVATIVES

(75) Inventors: Michael Breslav, Maple Glen, PA (US); Bruce Harris, Lansdowne, PA (US); Birdella Kenney, North Wales, PA (US); Thomas Maier, Stockach (DE); Armin Roessler, Tengen (DE); Frank Villani, Perkasie, PA (US); Ulrich Weigl, Hilzingen (DE); Fan Zhang-Plasket, Willow Grove, PA (US); Hua Zhong, Maple Glen, PA (US)

(73) Assignee: Ortho-McNeil Pharmaceutical Inc., Raritan, NJ (US)

( * ) Notice: Subject to any disclaimer, the term of this patent is extended or adjusted under 35 U.S.C. 154(b) by 0 days.

(21) Appl. No.: 10/902,755

(22) Filed: Jul. 29, 2004

(65) Prior Publication Data

US 2005/0059607 A1    Mar. 17, 2005

Related U.S. Application Data

(60) Provisional application No. 60/566,374, filed on Apr. 29, 2004, provisional application No. 60/492,646, filed on Aug. 5, 2003.

(51) Int. Cl.
*A61K 38/00* (2006.01)
(52) U.S. Cl. ................................. 530/333; 530/335
(58) Field of Classification Search ................ 514/19
See application file for complete search history.

(56) References Cited

FOREIGN PATENT DOCUMENTS

| WO | WO 97/48687 A1 | 12/1997 |
|---|---|---|
| WO | WO 00/44733 | * 8/2000 |
| WO | WO 0044733 | 8/2000 |

OTHER PUBLICATIONS

Michael J. Costanzo, et al, "Potent, Small-Molecule Inhibitors of Human Mast Cell Tryptase Antiasthmatic Action of a Dipeptide-Based Transition-State Analogue Containing a Benzothiazole Ketone," J. Med. Chem.; 2003; 46(18) pp. 3865-3876.*
Costano, M.J. et al: "Potent, Small-Molecule Inhibitors of Human Mast Cell Tryptase. Antiasthmatic Action of a Dipeptide-Based Transition-State Analogue Containing a Benzothizaole Ketone", J. Med. Chem. vol. 46, 2003, pp. 3865-3876, XP002314429.
PCT International Search Report, PCT/US2004/025413, Jan. 21, 2005.
Acta Chimica Sinica - Chinese Edition - Huaxue Xuebao, 48 (9), 1990, pp. 931-935.
Bodanszky, Miklos, "Activation and Coupling" Principles of Peptide Synthesis, 1993, pp. 9-61, vol. II, Springer Laboratory, Springer-Verlag, 2nd edition.
T. W. Greene & P.G.M. Wuts, Protective Groups in Organic Synthesis, John Wiley and Sons, 1991.
Protective Groups in Organic Chemistry, Ed. J.F.W. Mcomie, Plenum Press, 1973, pp. 43-93.

\* cited by examiner

*Primary Examiner*—Cecilia J. Tsang
*Assistant Examiner*—Thomas S. Heard

(57) ABSTRACT

The present invention relates to novel processes for the preparation of peptidyl heterocyclic ketones of the general formula (I)

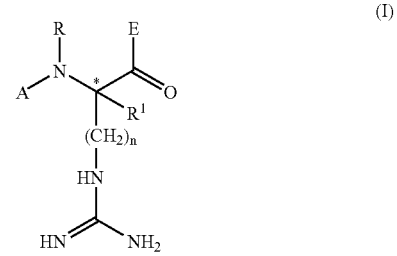

wherein all variables are as herein defined. The present invention further relates to novel pharmaceutical salts and processes for their preparation. The peptidyl heterocyclic ketones of formula (I) are potent and selective inhibitors of tryptase, useful for the treatment and prevention of inflammatory diseases associated with the respiratory tract, such as asthma and allergic rhinitis.

2 Claims, 1 Drawing Sheet

PROCESS FOR PREPARING PEPTIDYL HETEROCYCLIC KETONE DERIVATIVES

CROSS REFERENCE TO RELATED APPLICATIONS

This application claims the benefit of U.S. Provisional Application 60/492,646, filed on Aug. 5, 2003, and U.S. provisional Application 60/566,374, filed Apr. 29, 2004, which is incorporated by reference herein in its entirety.

BACKGROUND OF THE INVENTION

Field of the Invention

The present invention relates to a novel process for the preparation of peptidyl heterocyclic ketone derivatives of the general formula (I)

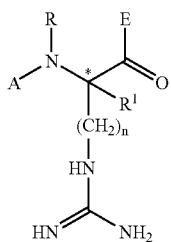

wherein A, R, R$^1$, E and n are as herein defined.

The present invention is further directed to pharmaceutically acceptable salts of the compound of formula (IIa)

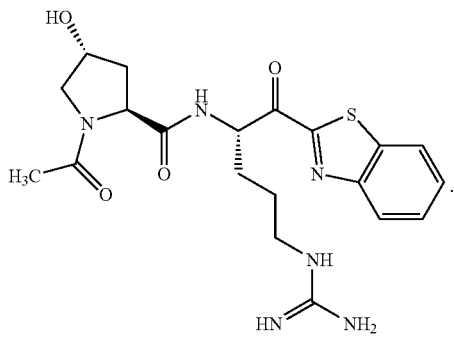

The present invention is further directed to processes for the preparation of the compound of formula (IIa) and its pharmaceutically acceptable salts thereof.

The peptidyl heterocyclic ketone derivatives of formula (I) are potent and selective inhibitors of tryptase, useful for the treatment and prevention of inflammatory diseases associated with the respiratory tract, such as asthma and allergic rhinitis, as well as other immunomediated inflammatory disorders such as rheumatoid arthritis, conjunctivitis, psoriasis, inflammatory bowel disease, various vascular and dermatological conditions.

Costanzo et al in PCT publication WO 00/44733 disclose a process for the preparation of compounds of formula (I). However, the process disclosed in the PCT application requires three chromatographic separations, (one in reverse phase), the use of explosive and toxic reagents (in the Dess-Martin oxidation step and HF de-protection), use of cryogenic (−78° C.) temperatures, non-crystalline intermediates, and a product stream that is a mixture of diastereomers requiring separation, which make it unsuitable for large scale manufacture. Thus there exists a need for a process for the preparation of compounds of formula (I) which meets large scale production/manufacturing restrictions.

Berryman et al., in PCT publication WO97/48687 disclose a process for the preparation of chiral keto-heterocycles of basic amino acids.

We now describe a novel process for the preparation of compounds of formula (I) suitable for large scale synthesis. More particularly, the process of the present invention avoids toxic and/or explosive materials, does not require cryogenic temperatures, and/or does not require chromatographic separations. The process of the present invention may also be applied to yield a final product wherein one stereoisomer predominates.

BRIEF SUMMARY OF THE INVENTION

The present invention is directed to a novel process for the preparation of compounds of the general formula (I)

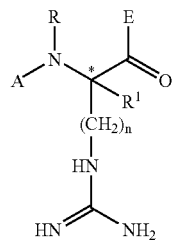

wherein

A is selected from the group consisting of substituted C$_{3-8}$cycloalkylcarbonyl (where the substituents on the C$_{3-8}$cycloalkyl group are independently selected from one or more C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl), substituted norbornanecarbonyl (where the substituents on the norbornane group are independently selected from one or more C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl), substituted norbornenecarbonyl (where the substituents on the norbornene group are independently selected from one or more C$_{1-4}$alkyl, perfluoro C$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl), substituted adamantanecarbonyl (where the substituents on the adamantine group are independently selected from one or more C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl), substituted arylcarbonyl (where the substituents on the aryl group are independently selected from one or more C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl), heteroarylcarbonyl, substituted heteroarylcarbonyl (where the substituents on the heteroaryl are independently selected from one or more C$_{1-4}$alkyl, perfluoro C$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy or C$_{1-4}$alkoxycarbonyl), pyridylcarbonyl, substituted pyridylcarbonyl (where the substituents on the pyridine ring are independently one to three substituents selected from C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl), amidoC$_{1-5}$alkylcarbonyl,

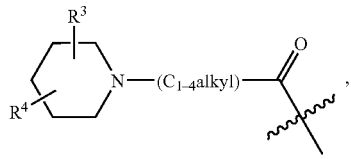

C$_{1-6}$alkyl-C(O)—N(R$^8$)—C$_{0-6}$alkyl-C(O)—,

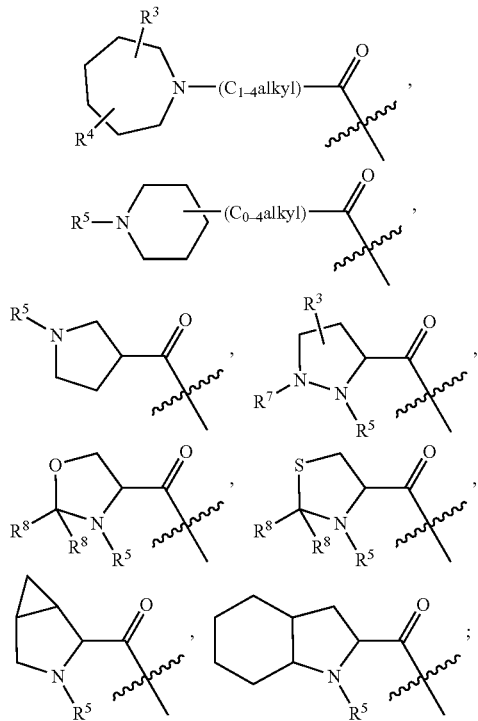

a D or L amino acid which is coupled at its carboxy terminus to the nitrogen depicted in formula (I) and is selected from the group consisting of alanine, glycine, dehydroproline, proline, substituted proline (where the substituents on the proline are independently selected from one or more of C$_{1-4}$alkyl, perfluoroC$_{1-4}$alkyl, C$_{1-4}$alkoxy, hydroxy, oxo, halo, amido, N-C$_{1-4}$alkylamido, N,N—C$_{1-4}$dialkylamido, nitro, amino, C$_{1-4}$alkylamino, C$_{1-4}$dialkylamino, carboxy, C$_{1-4}$alkylcarbonyl, phenylalkyloxy, phenyl or C$_{1-4}$alkoxycarbonyl), pipecolinic acid, substituted pipecolinic acid (where the substituents on the piperidine of the pipecolinic acid group are independently selected from one or more of C$_{1-4}$alkyl, perfluoroC$_{1-4}$alkyl, C$_{1-4}$alkoxy, hydroxy, oxo, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, phenyalkyloxy, phenyl or C$_{1-4}$alkoxycarbonyl), valine, norleucine, leucine, tertluecine, isoleucine, sarocosine, asparagine, serine, methionine, threonine, phenylalanine, 1-naphthalanine, 2-naphthalanine, 2-theintlalanine, 3-thienylalanine, [1,2,3,4]-tetrahydroisoquinoline-1-carboxylic acid and [1,2,3,4]-tetrahydroisoquinoline-2-carboxylic acid, where the amino terminus of said amino acid is connected to a member selected from the group consisting of [1,2,3,4]-tetrahydroisoquinoline-1-carbonyl, [1,2,3,4]-tetrahydroisoquinoline-3-carbonyl, formyl, C$_{1-4}$alkoxycarbonyl, C$_{1-8}$alkylcarbonyl, perfluoro C$_{1-4}$alkylsulfonyl, C$_{1-4}$alkylsulfonyl, amido, N-C$_{1-4}$alkylamido, N,N-C$_{1-4}$dialkylamido, sulfonamido, arylsulfonyl, substituted arylsulfonyl (where the aryl substituents are independently selected from one or more of C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy or C$_{1-4}$alkoxycarbonyl), camphorsulfonyl, C$_{1-4}$alkylsulfinyl, arylsulfinyl, substituted arylsulfinyl (where the aryl substituents are independently selected from one or more of C$_{1-4}$alkyl, perfluoroC$_{1-4}$alkyl, C$_{1-4}$alkoxy, hydroxy, halo, amido, N-C$_{1-4}$alkylamido, N,N-C$_{1-4}$dialkylamido, nitro, amino, C$_{1-4}$alkylamino, C$_{1-4}$dialkylamino, carboxy or C$_{1-4}$alkoxycarbonyl), and arylcarbonyl; or a polypeptide comprised of two amino acids
where the first amino acid is a D or L amino acid, bound via its carboxy terminus to the nitrogen depicted in formula (I) and is selected from the group consisting of proline and substituted proline (where the substituents on the proline are independently selected from one or more C$_{1-4}$alkyl, perfluoroC$_{1-4}$alkyl, C$_{1-4}$alkoxy, hydroxy, oxo, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyl, aralkyloxy, aryl or C$_{1-4}$alkoxycarbonyl), and the second D or L amino acid, is bound to the amino terminus of said first amino acid and is selected from the group consisting of aspartic acid, aspartic acid-4-C$_{1-4}$alkyl ester, glutamic acid, glutamic acid-5-C$_{1-4}$alkyl ester, serine, phenylalanine, substituted phenylalanine (where the phenyl substituents are independently selected from one or more of C$_{1-4}$alkyl, perfluoroC$_{1-4}$alkyl, C$_{1-4}$alkoxy, hydroxy, halo, amido, nitro, amino, N-C$_{1-4}$alkylamino, N,N-C$_{1-4}$dialkylamino, carboxy or C$_{1-4}$alkoxycarbonyl), cyclohexylglycine, and cyclohexlalanine, where the amino terminus of said second amino acid is monosubstituted with a member of the group consisting of C$_{1-6}$alkyl, carboxyC$_{1-8}$alkyl and C$_{1-10}$alkylcarbonyl;

R$^3$ and R$^4$ are each independently selected from the group consisting of hydrogen, C$_{1-4}$alkyl, perfluoroC$_{1-4}$alkyl, C$_{1-4}$alkoxy, hydroxy, oxo, halo, amido, N-C$_{1-4}$alkylamido, N,N-C$_{1-4}$dialkylamido, nitro, amino, C$_{1-4}$alkylamino, C$_{1-4}$dialkylamino, carboxy, C$_{1-4}$alkylcarbonyloxy, C$_{1-4}$alkylcarbonylamino, aryl, substituted aryl (where the substituents on the aryl group are independently selected from one or more of C$_{1-4}$alkyl, perfluoroC$_{1-4}$alkyl, C$_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, $C_{1-4}$alkylcarbonyl, $C_{1-4}$alkylcarbonylamino or $C_{1-4}$alkoxycarbonyl), $C_{1-4}$alkoxycarbonyl, aminosulfonyl, $C_{1-4}$alkylaminosulfonyl, $C_{1-4}$alkylsulfonylamino and N,N-di-$C_{1-4}$alkylaminosulfonyl;

$R^5$ is selected from the group consisting of hydrogen, $C_{1-4}$alkyl and $C_{1-4}$alkylcarbonyl;

$R^7$ is selected from the group consisting of hydrogen, $C_{1-4}$alkyl, $C_{1-4}$alkylcarbonyl and substituted aryl (where the substituents on the aryl group are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkylcarbonyl);

$R^8$ is selected from the group consisting of hydrogen and $C_{1-5}$alkyl;

R is selected from the group consisting of hydrogen and $C_{1-5}$alkyl;

$R^1$ is selected from the group consisting of hydrogen and $C_{1-5}$alkyl;

n is an integer from 2 to 5;

E is an unsubstituted or substituted heterocycle selected from the group consisting of imidazol-2-yl, oxazol-2-yl, thiazol-2-yl, 1,3,4-thiadiazol-2-yl, 1,2,4-thiadiazol-3yl, 1,2,4-thiadiazol-5-yl, isothiazol-3-yl, 1,2,3-triazol-4-yl, 1,2,3-triazol-5-yl, 1,2,4-triazin-3-yl, 1,3,5-triazin-2-yl, isoxazol-3-yl, 1,2,3,4-oxatriazol-5-yl, 1,2,3-oxadiazol-4-yl, 1,3,4-oxadiazol-2-yl, 1,2,4-oxadiazol-3-yl, 1,3,4-oxadiazol-2-yl, pyrazol-3-yl, pyrazin-2-yl, pyrimidin-2-yl, benzoxazol-2-yl, benzimidazol-2-yl, benzothiazol-2-yl, 4,5,6,7-tetrahydrobenzothiazol-2-yl, naphtho[2,1-d]thiazol-2-yl, naphtho[1,2-d]thiadiazol-2-yl, 4-oxoquinazolin-2-yl, quinazolin-2-yl, oxazolo[4,5-b]pyridin-2-yl, oxazolo[5,4-b]pyridin-2-yl, thiazolo[4,5-b]pyridin-2-yl, thiazolo[5,4-b]pyridin-2-yl and thiazolo[5,4-c]pyridin-2-yl, wherein the substituents on the heterocycle are independently selected from $C_{1-4}$alkyl, perfluoro$C_{1-4}$alkyl, $C_{1-4}$alkoxy, hydroxy, halogen, amido, nitro, N-$C_{1-4}$alkylamido, N,N-$C_{1-4}$dialkylamido, amino, $C_{1-4}$alkylamino, $C_{1-4}$dialkylamino, carboxy, $C_{1-4}$alkoxycarbonyl, phenyl$C_{1-4}$alkylaminocarbonyl, aryl or substituted aryl; wherein the substituents on the aryl group are one or more independently selected from the group consisting of $C_{1-4}$alkyl, perfluoro$C_{1-4}$alkyl, $C_{1-4}$alkoxy, halogen, N-$C_{1-4}$alkylamido, N,N-$C_{1-4}$dialkylamido, $C_{1-4}$dialkylamino, carboxy and $C_{1-4}$alkoxycarbonyl;

or a pharmaceutically acceptable salt thereof;

comprising

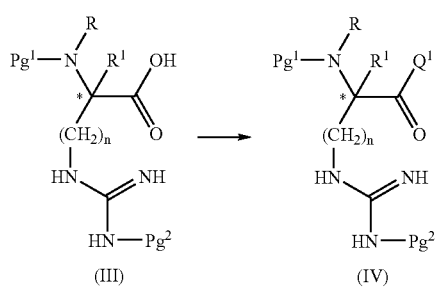

reacting a suitably substituted compound of formula (III), wherein $Pg^1$ is a first nitrogen protecting group and $Pg^2$ is a second nitrogen protecting group; and wherein $Pg^1$ and $Pg^2$ are selected such that the $Pg^1$ protecting group may be removed under conditions which do not remove the $Pg^2$ protecting group; with a suitable activating agent; to yield the corresponding compound of formula (IV), wherein $Q^1$ is a leaving group;

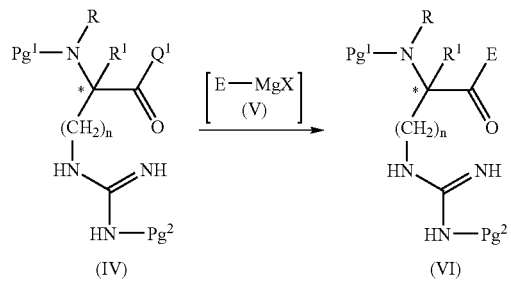

reacting the compound of formula (IV) with a solution or suspension of a suitably substituted compound of formula (V), wherein X is selected from the group consisting of Cl, Br and I; in an anhydrous organic solvent which is inert to the compound of formula (V); to yield the corresponding compound of formula (VI);

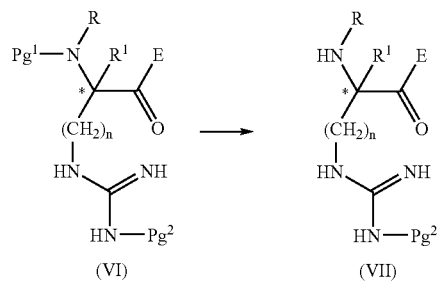

subjecting the compound of formula (VI) to selective de-protection; to yield the corresponding compound of formula (VII) or its corresponding acid addition salt;

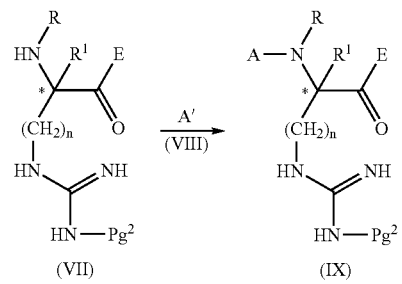

reacting the compound of formula (VII) with a suitably substituted compound of formula (VIII), wherein A' represents an activated form of the A substituent; in the presence of a tertiary amine base; in an aprotic organic solvent; to yield the corresponding compound of formula (IX);

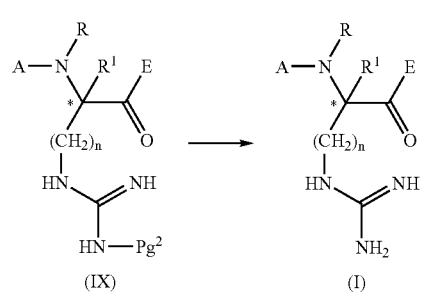

de-protecting the compound of formula (IX) to yield the corresponding compound of formula (I).

The present invention is further directed to a process for the preparation of the compound of formula

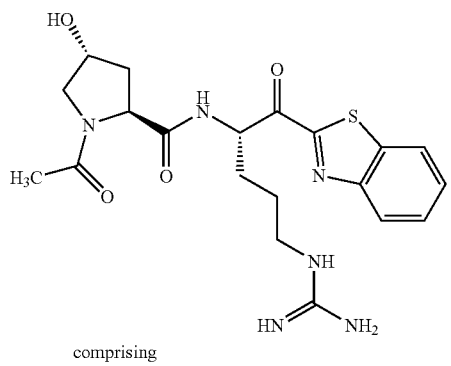

comprising

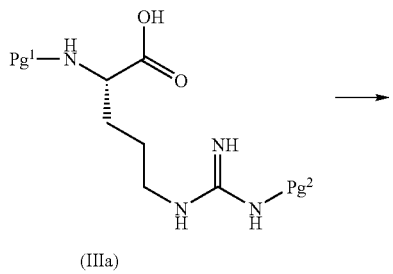

reacting a suitably substituted compound of formula (IIIa), wherein $Pg^1$ is a first nitrogen protecting group and $Pg^2$ is a second nitrogen protecting group; and wherein $Pg^1$ and $Pg^2$ are selected such that the $Pg^1$ protecting group may be removed under conditions which do not remove the $Pg^2$ protecting group; with a suitable activating agent; to yield the corresponding compound of formula (IVa), wherein $Q^1$ is a leaving group;

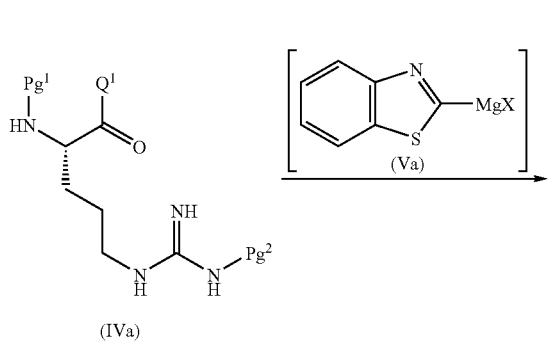

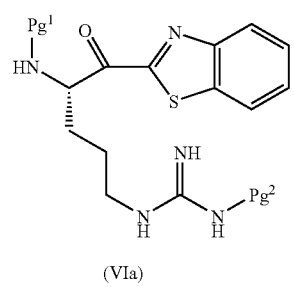

reacting the compound of formula (IVa) with a solution or suspension of a suitably substituted compound of formula (Va), wherein X is selected from the group consisting of Cl, Br and I; in an anhydrous organic solvent which is inert to the compound of formula (Va); to yield the corresponding compound of formula (VIa);

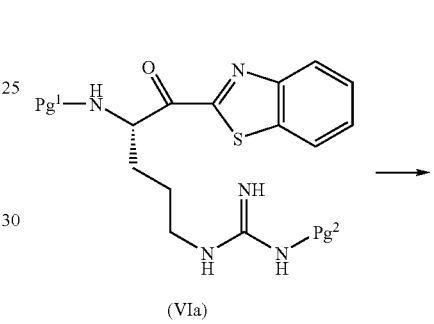

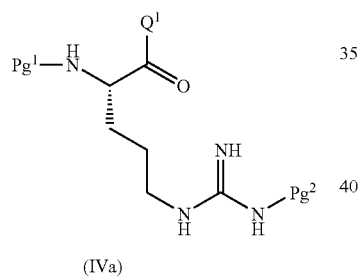

subjecting the compound of formula (VIa) to selective de-protection, to yield the corresponding compound of formula (VIIa) or its corresponding acid addition salt;

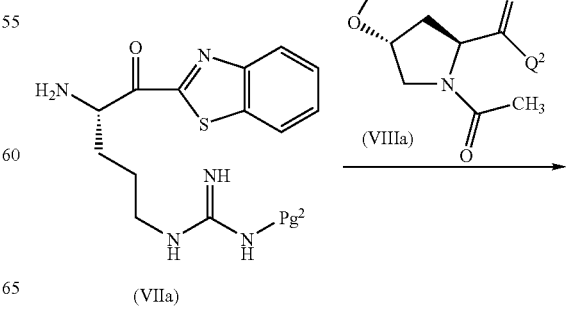

-continued

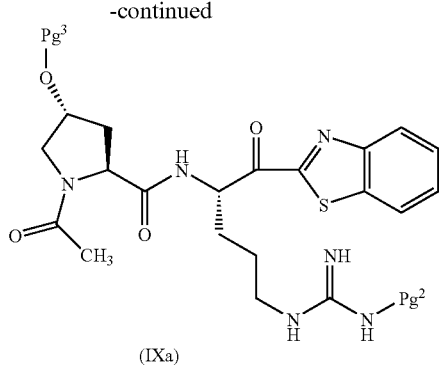

(IXa)

reacting the compound of formula (VIIa) with a suitably substituted compound of formula (VIIIa), wherein Pg³ is an oxygen protecting group; and wherein Q² is a leaving group; in the presence of a tertiary amine base; in an aprotic organic solvent; to yield the corresponding compound of formula (IXa);

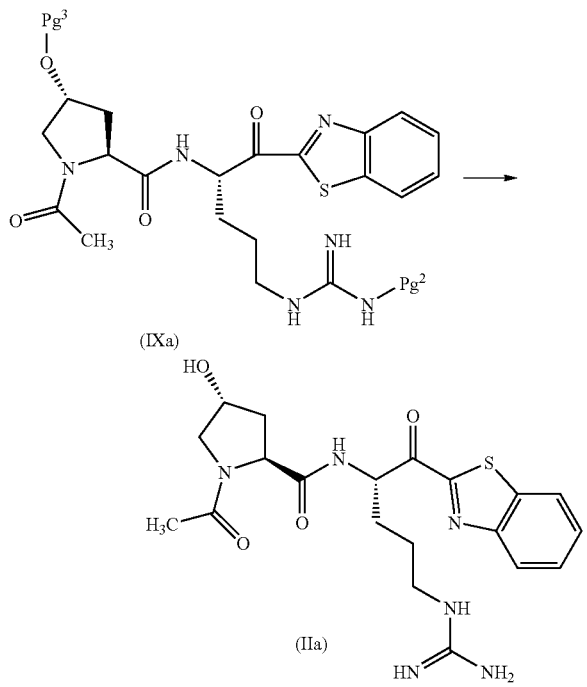

de-protecting the compound of formula (IXa), to yield the corresponding compound of formula (IIa).

The present invention is further directed to a process for the preparation of a compound of formula (Ia)

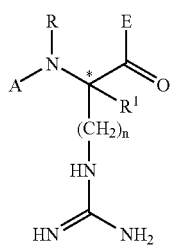

(Ia)

wherein

A is selected from the group consisting of substituted $C_{3-8}$cycloalkylcarbonyl (where the substituents on the $C_{3-8}$cycloalkyl group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted norbornanecarbonyl (where the substituents on the norbornane group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted norbornenecarbonyl (where the substituents on the norbornene group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted adamantanecarbonyl (where the substituents on the adamantine group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted arylcarbonyl (where the substituents on the aryl group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), heteroarylcarbonyl, substituted heteroarylcarbonyl (where the substituents on the heteroaryl are independently selected from one or more $C_{1-4}$alkyl, perfluoro$C_{1-4}$alkyl, $C_{1-4}$alkoxy, hydroxy, halo, amido, N-$C_{1-4}$alkylamido, N,N—C1-4dialkylamido, nitro, amino, $C_{1-4}$alkylamino, $C_{1-4}$dialkylamino, carboxy or $C_{1-4}$alkoxycarbonyl), pyridylcarbonyl, substituted pyridylcarbonyl (where the substituents on the pyridine ring are independently one to three substituents selected from $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), amido$C_{1-5}$alkylcarbonyl,

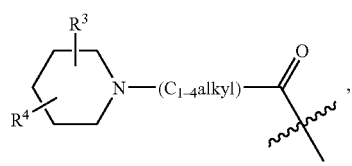

$C_{1-6}$alkyl-C(O)—N($R^8$)—$C_{0-6}$alkyl-C(O)—,

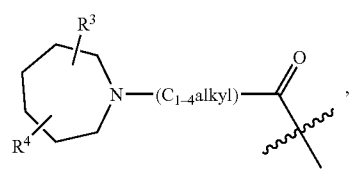

-continued

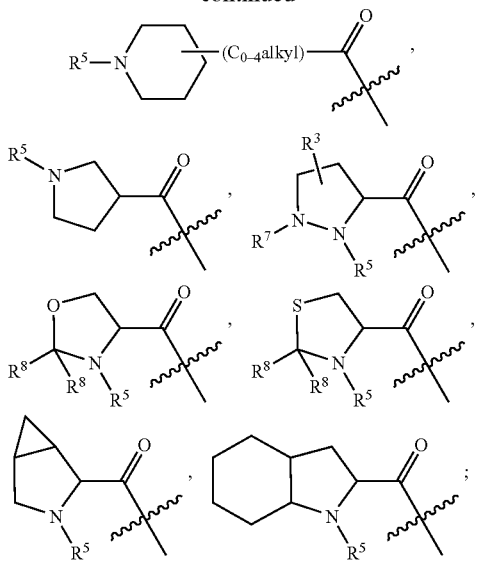

a D or L amino acid which is coupled at its carboxyterminus to the nitrogen depicted in formula (I) and is selected from the group consisting of alanine, glycine, dehydroproline, proline, substituted proline (where the substituents on the proline are independently selected from one or more of $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, phenylalkyloxy, phenyl or $C_{1-4}$alkoxycarbonyl), pipecolinic acid, substituted pipecolinic acid (where the substituents on the piperidine of the pipecolinic acid group are independently selected from one or more of $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, phenylalkyloxy, phenyl or $C_{1-4}$alkoxycarbonyl), valine, norleucine, leucine, tert-luecine, isoleucine, sarocosine, asparagine, serine, methionine, threonine, phenylalanine, 1-naphthalanine, 2-naphthalanine, 2-theintlalanine, 3-thienylalanine, [1,2,3,4]-tetrahydroisoquinoline-1-carboxylic acid and [1,2,3,4]-tetrahydroisoquinoline-2-carboxylic acid, where the amino terminus of said amino acid is connected to a member selected from the group consisting of [1,2,3,4]-tetrahydroisoquinoline-1-carbonyl, [1,2,3,4]-tetrahydroisoquinoline-3-carbonyl, formyl, $C_{1-4}$alkoxycarbonyl, $C_{1-8}$alkylcarbonyl, perfluoro $C_{1-4}$alkylsulfonyl, $C_{1-4}$alkylsulfonyl, amido, N-$C_{1-4}$alkylamido, N,N-$C_{1-4}$dialkylamido, sulfonamido, arylsulfonyl, substituted arylsulfonyl (where the aryl substituents are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy or $C_{1-4}$alkoxycarbonyl), camphorsulfonyl, $C_{1-4}$alkylsulfinyl, arylsulfinyl, substituted arylsulfinyl (where the aryl substituents are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy or $C_{1-4}$alkoxycarbonyl), and arylcarbonyl; or a polypeptide comprised of two amino acids
where the first amino acid is a D or L amino acid, bound via its carboxy terminus to the nitrogen depicted in formula (I) and is selected from the group consisting of proline and substituted proline (where the substituents on the proline are independently selected from one or more $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, aralkyloxy, aryl or $C_{1-4}$alkoxycarbonyl), and the second D or L amino acid, is bound to the amino terminus of said first amino acid and is selected from the group consisting of aspartic acid, aspartic acid-4-$C_{1-4}$alkyl ester, glutamic acid, glutamic acid-5-$C_{1-4}$alkyl ester, serine, phenylalanine, substituted phenylalanine (where the phenyl substituents are independently selected from one or more of $C_{1-4}$alkyl, perfluoro$C_{1-4}$alkyl, $C_{1-4}$alkoxy, hydroxy, halo, amido, nitro, amino, N-$C_{1-4}$alkylamino, N,N-$C_{1-4}$dialkylamino, carboxy or $C_{1-4}$alkoxycarbonyl), cyclohexylglycine, and cyclohexlalanine, where the amino terminus of said second amino acid is monosubstituted with a member of the group consisting of $C_{1-6}$alkyl, carboxy$C_{1-8}$alkyl and $C_{1-10}$alkylcarbonyl;

$R^3$ and $R^4$ are each independently selected from the group consisting of hydrogen, $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyloxy, $C_{1-4}$alkylcarbonylamino, aryl, substituted aryl (where the substituents on the aryl group are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, $C_{1-4}$alkylcarbonyl, $C_{1-4}$alkylcarbonylamino or $C_{1-4}$alkoxycarbonyl), $C_{1-4}$alkoxycarbonyl, aminosulfonyl, $C_{1-4}$alkylaminosulfonyl, $C_{1-4}$alkylsulfonylamino and N,N-di-$C_{1-4}$alkylaminosulfonyl;

$R^5$ is selected from the group consisting of hydrogen, $C_{1-4}$alkyl and $C_{1-4}$alkylcarbonyl;

$R^7$ is selected from the group consisting of hydrogen, $C_{1-4}$alkyl, $C_{1-4}$alkylcarbonyl and substituted aryl (where the substituents on the aryl group are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkylcarbonyl);

$R^8$ is selected from the group consisting of hydrogen and $C_{1-5}$alkyl;

R is selected from the group consisting of hydrogen and $C_{1-5}$alkyl;

$R^1$ is selected from the group consisting of hydrogen and $C_{1-5}$alkyl;

n is an integer from 2 to 3;

E is an unsubstituted or substituted heterocycle selected from the group consisting of imidazol-2-yl, oxazol-2-yl, thiazol-2-yl, 1,3,4-thiadiazol-2-yl, 1,2,4-thiadiazol-3yl, 1,2,4-thiadiazol-5-yl, isothiazol-3-yl, 1,2,3-triazol-4-yl, 1,2,3-triazol-5-yl, 1,2,4-triazin-3-yl, 1,3,5-triazin-2-yl, isoxazol-3-yl, 1,2,3,4-oxatriazol-5-yl, 1,2,3-oxadiazol-4-yl, 1,3,4-oxadiazol-2-yl, 1,2,4-oxadiazol-3-yl, 1,3,4-oxadiazol-2-yl, pyrazol-3-yl, pyrazin-2-yl, pyrimidin-2-yl, benzoxazol-2-yl, benzimidazol-2-yl, benzothiazol-2-yl, 4,5,6,7-tetrahydrobenzothiazol-2-yl, naphtho[2,1-d]thiazol-2-yl, naphtho[1,2- d]thiadiazol-2-yl, 4-oxoquinazolin-2-yl, quinazolin-2-yl, oxazolo[4,5-b]pyridin-2-yl, oxazolo[5,4-b]pyridin-2-yl, thiazolo[4,5-b]pyridin-2-yl, thiazolo[5,4-b]pyridin-2-yl and thiazolo[5,4-c]pyridin-2-yl, wherein the substituents on the heterocycle are independently selected from $C_{1-4}$alkyl, perfluoro$C_{1-4}$alkyl, $C_{1-4}$alkoxy, hydroxy, halogen, amido, nitro, N-$C_{1-4}$alkylamido, N,N-$C_{1-4}$dialkylamido, amino, $C_{1-4}$alkylamino, $C_{1-4}$dialkylamino, carboxy, $C_{1-4}$alkoxycarbonyl, phenyl$C_{1-4}$alkylaminocarbonyl, aryl or substituted aryl; wherein the substituents on the aryl group are one or more independently selected from the group consisting of $C_{1-4}$alkyl, perfluoro$C_{1-4}$alkyl, $C_{1-4}$alkoxy, halogen, N-$C_{1-4}$alkylamido, N,N-$C_{1-4}$dialkylamido, $C_{1-4}$dialkylamino, carboxy and $C_{1-4}$alkoxycarbonyl;

or a pharmaceutically acceptable salt thereof;

comprising

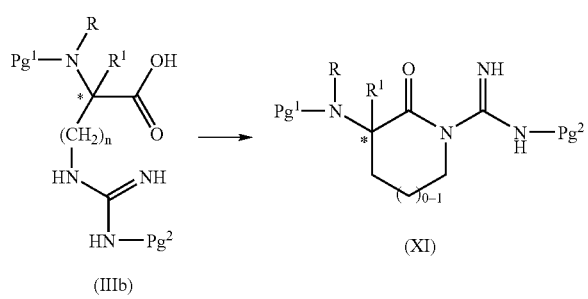

(IIIb)

reacting a suitably substituted compound of formula (IIIb), wherein $Pg^1$ is a first nitrogen protecting group and $Pg^2$ is a second nitrogen protecting group; and wherein $Pg^1$ and $Pg^2$ are selected such that the $Pg^1$ protecting group may be removed under conditions which do not remove the $Pg^2$ protecting group; with an activating agent capable of cyclizing the compound of formula (IIIb), to yield the corresponding compound of formula (XI);

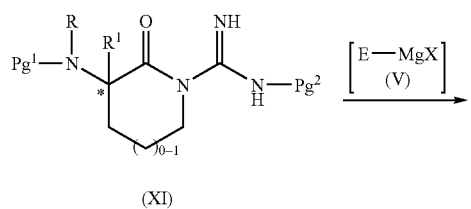

(XI)

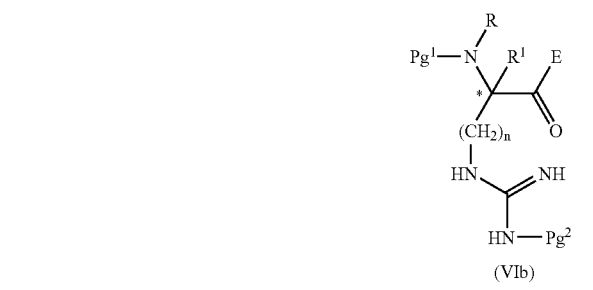

(VIb)

reacting the compound of formula (XI) with a solution or suspension of a suitably substituted compound of formula (V), wherein X is selected from the group consisting of Cl, Br and I; in an anhydrous organic solvent which is inert to the compound of formula (V); to yield the corresponding compound of formula (VIb);

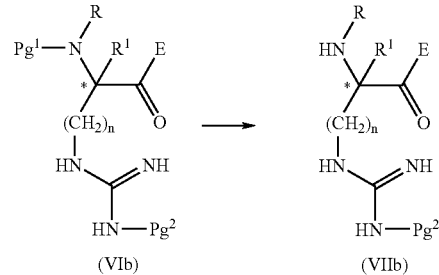

(VIb) (VIIb)

subjecting the compound of formula (VIb) to selective de-protection, to yield the corresponding compound of formula (VIIb) or its corresponding acid additon salt;

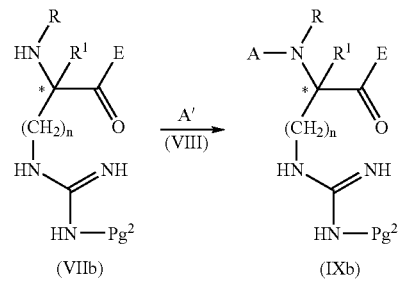

(VIIb) (IXb)

reacting the compound of formula (VIIb) with a suitably substituted compound of formula (VIII), wherein A' represents an activated form of the A substituent; in the presence of a tertiary amine base; in an aprotic organic solvent; to yield the corresponding compound of formula (IXb);

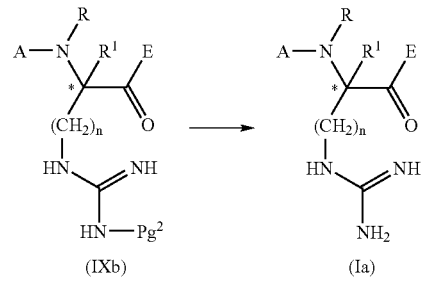

(IXb) (Ia)

de-protecting the compound of formula (IXb), to yield the corresponding compound of formula (Ia).

The present invention is further directed to a process for the preparation of a compound of formula (IIa)

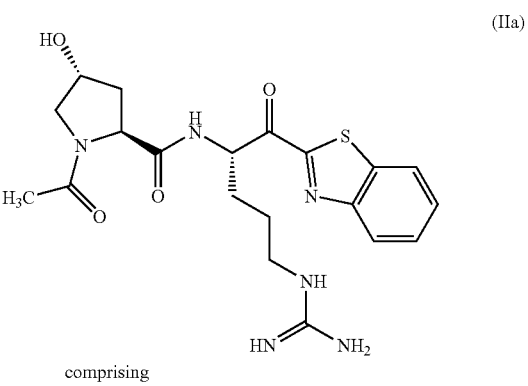

(IIa)

comprising

-continued

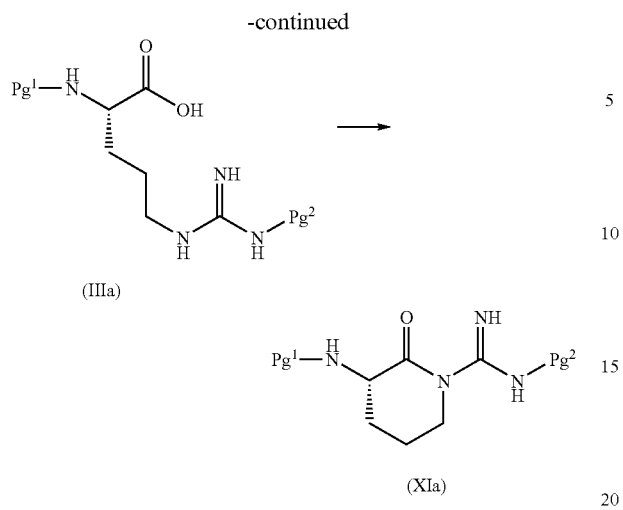

(IIIa)

(XIa)

reacting a suitably substituted compound of formula (IIIa), wherein Pg¹ is a first nitrogen protecting group and Pg² is a second nitrogen protecting group; and wherein Pg¹ and Pg² are selected such that the Pg¹ protecting group may be removed under conditions which do not remove the Pg² protecting group; with an activating agent capable of cyclizing the compound of formula (IIIa), to yield the corresponding compound of formula (XIa);

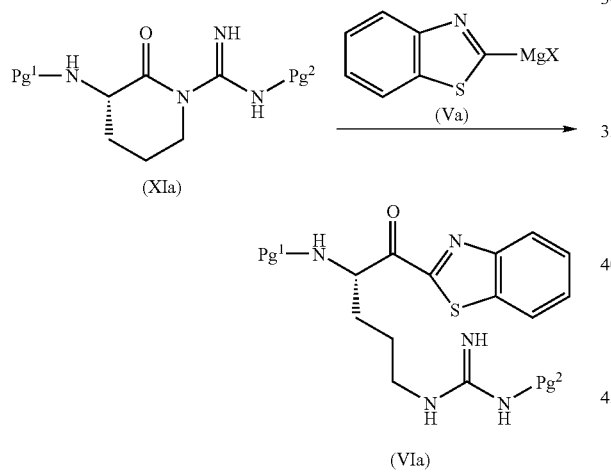

(XIa)

(VIa)

reacting the compound of formula (XIa) with a solution or suspension of a suitably substituted compound of formula (Va), wherein X is selected from the group consisting of Cl, Br and I; in an anhydrous organic solvent which is inert to the compound of formula (Va); to yield the corresponding compound of formula (VIa);

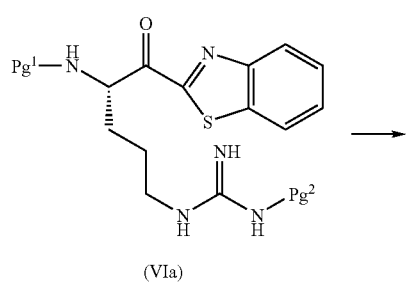

(VIa)

-continued

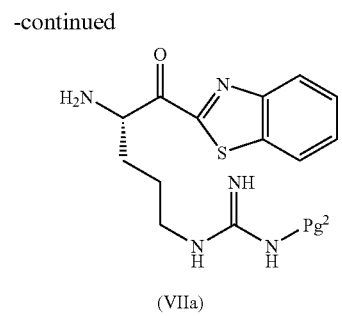

(VIIa)

subjecting the compound of formula (VIa) to selective de-protection, to yield the corresponding compound of formula (VIIa) or its corresponding acid addition salt;

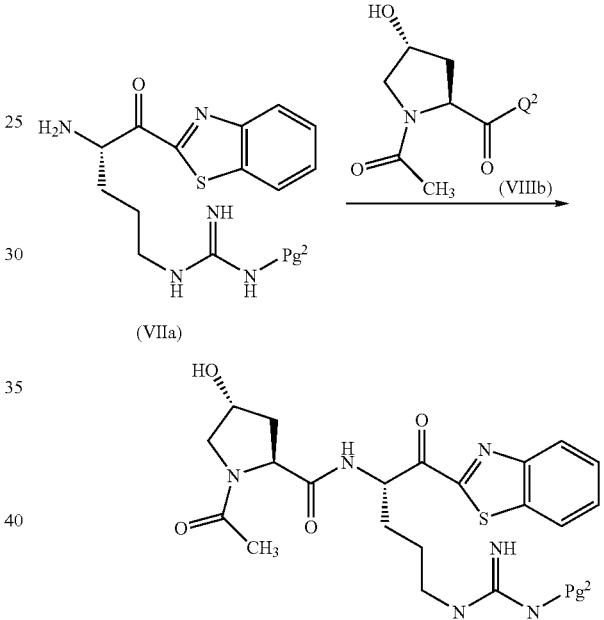

(VIIa)

(IXc)

reacting the compound of formula (VIIa) with a compound of formula (VIIIb), wherein $Q^2$ is a leaving group; in the presence of a tertiary amine base; in an aprotic organic solvent; to yield the corresponding compound of formula (IXc);

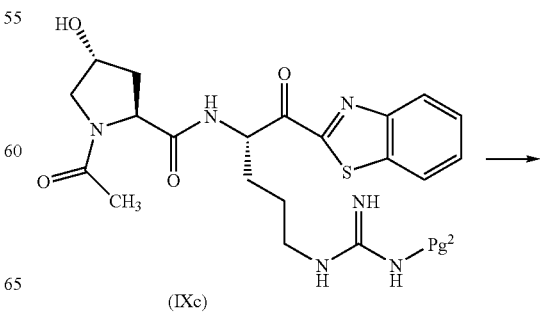

(IXc)

-continued

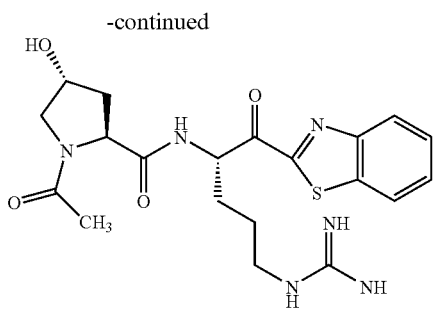

(IIa)

subjecting the compound of formula (IXc) to de-protection, to yield the corresponding compound of formula (IIa).

The present invention is further directed to a process for the preparation of a compound of formula (I)

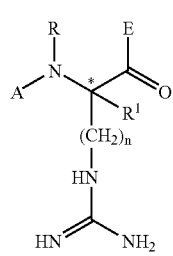

(I)

wherein

A is selected from the group consisting of substituted $C_{3-8}$cycloalkylcarbonyl (where the substituents on the $C_{3-8}$cycloalkyl group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted norbornanecarbonyl (where the substituents on the norbornane group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted norbornenecarbonyl (where the substituents on the norbornene group are independently selected from one or more $C_{1-4}$alkyl, perfluoro $C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted adamantanecarbonyl (where the substituents on the adamantine group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted arylcarbonyl (where the substituents on the aryl group are independently selected from one or more $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), heteroarylcarbonyl, substituted heteroarylcarbonyl (where the substituents on the heteroaryl are independently selected from one or more $C_{1-4}$alkyl, perfluoro $C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy or $C_{1-4}$alkoxycarbonyl), pyridylcarbonyl, substituted pyridylcarbonyl (where the substituents on the pyridine ring are independently one to three substituents selected from $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), amido$C_{1-5}$alkylcarbonyl,

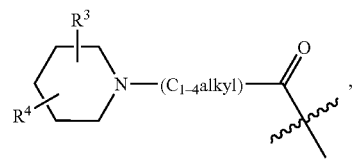

$C_{1-6}$alkyl-C(O)—N(R$^8$)—C$_{0-6}$alkyl-C(O)—,

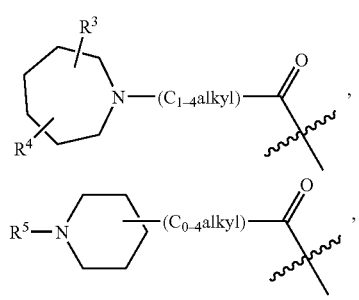

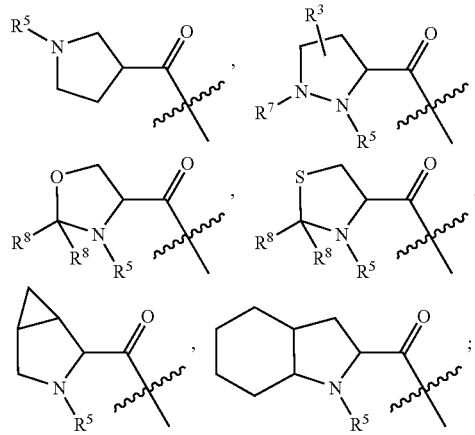

a D or L amino acid which is coupled at its carboxyterminus to the nitrogen depicted in formula (I) and is selected from the group consisting of alanine, glycine, dehydroproline, proline, substituted proline (where the substituents on the proline are independently selected from one or more of $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, phenylalkyloxy, phenyl or $C_{1-4}$alkoxycarbonyl), pipecolinic acid, substituted pipecolinic acid (where the substituents on the piperidine of the pipecolinic acid group are independently selected from one or more of $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, phenyalkyloxy, phenyl or $C_{1-4}$alkoxycarbonyl), valine, norleucine, leucine, tert-luecine, isoleucine, sarocosine, asparagine, serine, methionine, threonine, phenylalanine, 1-naphthalanine, 2-naphthalanine, 2-theintlalanine, 3-thienylalanine, [1,2,3,4]-tetrahydroisoquinoline-1-carboxylic acid and [1,2,3,4]-tetrahydroisoquinoline-2-carboxylic acid, where the amino terminus of said amino acid is connected to a member selected from the group consisting of [1,2,3,4]-tetrahydroisoquinoline-1-carbonyl, [1,2,3,4]-tetrahydroisoquinoline-3-carbonyl, formyl, $C_{1-4}$alkoxycarbonyl, $C_{1-8}$alkylcarbonyl, perfluoro $C_{1-4}$alkylsulfonyl, $C_{1-4}$alkylsulfonyl, amido, N-$C_{1-4}$alkylamido, N,N-$C_{1-4}$dialkylamido, sulfonamido, arylsulfonyl, substituted arylsulfonyl (where the aryl substituents are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy or $C_{1-4}$alkoxycarbonyl), camphorsulfonyl, $C_{1-4}$alkylsulfinyl, arylsulfinyl, substituted arylsulfinyl (where the aryl substituents are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy or $C_{1-4}$alkoxycarbonyl), and arylcarbonyl; or a polypeptide comprised of two amino acids where the first amino acid is a D or L amino acid, bound via its carboxy terminus to the nitrogen depicted in formula (I) and is selected from the group consisting of proline and substituted proline (where the substituents on the proline are independently selected from one or more $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, aralkyloxy, aryl or $C_{1-4}$alkoxycarbonyl), and the second D or L amino acid, is bound to the amino terminus of said first amino acid and is selected from the group consisting of aspartic acid, aspartic acid-4-$C_{1-4}$alkyl ester, glutamic acid, glutamic acid-5-$C_{1-4}$alkyl ester, serine, phenylalanine, substituted phenylalanine (where the phenyl substituents are independently selected from one or more of $C_{1-4}$alkyl, perfluoro$C_{1-4}$alkyl, $C_{1-4}$alkoxy, hydroxy, halo, amido, nitro, amino, N-$C_{1-4}$alkylamino, N,N-$C_{1-4}$dialkylamino, carboxy or $C_{1-4}$alkoxycarbonyl), cyclohexylglycine, and cyclohexlalanine, where the amino terminus of said second amino acid is monosubstituted with a member of the group consisting of $C_{1-6}$alkyl, carboxy$C_{1-8}$alkyl and $C_{1-10}$alkylcarbonyl;

$R^3$ and $R^4$ are each independently selected from the group consisting of hydrogen, $C_{1-4}$alkyl, perfluoro$C_{1-4}$alkyl, $C_{1-4}$alkoxy, hydroxy, oxo, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyloxy, $C_{1-4}$alkylcarbonylamino, aryl, substituted aryl (where the substituents on the aryl group are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, $C_{1-4}$alkylcarbonyl, $C_{1-4}$alkylcarbonylamino or $C_{1-4}$alkoxycarbonyl), $C_{1-4}$alkoxycarbonyl, aminosulfonyl, $C_{1-4}$alkylaminosulfonyl, $C_{1-4}$alkylsulfonylamino and N,N-di-$C_{1-4}$alkylaminosulfonyl;

$R^5$ is selected from the group consisting of hydrogen, $C_{1-4}$alkyl and $C_{1-4}$alkylcarbonyl;

$R^7$ is selected from the group consisting of hydrogen, $C_{1-4}$alkyl, $C_{1-4}$alkylcarbonyl and substituted aryl (where the substituents on the aryl group are independently selected from one or more of $C_{1-4}$alkyl, perfluoro$C_{1-4}$alkyl, $C_{1-4}$alkoxy, hydroxy, halo, amido, N-$C_{1-4}$alkylamido, N,N-$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkylcarbonyl);

$R^8$ is selected from the group consisting of hydrogen and $C_{1-5}$alkyl;

R is selected from the group consisting of hydrogen and $C_{1-5}$alkyl;

$R^1$ is selected from the group consisting of hydrogen and $C_{1-5}$alkyl;

n is an integer from 2 to 5;

E is an unsubstituted or substituted heterocycle selected from the group consisting of imidazol-2-yl, oxazol-2-yl, thiazol-2-yl, 1,3,4-thiadiazol-2-yl, 1,2,4-thiadiazol-3yl, 1,2,4-thiadiazol-5-yl, isothiazol-3-yl, 1,2,3-triazol-4-yl, 1,2,3-triazol-5-yl, 1,2,4-triazin-3-yl, 1,3,5-triazin-2-yl, isoxazol-3-yl, 1,2,3,4-oxatriazol-5-yl, 1,2,3-oxadiazol-4-yl, 1,3,4-oxadiazol-2-yl, 1,2,4-oxadiazol-3-yl, 1,3,4-oxadiazol-2-yl, pyrazol-3-yl, pyrazin-2-yl, pyrimidin-2-yl, benzoxazol-2-yl, benzimidazol-2-yl, benzothiazol-2-yl, 4,5,6,7-tetrahydrobenzothiazol-2-yl, naphtho[2,1-d]thiazol-2-yl, naphtho[1,2-d]thiadiazol-2-yl, 4-oxoquinazolin-2-yl, quinazolin-2-yl, oxazolo[4,5-b]pyridin-2-yl, oxazolo[5,4-b]pyridin-2-yl, thiazolo[4,5-b]pyridin-2-yl, thiazolo[5,4-b]pyridin-2-yl and thiazolo[5,4-c]pyridin-2-yl, wherein the substituents on the heterocycle are independently selected from $C_{1-4}$alkyl, perfluoro$C_{1-4}$alkyl, $C_{1-4}$alkoxy, hydroxy, halogen, amido, nitro, N-$C_{1-4}$alkylamido, N,N—$C_{1-4}$dialkylamido, amino, $C_{1-4}$alkylamino, $C_{1-4}$dialkylamino, carboxy, $C_{1-4}$alkoxycarbonyl, phenyl$C_{1-4}$alkylaminocarbonyl, aryl or substituted aryl; wherein the substituents on the aryl group are one or more independently selected from the group consisting of $C_{1-4}$alkyl, perfluoro$C_{1-4}$alkyl, $C_{1-4}$alkoxy, halogen, N-$C_{1-4}$alkylamido, N,N-$C_{1-4}$dialkylamido, $C_{1-4}$dialkylamino, carboxy and $C_{1-4}$alkoxycarbonyl;

or a pharmaceutically acceptable salt thereof;

comprising

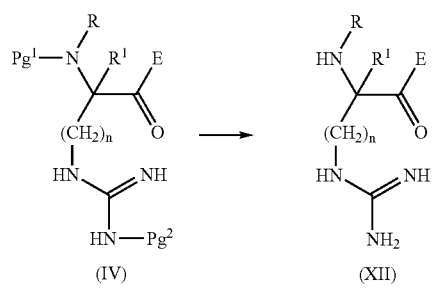

(IV)   (XII)

de-protecting a suitably substituted compound of formula (IV), wherein $Pg^1$ is a first nitrogen protecting group and $Pg^2$ is a second nitrogen protecting group; to yield the corresponding compound of formula (XII);

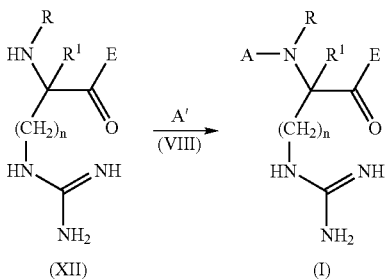

reacting the compound of formula (XII) with a suitably substituted compound of formula (VIII), wherein A' represents an activated form of the A substituent; in a polar solvent; to yield the corresponding compound of formula (I).

The present invention is further directed to a nitrate salt of the compound of formula (IIa). The present invention is further directed to a sulfate salt of the compound of formula (IIa).

The present invention is further directed to a sulfate salt of the compound of formula (IIa) characterized by its single crystal X-ray structure. The present invention is further directed to a sulfate salt of the compound of formula (IIa) characterized by its X-ray diffraction pattern. The present invention is further directed to a nitrate salt of the compound of formula (IIa) characterized by its X-ray diffraction pattern.

The present invention is further directed to a process for the preparation of a sulfate salt of the compound of formula (II)

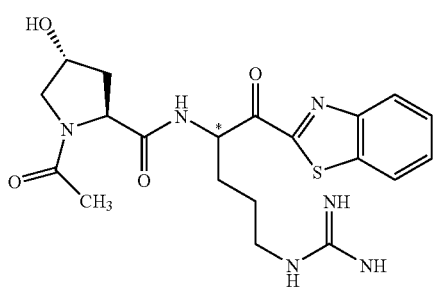

wherein the (1S) diastereomer predominates.

The present invention is further directed to a compound prepared according to any of the processes described herein.

Illustrative of the invention is a pharmaceutical composition comprising a pharmaceutically acceptable carrier and a compound prepared according to any of the processes described herein. An illustration of the invention is a pharmaceutical composition made by mixing a compound prepared according to any of the processes described herein and a pharmaceutically acceptable carrier. Illustrating the invention is a process for making a pharmaceutical composition comprising mixing a compound prepared according to any of the processes described herein and a pharmaceutically acceptable carrier.

Exemplifying the invention are methods of treating inflammatory disorders or trypsin mediated disorders in a subject in need thereof comprising administering to the subject a therapeutically effective amount of a compound prepared according to any of the processes described herein or a pharmaceutical composition as described above.

Further exemplifying the invention are methods for treating asthma, allergic rhinitis, rheumatoid arthritis, rheumatoid spondylitis, osteoarthritis, gouty arthritis, arthritic conditions in general (i.e. arthritis), peptic ulcers, ocular and vernal conjunctivitis, inflammatory bowel disease, Crohn's disease, chronic obstructive pulmonary disease (COPD), urticaria, bullous pemphigoid, scleroderma, fibrosis, dermatitis, psoriasis, angiodema, eczematous dermatitis, anaphylaxis, hyperproliferative skin disease, inflammatory skin conditions, hepatic cirrhosis, glomerulonephritis, nephritis, vascular inflammation, atherosclerosis, restenosis, and treating or preventing skin hyperpigmentation, in a subject in need thereof comprising administering to the subject a therapeutically effective amount of a compound prepared according to any of the processes described herein or a pharmaceutical composition as described above.

Another example of the invention is the use of a compound prepared according to any of the processes described herein in the preparation of a medicament for treating: (a) asthma, (b) allergic rhinitis, (c) rheumatoid arthritis, (d) rheumatoid spondylitis, (e) osteoarthritis, (f) gouty arthritis, (g) arthritis, (h) peptic ulcers, (i) ocular conjunctivitis, (j) vernal conjunctivitis, (k) inflammatory bowel disease, (l) Crohn's disease, (m) chronic obstructive pulmonary disease (COPD), (n) urticaria, (o) bullous pemphigoid, (p) scleroderma, (q) fibrosis, (r) dermatitis, (s) psoriasis, (t) angiodema, (u) eczematous dermatitis, (v) anaphylaxis, (w) hyperproliferative skin disease, (x) inflammatory skin condition, (y) hepatic cirrhosis, (z) glomerulonephritis, (aa) nephritis, (bb) vascular inflammation, (cc) atherosclerosis, (dd) restenosis or (ee) skin hyperpigmentation, in a subject in need thereof.

The processes of the instant invention, as described herein, are advantageous over previously disclosed methods in that they avoid toxic and/or explosive materials, do not require cryogenic temperatures, and/or do not require chromatographic separations. The processes of the present invention may also be applied to yield a final product wherein one stereo-isomer predominates.

BRIEF DESCRIPTION OF THE FIGURES

The following figures are not drawn to scale, and are set forth to illustrate various embodiments of the invention.

DETAILED DESCRIPTION OF THE INVENTION

Figure 1:
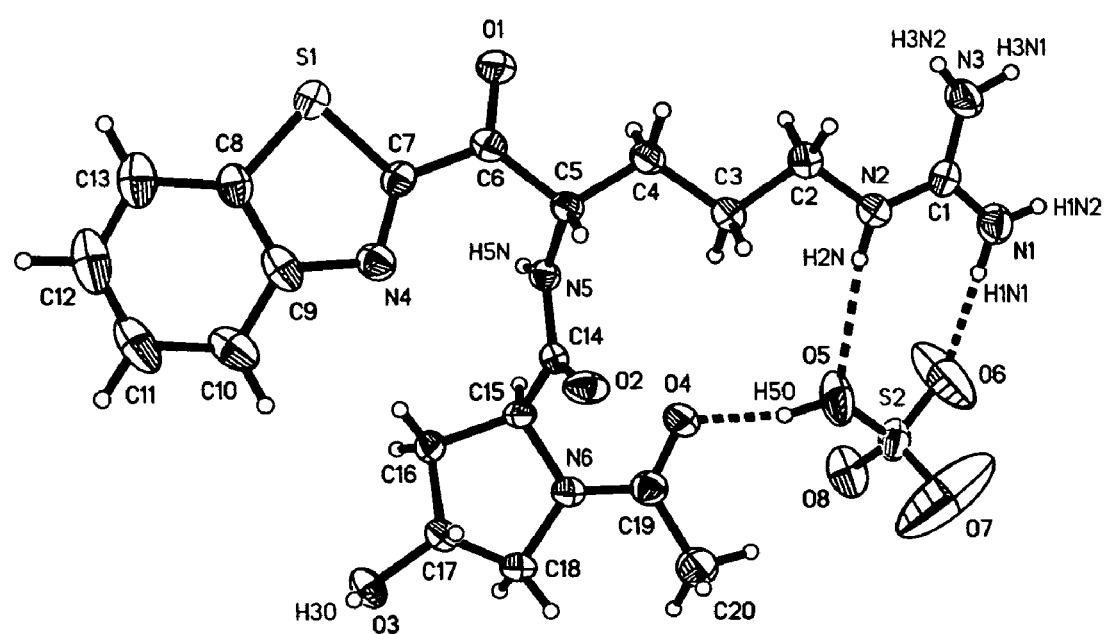
FIG. 1 illustrates a perspective drawing of the solid-state structure for the crystalline sulfate salt of the compound of formula (IIa) (i.e. (2S,4R)-1-Acetyl-N-[(1S)-1-(2-benzothiazolylcarbonyl)-4-[[imino(amino)methyl]amino]butyl]-4-hydroxypyrrolidine-2-carboxamide sulfate salt). Non-hydrogen atoms are represented by 50% probability thermal vibration ellipsoids and hydrogen atoms are represented by arbitrarily small spheres that are in no way representative of their true thermal motion.

As used herein, "halogen" shall mean chlorine, bromine, fluorine and iodine.

As used herein, the term "alkyl" whether used alone or as part of a substituent group, include straight and branched chains having 1 to 8 carbon atoms, or any number within this range. For example, alkyl radicals include methyl, ethyl, propyl, isopropyl, butyl, isobutyl, sec-butyl, t-butyl, pentyl and the like.

Similarly, the terms "alkenyl" and "alkynyl" shall include straight and branched chain alkene and alkyne groups, respectively, having 2 to 8 carbon atoms, or any number within this range.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the term "cycloalkyl" denotes groups containing 3 to 8 ring carbon atoms and preferably 5 to 7 ring carbon atoms.

As used herein, unless otherwise noted, "aryl" shall refer to an aromatic group such as phenyl, naphthyl, and the like.

As used herein, unless otherwise noted, "aralkyl" shall mean an alkyl group substituted with an aryl group. Suitable examples include, but are not limited to, benzyl, phenylethyl, naphthylmethyl, and the like.

As used herein, unless otherwise noted, the term "aralkyloxy" shall mean an alkoxy group substituted with an aryl group. Suitable examples include, but are not limited to, benzyloxy, phenylethoxy, naphthylmethoxy, and the like.

As used herein, unless otherwise noted, "heteroaryl" shall denote any stable five or six membered monocyclic aromatic ring structure or a nine or ten membered benzo-fused heteroaromatic ring system which consists of carbon atoms and from one to six heteroatoms (preferably one to four heteroatoms) selected from N, O or S. The heteroaryl group may be attached at any heteroatom or carbon atom which results in the creation of a stable structure. Examples of suitable heteroaryl groups include, but are not limited to, pyrrolyl, pyridyl, pyrazinyl, pyrimidinyl, pyrazolyl, pyridazinyl, furanyl, imidazolyl, thienyl, oxazolyl, isoxazolyl, thiazolyl, thiadiazolyl, triazolyl, tetrazolyl, purinyl, benzimidazolyl, benzofuranyl, benzothienyl, benzisoxazolyl, benzoxazolyl, benzopyranyl, indolyl, benzothiazolyl, benzothiadiazolyl, benzotriazolyl, quinolinyl, and the like.

As used herein, unless otherwise noted, the term "aminoalkyl" shall mean an alkyl group substituted with an amino group (i.e. -alkyl-$NH_2$). The term "alkylamino" shall mean an amino group substituted with an alkyl group (i.e. —NH-alkyl). Th term "dialkylamino" shall mean an amino group substituted with two alkyl groups, wherein the alkyl groups may be the same or different (i.e. —N-(alkyl)$_2$).

As used herein, unless otherwise noted, the term "amido" shall mean —C(O)—$NH_2$. Similarly the term "alkylamido" shall mean —C(O)—NH(alkyl) and the term "dialkylamido" shall mean —C(O)—N(alkyl)$_2$. As used herein, unless otherwise noted, the term "sulfonamido" shall mean —$SO_2$—$NH_2$. Similarly the term "alkylsulfonamido" shall mean —$SO_2$—NH(alkyl) and the term "dialkylsulfonamido" shall mean —$SO_2$—N(alkyl)$_2$.

As used herein, the notation "*" shall denote the presence of a stereogenic center.

As used herein, unless otherwise noted, the term "diastereomeric ratio" or "d.r." shall mean the molar ratio of the (1R) to the (1S) diastereomers of the compound of formula (II)

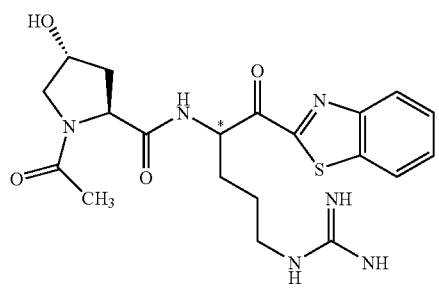

(II)

wherein the (1R) and (1S) configurations are at the "*" (starred) stereo-center.

As used herein, unless otherwise noted, the terms "activating agent" or "activating reagent" shall mean an agent or reagent which reacts with a chemical species so that the chemical species undergoes a chemical reaction more rapidly or completely. Suitable examples of activating agents or reagents include, but are not limited to CDI, isobutylchloroformate, $Ph_2POCl$, a mixture of $Ph_2POCl$ and PhSH, thionyl chloride (to form the corresponding acid chloride), a lower alkyl alcohol in the presence of an acid (to form the corresponding lower alkyl ester), and the like. Other suitable activating agents and methods for using them may be found in texts such as Bodanszky, M., *Principles of Peptide Synthesis*, $2^{nd}$ Ed., Springer-Verlag, 1993.

As used herein, unless otherwise noted, the term "aprotic organic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged substituent group on an activated compound which leaves during a substitution or displacement reaction. Suitable examples include, but are not limited to, —Cl, —O—C(O)—O-isobutyl, imidazolyl, —S-phenyl, —S-(2-pyridyl), and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R' wherein R' is for example methyl, ethyl, t-butyl, benzyl, phenylethyl, $CH_2$=CH—$CH_2$—, and the like; amides—groups of the formula —C(O)—R" wherein R" is for example methyl, phenyl, trifluoromethyl, and the like; N-sulfonyl derivatives—groups of the formula —$SO_2$—R'" wherein R'" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

As used herein, unless otherwise noted, the term "antisolvent" shall refer to a solvent which does not dissolve a specific substance and is added to a solution of said substance, directly or by vapor diffusion, to cause precipitation of said substance.

With reference to substituents, the term "independently" means that when more than one of such substituents is possible, such substituents may be the same or different from each other.

When a particular group is "substituted" (e.g., phenyl, aryl, aralkyl, heteroaryl), that group may have one or more substituents, preferably from one to five, more preferably one to three, most preferably, one to two substituents, independently selected from the list of substituents.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Abbreviations used in the specification, particularly the Schemes and Examples, are as follows:

| | |
|---|---|
| ACN = | Acetonitrile |
| Arg = | Arginine |
| BOC or Boc | t-butoxycarbonyl |
| CBz or Z = | Benzyloxycarbonyl |
| CDI = | N,N'-Carbonyldiimidazole |
| DBU = | 1,8-Diazabicyclo[5.4.0]undec-7-ene |
| DCC = | 1,3-dicyclohexylcarbodiimide |
| DCE = | Dichloroethane |
| DCM = | Dichloromethane |
| DMF = | N,N-dimethylformamide |
| EtOAc = | Ethyl acetate |
| Fmoc = | N-(9-fluorenylmethoxycarbonyl) |
| HPLC = | High Pressure Liquid Chromatography |
| IPA = | Isopropyl acohol |
| Me = | Methyl |
| MeOH = | Methanol |
| MOM = | Methoxymethyl |
| MTBE = | Methyl-t-butyl ether |
| Mtr = | 2,3,6-trimethyl-4-methoxy-phenyl-sulfonyl |
| NMM = | N-methylmorpholine |
| Ph = | Phenyl |
| PhSH = | Benzenethiol |
| Ph$_2$POCl = | Diphenyl phosphinic chloride |
| RBF = | Round Bottom Flask |
| TBDMSCl = | tert-Butyldimethylchlorosilane |
| TEA or Et$_3$N = | Triethylamine |
| TFA = | Trifluoroacetic acid |
| THF = | Tetrahydrofuran |
| THP = | Tetrahydropyranyl |
| TLC = | Thin Layer Chromatography |
| TMS = | Trimethylsilyl |
| XRD= = | X-Ray Diffraction |

In a preferred embodiment of the present invention, the inflammatory disorder is an immunomediated inflammatory disorder, more preferably a mast cell mediated inflammatory disorder. Examples of immunomediated inflammatory disorders include, but are not limited to asthma, allergic rhinitis, rheumatoid arthritis, rheumatoid spondylitis, osteoarthritis, gouty arthritis, arthritic conditions in general (i.e. arthritis), peptic ulcers, ocular and vernal conjunctivitis, inflammatory bowel disease, Crohn's disease, chronic obstructive pulmonary disease (COPD), urticaria, bullous pemphigoid, scleroderma, fibrosis, dermatitis, psoriasis, angiodema, eczematous dermatitis, anaphylaxis, hyperproliferative skin disease, inflammatory skin conditions, hepatic cirrhosis, glomerulonephritis, nephritis, vascular inflammation, atherosclerosis and restenosis In another embodiment of the present invention, is a method for treating or preventing skin hyperpigmentation.

In an embodiment of the present invention is a process for the preparation of a compound of formula (I) wherein n is 3.

In an embodiment of the present invention is a process for the preparation of a compound of formula (I) wherein E is an unsubstituted or substituted heterocycle selected from the group consisting of imidazol-2-yl, oxazol-2-yl, thiazol-2-yl, benzoxazol-2-yl, benzimidazol-2-yl, benzothiazol-2-yl, 4,5, 6,7-tetrahydro-benzothiazol-2-yl, 4-oxoquinazolin-2-yl and quinazolin-2-yl; wherein the substituents on the heterocycle are one to two independently selected from C$_{1-4}$alkyl, perfluoroC$_{1-4}$alkyl, $_{1-4}$alkoxy, halogen, N-C$_{1-4}$alkylamido, N,N-C$_{1-4}$dialkylamido, carboxy or C$_{1-4}$alkoxycarbonyl. Preferably, E is benzothiazol-2-yl.

In an embodiment of the present invention is a process for the preparation of a compound of formula (I) wherein R' is hydrogen and R$_1$ is hydrogen.

In an embodiment of the present invention is a process for the preparation of a compound of formula (I) wherein A is 1-acetyl-4R-hydroxy-pyrrolidin-2S-yl-carbonyl.

In an embodiment of the present invention is a process for the preparation of a compound of formula (II)

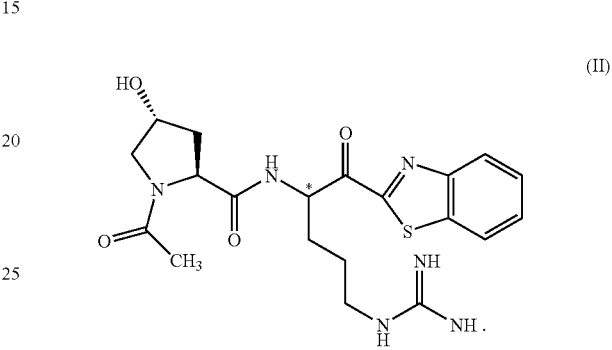

(II)

In another embodiment of the present invention is a process for the preparation of the (1S) diastereomer of the compound of formula (II).

In yet another embodiment, the present invention is directed to a process for the preparation of a compound of formula (IIa)

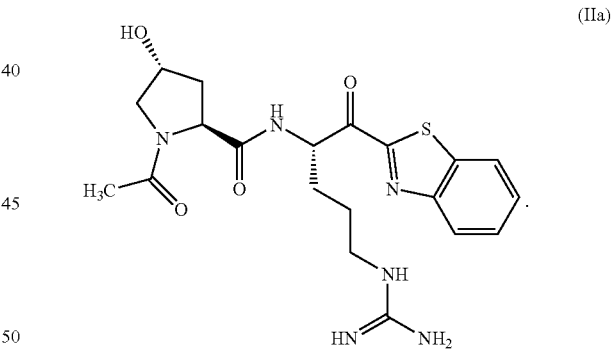

(IIa)

The present invention is further directed to a process for the preparation of a sulfate salt of the compound of formula (II) wherein the (1S) diastereomer predominates.

The present invention is further directed to a crystalline acid addition salt of the compound of formula (IIa). In an embodiment of the present invention is a nitric acid or sulfuric acid addition salt, preferably a sulfuric acid addition salt of the compound of formula (IIa). In another embodiment of the present invention is a crystalline nitrate or sulfate salt of the compound of formula (IIa).

The present invention is further directed to a process for the preparation of a nitrate or sulfate salt of the compound of formula (IIa). In an embodiment of the present invention is a process for the preparation of crystalline nitrate or sulfate salt of the compound of formula (IIa), preferably a crystalline sulfate salt of the compound of formula (IIa). In yet another embodiment of the present invention is a process for the purification of a nitrate or sulfate, preferably a sulfate, salt of the compound of formula (IIa).

Compounds of formula (I) may be prepared according to the process outlined in Scheme 1.

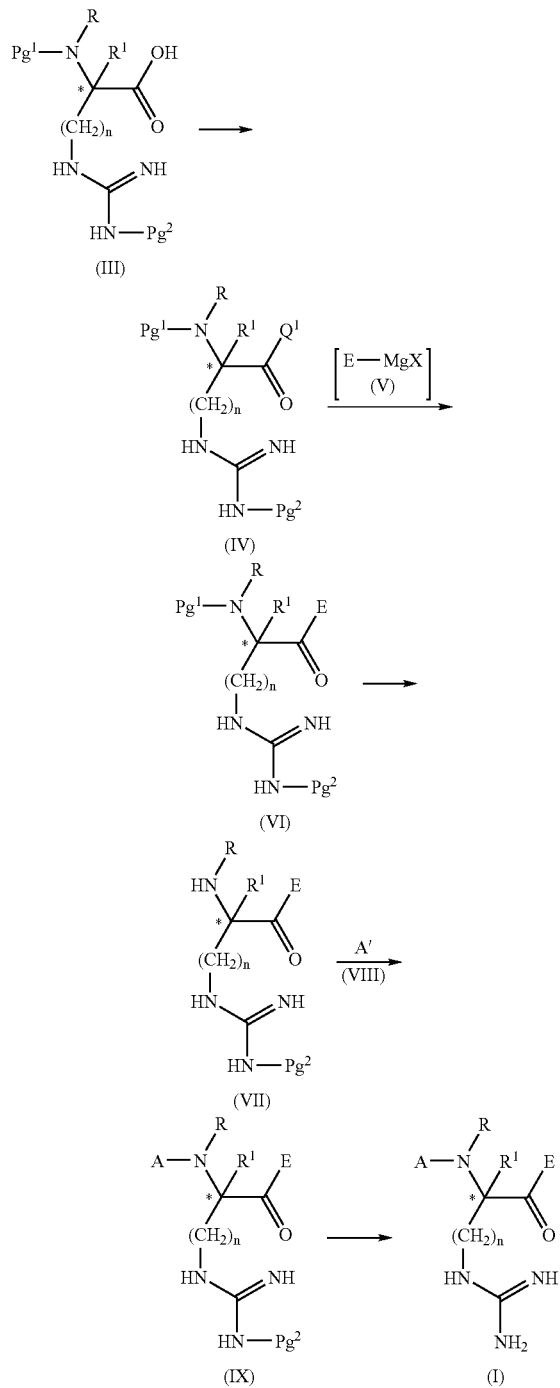

Accordingly, a suitably substituted compound of formula (III), wherein $Pg^1$ is a first suitable nitrogen protecting group such as t-butoxycarbonyl (BOC), benzyloxycarbonyl (CBz), N-(9-fluorenylmethoxycarbonyl) (Fmoc) and the like, pref- erably BOC; and $Pg^2$ is a second suitably nitrogen protecting group such as 4-methoxy-2,3,6-trimethyl-phenylsulfonyl (MTr), benzyloxycarbonyl (CBz), p-toluene-sulfonyl, t-bu-toxycarbonyl (BOC) and the like, preferably MTr; and wherein $Pg^1$ and $Pg^2$ are selected such that the $Pg^1$ protecting group may be removed under conditions which do not remove the $Pg^2$ protecting group, a known compound or compound prepared by known methods; is reacted to acti- vate the carboxylic acid portion of the compound of formula (III), by reacting the compound of formula (III) with a suitable activating agent, preferably under anhydrous con- ditions, to yield the corresponding compound of formula (IV) (an activated form of the compound of formula (III), wherein $Q^1$ is a leaving group). The compound of formula (IV) is optionally isolated prior to the next step.

One skilled in the art will recognize that when the compound of formula (IV) is not isolated prior to the next step, the activation of the compound of formula (III) to the corresponding compound of formula (IV) is preferably completed under anhydrous conditions.

For example, the compound of formula (III) may be reacted with CDI in an aprotic organic solvent such as THF, dioxane, ethyl acetate, and the like, to yield the correspond- ing compound of formula (IV) wherein $Q^1$ is imidazolyl.

Alternatively, the compound of formula (III) may be reacted with isobutylchloroformate, in the presence of an organic base, preferably in the presence of a tertiary amine base such as diisopropylethylamine, N-methylmorpholine, triethylamine, pyridine, and the like, in a chlorinated solvent such as DCE, DCM, and the like, at a temperature in the range of about −20 to about 10° C., followed by addition of N,O-dimethylhydroxyamine HCl salt and a tertiary amine base such as diisopropylethylamine, N-methylmorpholine, and the like, to yield the corresponding compound of for- mula (IV) wherein $Q^1$ is —N(CH$_3$) (OCH$_3$).

Alternatively still, the compound of formula (III) may be reacted with Ph$_2$POCl, in the presence of an organic base, preferably in the presence of a tertiary amine base such as TEA, DIPEA, pyridine, and the like, in an anhydrous, aprotic organic solvent such as THF, dioxane, MTBE, DCM, DCE, and the like, preferably at a temperature in the range of about −20 to about 15° C., to yield the corresponding compound of formula (IV) wherein $Q^1$ is —O—POPh$_2$.

The compound of formula (IV) is reacted with a solution or suspension of a suitably substituted compound of formula (V), wherein E is a defined above and wherein X is selected from the group consisting of Cl, Br and I, preferably Cl or Br, more preferably Cl; in an anhydrous organic solvent which is inert to the compound of formula (V) (i.e. in an anhydrous organic solvent which does not react with the compound of formula (V)) such as THF, diethyl ether, glyme, MTBE, and the like; preferably the anhydrous organic solvent which is inert to the compound of formula (V) is the solvent in which the compound of formula (IV) was prepared; preferably, the compound of formula (IV) is added to the compound of formula (V); preferably, the temperature of the reaction is maintained in the range of about −20° C. to about 15° C., more preferably the tem- perature of the reaction is maintained in the range of about −10 to about 5° C., to yield the corresponding compound of formula (VI).

The compound of formula (VI) is subjected to selective de-protection, to yield the corresponding compound of for- mula (VII).

For example, wherein $Pg^1$ is a nitrogen protecting group which may be removed under acid conditions, such as BOC, the compound of formula (VI) is reacted with an acid such as hydrochloric acid, hydrobromic acid, sulfuric acid, trifluoroacetic acid (TFA), and the like, preferably hydrochloric acid, in an organic solvent such as methanol, ethyl acetate, glyme, THF, and the like, or a mixture thereof, preferably a mixture of methanol and ethyl acetate, to yield the corresponding compound of formula (VII) as the acid addition salt.

Alternatively, wherein $Pg^1$ is a nitrogen protecting group which may be removed under catalytic hydrogenation conditions, such as CBz, the compound of formula (VI) is reacted with hydrogen gas, in the presence of a catalytic amount of a catalyst such as Pd on carbon, and the like, in the presence of an acid such as hydrochloric acid, sulfuric acid, trifluoroacetic acid, and the like, to yield the corresponding compound of formula (VII). One skilled in the art will recognize that when the hydrogenation is completed in the presence of an acid, the de-protection yields the corresponding compound of formula (VII) as the acid addition salt.

Alternatively still, wherein $Pg^1$ is a nitrogen protecting group which may be removed under basic conditions, such as Fmoc, the compound of formula (VI) is reacted with a secondary amine base such as piperidine, morpholine, dicyclohexylamine, and the like, preferably piperidine, in an organic solvent such as ethyl acetate, glyme, THF, and the like, to yield the corresponding compound of formula (VII).

Preferably, $Pg^1$ is a nitrogen protecting group which may be removed under acidic conditions or under catalytic hydrogenation conditions.

One skilled in the art will recognize that the compound of formula (VII), in the form of the free amine, is not stable over time. Therefore, it is preferred that the compound of formula (VII), as the free amine, is reacted in the next step within a short period of time, e.g. before significant degradation.

Preferably, wherein $Pg^1$ is a nitrogen protecting group which may be removed under basic conditions, the compound of formula (VII) is isolated as an acid addition salt, according to known methods (e.g. by reacting with a suitable acid such as HCl).

The compound of formula (VII) is reacted with a suitably substituted compound of formula (VIII), wherein A' represents an activated form of the A substituent, a known compound or compound prepared by known methods; in the presence of a tertiary amine base such as DIPEA, TEA, N-methylmorpholine, and the like; in an aprotic organic solvent such as acetonitrile, ethyl acetate, MTBE, THF, and the like, preferably acetonitrile or THF; preferably under anhydrous conditions; preferably, the compound of formula (VII) is added to the compound of formula (VIII); preferably, the temperature of the reaction is maintained in the range of about −20° C. to about 15° C., more preferably the temperature of the reaction is maintained in the range of about −5 to about 5° C.; to yield the corresponding compound of formula (IX).

One skilled in the art will recognize that in the compound of formula (VIII), it may be necessary or desirable to protect one or more portions of the A group according to known methods. Suitable protecting groups include, but are not limited to silyl containing protecting group such as t-butyl-dimethyl-silyl, and the like; a benzyl group; a MOM group; and the like. Preferably, the A protecting group is t-butyl-dimethyl-silyl.

The compound of formula (IX) is subjected to de-protection to remove the $Pg^2$ protecting group (and wherein the A group is protected, the A protecting group) according to known methods, to yield the corresponding compound of formula (I).

One skilled in the art will recognize that the process as outlined in Scheme 1 above, may alternatively be applied to a compound of formula (III) wherein the guandine portion is bis-protected, a compound of the formula (X)

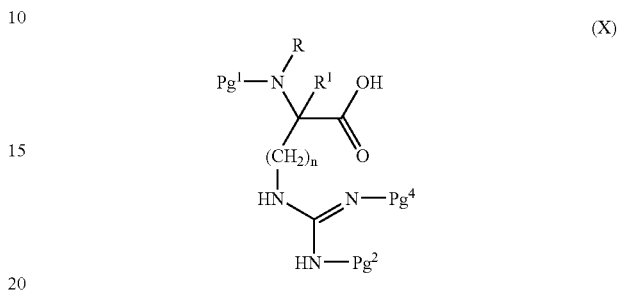

wherein $Pg^4$ is a third suitable nitrogen protecting group, and wherein $Pg^4$ is the same as $Pg^2$. One skilled in the art will further recognize that the $Pg^4$ group is selected such that the $Pg^4$ group is not removed under the conditions which remove the $Pg^1$ group. More particularly, the $Pg^4$ group is removed at the same time, immediately prior to or immediately after de-protection removal of the $Pg^2$ protecting group, according to known methods.

Compounds of formula (Ia) (i.e. compounds of formula (I) wherein n is an integer selected from 2 to 3) may alternatively be prepared according to the process outlined in Scheme 2.

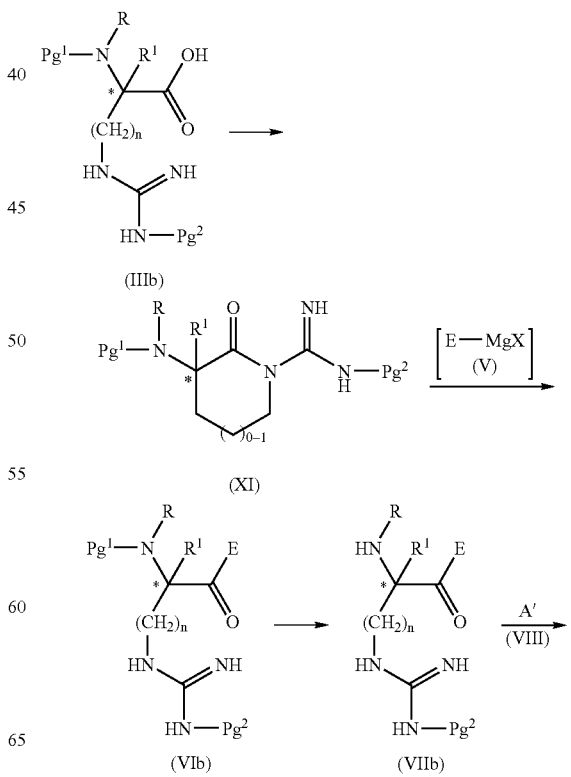

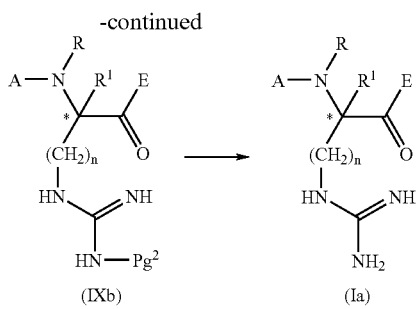

(IXb) → (Ia)

Accordingly, a suitably substituted compound of formula (IIIb), a compound of formula (III) wherein n is an integer from 2 to 3, wherein $Pg^1$ is a first suitable nitrogen protecting group such as t-butoxycarbonyl (BOC), benzyloxycarbonyl (CBz), N-(9-fluorenylmethoxycarbonyl) (Fmoc) and the like, preferably BOC; and $Pg^2$ is a second suitable nitrogen protecting group such as 4-methoxy-2,3,6-trimethyl-phenyl-sulfonyl (MTr), benzyloxycarbonyl (CBz), p-toluene-sulfonyl, t-butoxycarbonyl (BOC) and the like, preferably CBz; and wherein $Pg^1$ and $Pg^2$ are selected such that the $Pg^1$ protecting group may be removed under conditions which do not remove the $Pg^2$ protecting group; a known compound or compound prepared by known methods; is reacted with an activating agent capable of cyclizing the compound of formula (IIIb), such as isobutylchloroformate, $SOCl_2$,

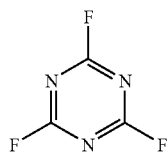

(2,4,6-trifluoro-[1,3,5]triazine), and the like, to yield the corresponding compound of formula (XI).

For example the compound of formula (IIIb) is reacted with isobutylchloroformate, a known compound, in an organic solvent such as THF, diethyl ether, glyme, MTBE, ethyl acetate, methylene chloride, and the like; or a mixture of an organic solvent and water, such as a 1:1 mixture of THF:water, and the like; in the presence of an organic amine base, preferably a tertiary amine base such as TEA, DIPEA, pyridine, and the like; preferably at a temperature in the range of about −15 to about 10° C., more preferably at a temperature in the range of −5 and 50° C.; to yield the corresponding compound of formula (XI).

Alternatively, the compound of formula (IIIb) is reacted with $SOCl_2$, in an aprotic organic solvent that is inert to the compound of formula (IIIb) such as DCM, DCE, toluene, and the like, preferably at a temperature in the range of about −20 to about 15° C., more preferably at a temperature in the range of about −5 to about 5° C., to yield the corresponding compound of formula (XI).

Alternatively still, the compound of formula (IIIb) is reacted with 2,4,6-trifluoro-[1,3,5]triazine (also known as cyanuric fluoride), in an aprotic organic solvent that is inert to the compound of formula (IIIb) such as DCM, DCE, toluene, and the like, preferably at a temperature in the range of about −20 to about 15° C., more preferably at a temperature in the range of about −5 to about 5° C., to yield the corresponding compound of formula (XI).

The compound of formula (XI) is reacted with a solution or suspension of a suitably substituted compound of formula (V), wherein E is as previously defined and wherein X is selected from the group consisting of Cl, Br and I, preferably Cl or Br, more preferably Cl, a known compound or compound prepared by known methods; in an anhydrous organic solvent which is inert to the compound of formula (V) (i.e. in an anhydrous organic solvent which does not react with the compound of formula (V)) such as THF, diethyl ether, glyme, MTBE, and the like; preferably the anhydrous organic solvent which is inert to the compound of formula (V) is the solvent in which the compound of formula (IX) was prepared; preferably, the compound of formula (IX) is added to the compound of formula (V); preferably, the temperature of the reaction is maintained in the range of about −20° C. to about 15° C., more preferably the temperature of the reaction is maintained in the range of about −10 to about 0° C., more preferably still, the temperature of the reaction is maintained in the range of about −10 to about −5° C.; to yield the corresponding compound of formula (VIb).

The compound of formula (VIb) is subjected to selective de-protection, to yield the corresponding compound of formula (VIIb).

For example, wherein $Pg^1$ is a nitrogen protecting group which may be removed under acid conditions, such as BOC, the compound of formula (VIb) is reacted with an acid such as hydrochloric acid, hydrobromic acid, sulfuric acid, trifluoroacetic acid (TFA), and the like, preferably hydrochloric acid, in an organic solvent such as methanol, ethyl acetate, glyme, THF, and the like, or a mixture thereof, preferably a mixture of methanol and ethyl acetate, to yield the corresponding compound of formula (VIIb) as the acid addition salt.

Alternatively, wherein $Pg^1$ is a nitrogen protecting group which may be removed under catalytic hydrogenation conditions, such as CBz, the compound of formula (VIb) is reacted with hydrogen gas, in the presence of a catalytic amount of a catalyst such as Pd on carbon, and the like, in the presence of an acid such as hydrochloric acid, sulfuric acid, trifluoroacetic acid, and the like, to yield the corresponding compound of formula (VIIb). One skilled in the art will recognize that when the hydrogenation is completed in the presence of an acid, the de-protection yields the corresponding compound of formula (VIIb) as the acid addition salt.

Alternatively still, wherein $Pg^1$ is a nitrogen protecting group which may be removed under basic conditions, such as Fmoc, the compound of formula (VIb) is reacted with a secondary amine base such as piperidine, morpholine, dicyclohexylamine, and the like, preferably piperidine, in an organic solvent such as ethyl acetate, glyme, THF, and the like, to yield the corresponding compound of formula (VIIb).

Preferably, $Pg^1$ is a nitrogen protecting group which may be removed under acidic conditions or under catalytic hydrogenation conditions.

One skilled in the art will recognize that the compound of formula (VIIb), in the form of the free amine, is not stable over time. Therefore, it is preferred that the compound of formula (VIIb), as the free amine, is reacted in the next step within a short period of time, e.g. before significant degradation.

Preferably, wherein $Pg^1$ is a nitrogen protecting group which may be removed under basic conditions, the compound of formula (VIIb) is isolated as an acid addition salt, according to known methods (e.g. by reacting with a suitable acid such as HCl).

The compound of formula (VIIb) is reacted with a suitably substituted compound of formula (VIII), wherein A' represents an activated form of the A substituent, a known compound or compound prepared by known methods; in the presence of a tertiary amine base such as DIPEA, TEA, N-methylmorpholine, and the like; in an aprotic organic solvent such as acetonitrile, ethyl acetate, MTBE, THF, and the like, preferably acetonitrile or THF; preferably under anhydrous conditions; preferably, the compound of formula (VIIb) is added to the compound of formula (VIII); preferably, the temperature of the reaction is maintained in the range of about −20° C. to about 15° C., more preferably the temperature of the reaction is maintained in the range of about −5 to about 5° C.; to yield the corresponding compound of formula (IXb).

One skilled in the art will recognize that in the compound of formula (VIII), it may be necessary or desirable to protect one or more portions of the A group according to known methods. Suitable protecting groups include, but are not limited to silyl containing protecting group such as t-butyl-dimethyl-silyl, and the like, a benzyl group, a MOM group, and the like. Preferably, the A protecting group is t-butyl-dimethyl-silyl.

The compound of formula (IXb) is subjected to de-protection to remove the $Pg^2$ protecting group (and wherein the A group is protected, the A protecting group) according to known methods, to yield the corresponding compound of formula (Ia).

The protecting groups on the compounds of formula (VIb), (VIII) (when necessary or desired) and (IXb) may be removed according to known methods, under de-protection conditions (for example as herein described or as described in T. W. Greene & P. G. M. Wuts, *Protective Groups in Organic Synthesis*, John Wiley & Sons, 1991).

One skilled in the art will recognize that the compound of formula (III)

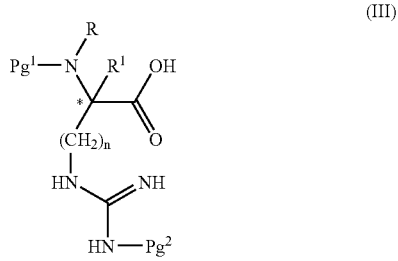

(III)

may be selected as a racemate, as a mixture of enantiomers, as a mixture of enantiomers wherein one enantiomers is enriched or as a single enantiomers (i.e. with a specific stereo-orientation at the starred (*) stereocenter). Preferably, the compound of formula (III) is selected as a pure enantiomer or a mixture of enantiomers wherein one enantiomer is enriched. Preferably, the compound of formula (III) is selected such that one enantiomer is present in an amount greater than about 50 percent, more preferably in an amount greater than about 80 percent, more preferably still, in an amount greater than about 95 percent, most preferably, in an amount greater than about 99 percent.

Compounds of formula (I) may alternatively be prepared from the corresponding, suitably substituted, compound of formula (IV), according to the process outlined in Scheme 3.

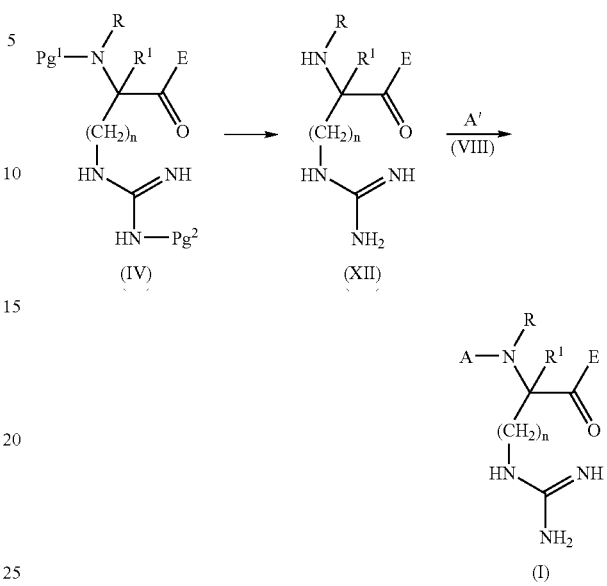

Scheme 3

Accordingly, a suitably substituted compound of formula (IV) is de-protected according to known methods, to remove both protecting groups, $Pg^1$ and $Pg^2$, to yield the corresponding compound of formula (XII). One skilled in the art will recognize that the protecting groups $Pg^1$ and $Pg^2$ may be removed simultaneously or sequentially.

For example, wherein one or both of the protecting groups are protecting groups which may be removed under acid conditions, for example, BOC, and the like, the compound of formula (VI) is reacted with an acid such as hydrochloric acid, hydrobromic acid, sulfuric acid, trifluoroacetic acid, and the like, in a polar solvent such as acetone, THF, DCM, and the like.

Alternatively, wherein one or both of the protecting groups are protecting groups which may be removed under hydrogenation conditions, for example, CBz, and the like, the compound of formula (IV) is subjected to catalytic hydrogenation. More particularly, the compound of formula (IV) is treated with a reducing agent such as $H_2$ gas, preferably hydrogen gas at a pressure of about 1 to about 70 psi, preferably about 50 psi, in the presence of a catalyst such as 10% Pd on carbon, Pt on carbon, and the like, in an organic solvent such as ethanol, methanol, and the like.

Alternatively still, wherein one or more of the protecting groups are protecting groups which may be removed under acid conditions, for example, Fmoc, and the like, the compound of formula (IV) is subjected to basic cleavage. More particularly, the compound of formula (IV) is reacted with a base such as piperidine, morpholine, dicyclohexylamine, and the like, in an organic solvent such as, THF, DMF, and the like.

The compound of formula (XII) is reacted with a suitably substituted compound of formula (VIII), wherein A' represents an activated form of the A substituent, a known compound or compound prepared by known methods; in a polar solvent such as water, DMF, sulfolane, and the like; preferably, the temperature of the reaction is maintained in the range of about −20° C. to about 15° C., more preferably the temperature of the reaction is maintained in the range of about −5 to about 5° C.; to yield the corresponding compound of formula (I).

One skilled in the art will recognize, that the process outlined in Scheme 3 above may alternatively be applied to a compound of formula (IV) wherein the guanidine portion is bis-protected, i.e. a compound of formula (XIII)

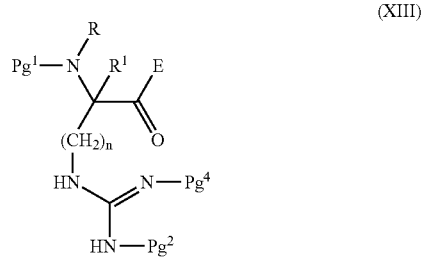

(XIII)

wherein $Pg^4$ is a suitably nitrogen protecting group, and wherein $Pg^4$ is the same as $Pg^2$. In the process outlined in Scheme 3 above, wherein the compound of formula (XIII) is substituted for the compound of formula (IV), the deprotection removes the $Pg^1$, $Pg^2$ and $Pg^4$ groups to yield the corresponding compound of formula (XII) which is then reacted to yield the corresponding compound of formula (I).

The compound of formula (I) is preferably isolated by known methods, for example by recrystallization or column chromatography.

Alternatively, the compound of formula (I) may be reacted with a suitable acid, to yield the corresponding salt, preferably a pharmaceutically acceptable salt, which in turn may be optionally further purified by known methods, for example by recrystallization.

The compound of formula (III), wherein all variables are as defined above, is a known compound or compound prepared by known methods. For example, the compound of formula (III) may be prepared according to the process as outlined in Scheme 4.

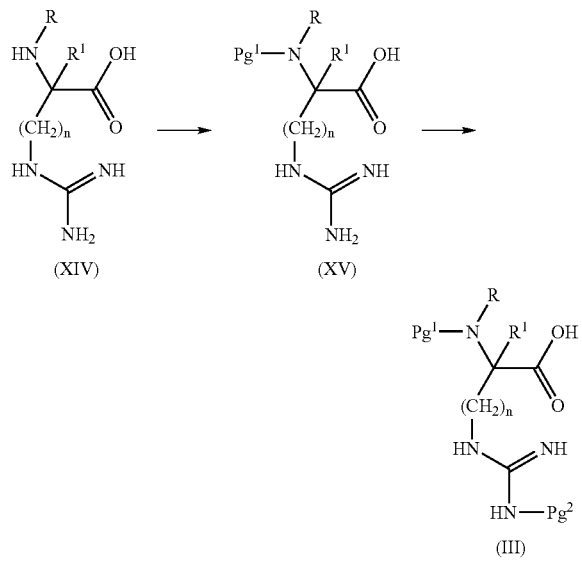

Scheme 4

Accordingly, a suitably substituted compound of formula (XIV), a known compound or compound prepared by known methods, is reacted with a first suitable nitrogen protecting reagent, to yield the corresponding compound of formula (XV). For example, the compound of formula (XIV) may be reacted with a first nitrogen protecting reagent selected form the group consisting of Boc anhydride and CBz-Cl, to yield the corresponding compound of formula (XV) wherein $Pg^1$ is BOC and CBz, respectively.

The compound of formula (XV) is reacted with a second suitable nitrogen protecting reagent, to yield the corresponding compound of formula (III). For example, the compound of formula (XV) may be reacted with a second nitrogen protecting reagent selected form the group consisting of BOC anhydride, CBz-Cl, Mtr-Cl and tosyl chloride, to yield the corresponding compound of formula (III) wherein $Pg^2$ is BOC, CBz, MTr and p-toluene sulfonyl, respectively.

In the preparation of the compound of formula (III), the protecting groups $Pg^1$ and $Pg^2$ (and thus the corresponding nitrogen protecting reagents) are selected such that the protecting group $Pg^1$ may be removed under conditions which do not remove the protecting group $Pg^2$.

One skilled in the art will further recognize that the compound of formula (XV) may be reacted with greater than or equal to about 2 equivalents of the second nitrogen protecting group to yield the corresponding bis-protected compound of formula (X), wherein $Pg^2$ and $Pg^4$ are the same.

The compound of formula (V) is a known compound or compound prepared by known methods, for example, according to the process outlined in Scheme 5.

Scheme 5

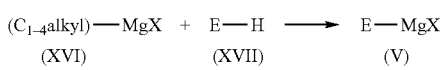

Accordingly, a suitably substituted compound of formula (XVI), a known compound or compound prepared by known methods, wherein the $C_{1-4}$alkyl group is preferably t-butyl, is reacted with a suitably substituted compound of formula (XVII), a known compound or compound prepared by known methods, in an anhydrous organic solvent which is inert to the compound of formula (XVI) and inert to the compound of formula (V), such as THF, glyme, MTBE, and the like, preferably THF; to yield the corresponding compound of formula (V).

Wherein the compound of formula (V) E is benzothiazole and X is $Cl$, the compound of formula (V) may be prepared according to known methods, according to the process described by Yuan et al., in *Acta Chimica Sinica—Chinese Edition—Huaxue Xuebao*, 48(9), (1990), pp 931–935.

The compound of formula (VIII) is a known compound or compound prepared by known methods. For example, the compound of formula (VIII) may be prepared by reacting the carboxylic acid derivative of the substituent A (e.g. a compound of the formula A—OH) with a suitable activating agent.

For example, the carboxylic acid derivative of the substituent A, a compound of the formula A—OH may be reacted with CDI (i.e. the activating agent) in an anhydrous, aprotic organic solvent such as THF, dioxane, ethyl acetate, and the like, to yield the corresponding compound A', wherein A' is a compound of the formula A-imidazolyl.

Alternatively, the carboxylic acid derivative of the substituent A, a compound of the formula A—OH may be reacted with isobutylchloroformate; in the presence of an organic base, preferably in the presence of a tertiary amine base such as diisopropylethylamine, N-methylmorpholine, and the like, in an anhydrous, aprotic organic solvent such as THF, dioxane, MTBE, and the like, preferably at a temperature in the range of about −20 to about 15° C., to yield the corresponding compound A', wherein A' is a mixed anhydride, a compound of the formula A—O—C(O)—O-isobutyl.

Other suitable activating agents and reactions may be found in texts such as Bodansky, Miklos, *Principles of Peptide Synthesis*, 2nd Edition, Springer-Verlag, 1993.

In an embodiment of the present invention, is a process for the preparation of the compound of formula (IIa), as outlined in Scheme 6.

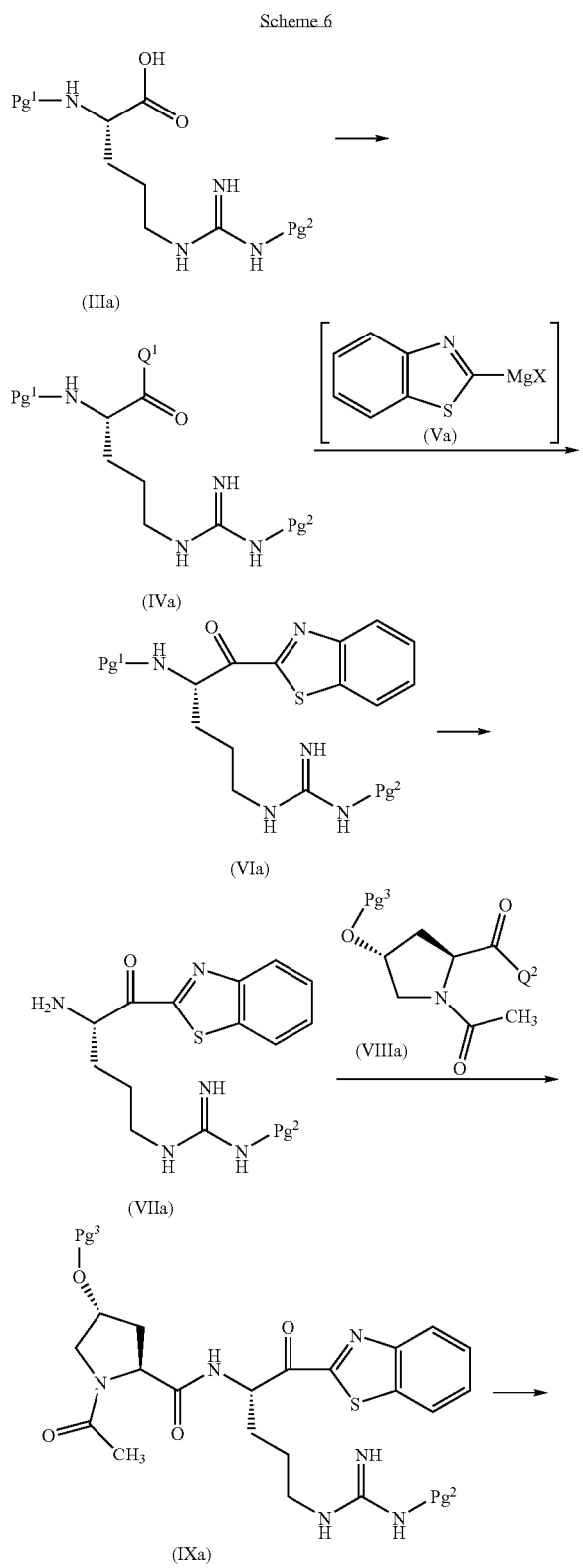

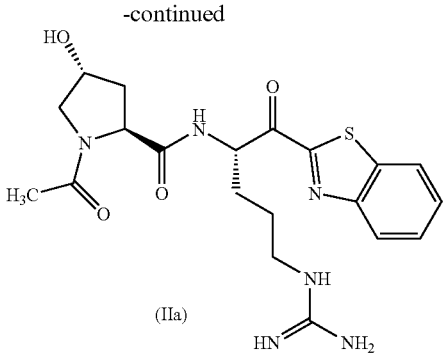

Accordingly, a suitably substituted compound of formula (IIIa), wherein $Pg^1$ is a first suitable nitrogen protecting group such as t-butoxycarbonyl (BOC), benzyloxycarbonyl (CBz), N-(9-fluorenylmethoxycarbonyl) (Fmoc) and the like, preferably BOC; and $Pg^2$ is a second suitable nitrogen protecting group such as 4-methoxy-2,3,6-trimethyl-phenyl-sulfonyl (MTr), benzyloxycarbonyl (CBz), p-toluene-sulfonyl, t-butoxycarbonyl (BOC) and the like, preferably MTr; and wherein $Pg^1$ and $Pg^2$ are selected such that the $Pg^1$ protecting group may be removed under conditions which do not remove the $Pg^2$ protecting group, a known compound or compound prepared by known methods; is reacted to activate the carboxylic acid portion of the compound of formula (IIIa), by reacting the compound of formula (IIIa) with a suitable activating agent, preferably under anhydrous conditions, to yield the corresponding compound of formula (IVa), an activated form of the compound of formula (IIIa), wherein $Q^1$ is a leaving group, preferably $Q^1$ is imidazolyl.

One skilled in the art will recognize that when the compound of formula (IVa) is not isolated prior to the next step, the activation of the compound of formula (IIIa) to the corresponding compound of formula (IVa) is preferably completed under anhydrous conditions.

For example, the compound of formula (IIIa) may be reacted with CDI in an aprotic organic solvent such as THF, dioxane, ethyl acetate, and the like, to yield the corresponding compound of formula (IVa) wherein $Q^1$ is imidazolyl.

Alternatively, the compound of formula (IIIa) may be reacted with isobutylchloroformate, in the presence of an organic base, preferably in the presence of a tertiary amine base such as diisopropylethylamine, N-methylmorpholine, triethylamine, pyridine, and the like, in a chlorinated solvent such as DCE, DCM, and the like, at a temperature in the range of about −20 to about 10° C., followed by addition of N,O-dimethylhydroxyamine HCl salt and a tertiary amine base such as diisopropylethylamine, N-methylmorpholine, and the like, to yield the corresponding compound of formula (IVa) wherein $Q^1$ is —$N(CH_3)(OCH_3)$.

Alternatively still, the compound of formula (IIIa) may be reacted with $Ph_2POCl$, in the presence of an organic base, preferably in the presence of a tertiary amine base such as TEA, DIPEA, pyridine, and the like, in an anhydrous, aprotic organic solvent such as THF, dioxane, MTBE, DCM, DCE, and the like, preferably at a temperature in the range of about −20 to about 15° C., to yield the corresponding compound of formula (IVa) wherein $Q^1$ is —O—$POPh_2$.

The compound of formula (IVa) is reacted with a solution or suspension of a suitably substituted compound of formula (Va), wherein X is selected from the group consisting of Cl, Br and I; preferably Cl or Br, more preferably Cl; in an anhydrous organic solvent which is inert to the compound of formula (Va) (i.e. in an anhydrous organic solvent which does not react with the compound of formula (Va)) such as THF, diethyl ether, glyme, MTBE, and the like; preferably the anhydrous organic solvent which is inert to the compound of formula (Va) is the solvent in which the compound of formula (IVa) was prepared; preferably, the compound of formula (IVa) is added to the compound of formula (Va); preferably, the temperature of the reaction is maintained in the range of about −20° C. to about 15° C., more preferably the temperature of the reaction is maintained in the range of about −10 to about 5° C., to yield the corresponding compound of formula (VIa).

The compound of formula (VIa) is subjected to selective de-protection, to yield the corresponding compound of formula (VIIa).

For example, wherein $Pg^1$ is a nitrogen protecting group which may be removed under acid conditions, such as BOC, the compound of formula (VIa) is reacted with an acid such as hydrochloric acid, hydrobromic acid, sulfuric acid, trifluoroacetic acid (TFA), and the like, preferably hydrochloric acid, in an organic solvent such as methanol, ethyl acetate, glyme, THF, and the like, or a mixture thereof, preferably a mixture of methanol and ethyl acetate, to yield the corresponding compound of formula (VIIa) as the acid addition salt.

Alternatively, wherein $Pg^1$ is a nitrogen protecting group which may be removed under catalytic hydrogenation conditions, such as CBz, the compound of formula (VIa) is reacted with hydrogen gas, in the presence of a catalytic amount of a catalyst such as Pd on carbon, and the like, in the presence of an acid such as hydrochloric acid, sulfuric acid, trifluoroacetic acid, and the like, to yield the corresponding compound of formula (VIIa). One skilled in the art will recognize that when the hydrogenation is completed in the presence of an acid, the de-protection yields the corresponding compound of formula (VIIa) as the acid addition salt.

Alternatively still, wherein $Pg^1$ is a nitrogen protecting group which may be removed under basic conditions, such as Fmoc, the compound of formula (VIa) is reacted with a secondary amine base such as piperidine, morpholine, dicyclohexylamine, and the like, preferably piperidine, in an organic solvent such as ethyl acetate, glyme, THF, and the like, to yield the corresponding compound of formula (VIIa).

Preferably, $Pg^1$ is a nitrogen protecting group which may be removed under acidic conditions or under catalytic hydrogenation conditions.

Preferably, the compound of formula (VIa) is de-protected under conditions which yield the corresponding compound of formula (VIIa) as an acid addition salt. Preferably the compound of formula (VIIa) is isolated according to known methods, more preferably, the compound of formula (VIIa) is isolated as an acid addition salt.

One skilled in the art will recognize that the compound of formula (VIIa), in the form of the free amine, is not stable over time. Therefore, it is preferred that the compound of formula (VIIa), as the free amine, is reacted in the next step within a short period of time, e.g. before significant degradation.

Preferably, wherein $Pg^1$ is a nitrogen protecting group which may be removed under basic conditions, the compound of formula (VIIa) is isolated as an acid addition salt, according to known methods (e.g. by reacting with a suitable acid such as HCl).

The compound of formula (VIIa) is reacted with a suitably substituted compound of formula (VIIIa), wherein $Pg^3$ is a suitable oxygen protecting group such as t-butyl-dimethylsilyl, benzyl, MOM, and the like; preferably t-butyl-dimethylsilyl; and wherein $Q^2$ is a leaving group such as —O—C(O)—O-isobutyl, imidazolyl, and the like, preferably $Q^2$ is —O—C(O)—O-isobutyl; in the presence of a tertiary amine base such as DIPEA, TEA, N-methylmorpholine, and the like; in an aprotic organic solvent such as acetonitrile, ethyl acetate, MTBE, THF, and the like, preferably acetonitrile or THF; preferably under anhydrous conditions; preferably, the compound of formula (VIIa) is added to the compound of formula (VIIIa); preferably, the temperature of the reaction is maintained in the range of about −20° C. to about 15° C., more preferably the temperature of the reaction is maintained in the range of about −5 to about 5° C.; to yield the corresponding compound of formula (IXa).

The compound of formula (IXa) is subjected to de-protection to remove the $Pg^2$ and $Pg^3$ protecting groups, according to known methods, to yield the corresponding compound of formula (IIa).

Alternatively, the compound of formula (VIIa) may be reacted with a compound of formula (VIIIb)

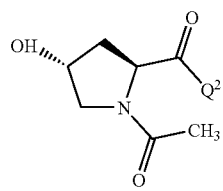

(VIIIb)

wherein $Q^2$ is a leaving group, such as —O—C(O)—O-isobutyl, imidazolyl, and the like, preferably $Q^2$ is —O—C(O)—O-isobutyl, a known compound or compound prepared by known methods; an aprotic organic solvent such as acetonitrile, ethyl acetate, MTBE, THF, and the like; preferably under anhydrous conditions; preferably in acetonitrile or water; preferably, the compound of formula (VIIa) is added to the compound of formula (VIIIb); wherein the temperature of the reaction is maintained in the range of about −20° C. to about 15° C.; to yield the corresponding compound of formula (IXc)

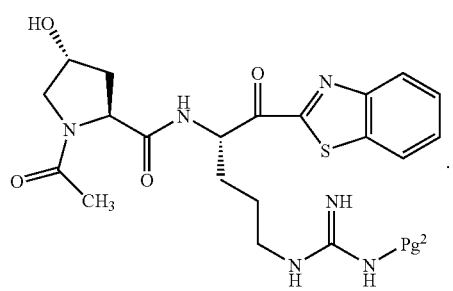

(IXc)

The compound of formula (IXc) is then subjected to de-protection to remove the $Pg^2$ protecting group according to known methods, to yield the corresponding compound of formula (IIa).

The present invention is further directed to a process for the preparation of the compound of formula (IIa), as outlined in Scheme 7.

Scheme 7

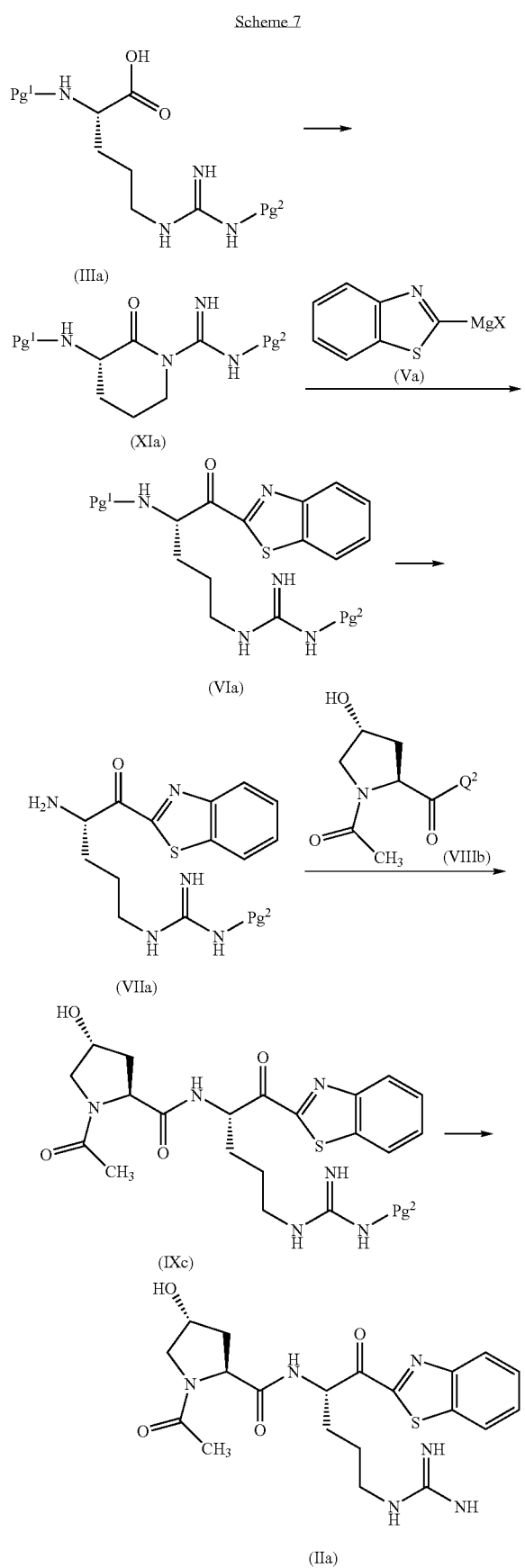

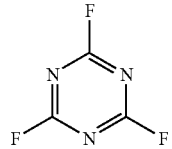

Accordingly, a suitably substituted compound of formula (IIIa), wherein $Pg^1$ is a first suitable nitrogen protecting group such as t-butoxycarbonyl (BOC), benzyloxycarbonyl (CBZ), N-(9-fluorenylmethoxycarbonyl) (Fmoc) and the like, preferably BOC; and $Pg^2$ is a second suitably nitrogen protecting group such as 4-methoxy-2,3,6-trimethyl-phenyl-sulfonyl (MTr), benzyloxycarbonyl (CBz), p-toluene-sulfonyl, t-butoxycarbonyl (BOC) and the like, preferably CBz; and wherein $Pg^1$ and $Pg^2$ are selected such that the $Pg^1$ protecting group may be removed under conditions which do not remove the $Pg^2$ protecting group; a known compound or compound prepared by known methods; is reacted with an activating agent capable of cyclizing the compound of formula (IIIa), such as isobutylchloroformate, $SOCl_2$, (2,4,6-trifluoro-[1,3,5]triazine), and the like, to yield the corresponding compound of formula (XIa).

For example the compound of formula (IIIa) is reacted with isobutylchloroformate, a known compound, in an organic solvent such as THF, diethyl ether, glyme, MTBE, ethyl acetate, methylene chloride, and the like; or a mixture of an organic solvent and water, such as a 1:1 mixture of THF:water, and the like; in the presence of an organic amine base, preferably a tertiary amine base such as TEA, DIPEA, pyridine, and the like; preferably at a temperature in the range of about −15 to about 10° C., more preferably at a temperature in the range of −5 and 5° C.; to yield the corresponding compound of formula (XIa).

Alternatively, the compound of formula (IIIa) is reacted with $SOCl_2$, in an aprotic organic solvent which is inert to the compound of formula (IIIa) such as DCM. DCE, toluene, and the like, preferably at a temperature in the range of about −20 to about 15° C., more preferably at a temperature in the range of about −5 to about 5° C., to yield the corresponding compound of formula (XIa).

Alternatively still, the compound of formula (IIIa) is reacted with 2,4,6-trifluoro-[1,3,5]triazine (also known as cyanuric fluoride), in an aprotic organic solvent which is inert to the compound of formula (IIIa) such as DCM. DCE, toluene, and the like, preferably at a temperature in the range of about −20 to about 15° C., more preferably at a temperature in the range of about −5 to about 5° C., to yield the corresponding compound of formula (XIa).

The compound of formula (XIa) is reacted with a solution or suspension of a suitably substituted compound of formula (Va), wherein X is selected from the group consisting of Cl, Br and I; preferably Cl or Br, more preferably Cl, a known compound or compound prepared by known methods; in an anhydrous organic solvent which is inert to the compound of formula (Va) (i.e. in an anhydrous organic solvent which does not react with the compound of formula (Va)) such as THF, diethyl ether, glyme, MTBE, and the like; preferably the anhydrous organic solvent which is inert to the compound of formula (Va) is the solvent in which the compound of formula (XIa) was prepared; preferably, the compound of formula (XIa) is added to the compound of formula (Va); preferably, the temperature of the reaction is maintained in the range of about −20° C. to about 15° C., more preferably the temperature of the reaction is maintained in the range of about −10 to about 0° C., more preferably still, the temperature of the reaction is maintained in the range of about −10 to about −5° C.; to yield the corresponding compound of formula (VIa).

The compound of formula (VIa) is subjected to selective de-protection, to yield the corresponding compound of formula (VIIa).

For example, wherein $Pg^1$ is a nitrogen protecting group which may be removed under acid conditions, such as BOC, the compound of formula (VIa) is reacted with an acid such as hydrochloric acid, hydrobromic acid, sulfuric acid, trifluoroacetic acid (TFA), and the like, preferably hydrochloric acid, in an organic solvent such as methanol, ethyl acetate, glyme, THF, and the like, or a mixture thereof, preferably a mixture of methanol and ethyl acetate, to yield the corresponding compound of formula (VIIa) as the acid addition salt.

Alternatively, wherein $Pg^1$ is a nitrogen protecting group which may be removed under catalytic hydrogenation conditions, such as CBz, the compound of formula (VIa) is reacted with hydrogen gas, in the presence of a catalytic amount of a catalyst such as Pd on carbon, and the like, in the presence of an acid such as hydrochloric acid, sulfuric acid, trifluoroacetic acid, and the like, to yield the corresponding compound of formula (VIIa). One skilled in the art will recognize that when the hydrogenation is completed in the presence of an acid, the de-protection yields the corresponding compound of formula (VIIa) as the acid addition salt.

Alternatively still, wherein $Pg^1$ is a nitrogen protecting group which may be removed under basic conditions, such as Fmoc, the compound of formula (VIa) is reacted with a secondary amine base such as piperidine, morpholine, dicyclohexylamine, and the like, preferably piperidine, in an organic solvent such as ethyl acetate, glyme, THF, and the like, to yield the corresponding compound of formula (VIIa).

Preferably, pg1 is a nitrogen protecting group which may be removed under acidic conditions or under catalytic hydrogenation conditions.

Preferably, the compound of formula (VIa) is de-protected under conditions which yield the corresponding compound of formula (VIIa) as an acid addition salt. Preferably the compound of formula (VIIa) is isolated according to known methods, more preferably, the compound of formula (VIIa) is isolated as an acid addition salt.

One skilled in the art will recognize that the compound of formula (VIIa), in the form of the free amine, is not stable over time. Therefore, it is preferred that the compound of formula (VIIa), as the free amine, is reacted in the next step within a short period of time, e.g. before significant degradation.

Preferably, wherein $Pg^1$ is a nitrogen protecting group which may be removed under basic conditions, the compound of formula (VIIa) is isolated as an acid addition salt, according to known methods (e.g. by reacting with a suitable acid such as HCl).

The compound of formula (VIIa) is reacted with a compound of formula (VIIIb), wherein $Q^2$ is a leaving group such as —O—C(O)—O-isobutyl, imidazolyl, and the like, preferably $Q^2$ is —O—C(O)—O-isobutyl, a known compound or compound prepared by known methods; in an aprotic organic solvent such as acetonitrile, ethyl acetate, MTBE, THF, and the like, preferably acetonitrile or THF; preferably under anhydrous conditions; preferably, the compound of formula (VIIIb) is added to the compound of formula (VIIa); preferably, the temperature of the reaction is maintained in the range of about −20° C. to about 15° C., more preferably the temperature of the reaction is maintained in the range of about −15 to about 0° C.; to yield the corresponding compound of formula (IXc).

One skilled in the art will recognize that in the compound of formula (VIIIb), it may be desirable to protect the hydroxy group, with a suitable oxygen protecting group. Suitable protecting groups include, but are not limited to silyl containing protecting group such as t-butyl-dimethyl-silyl, and the like; a benzyl group; a MOM group; and the like. Preferably, the protecting group is t-butyl-dimethyl-silyl.

The compound of formula (IXc) is subjected to de-protection to remove the $Pg^2$ protecting group (and wherein the compound of formula (VIIIb) is protected, the oxygen protecting group) according to known methods, to yield the corresponding compound of formula (IIa).

The compound of formula (IIa) is preferably isolated by known methods, for example by column chromatography, by crystallization, by recrystallization, and the like.

Alternatively, the compound of formula (IIa) may be reacted with a suitable acid such as hydrochloric, trifluoroacetic, nitric, sulfuric, and the like, in an organic solvent or mixture thereof such as methanol, acetonitrile, ethanol, 1-butanol, acetone, IPA, THF, methanol/IPA, methanol/THF, and the like, to form the corresponding acid addition salt of the compound of formula (IIa).

The present invention is further directed to a nitrate or sulfate salt of the compound of formula (IIa). In an embodiment of the present invention is a crystalline nitrate or sulfate salt of the compound of formula (IIa).

The single crystal X-ray structure was determined by Crystalytics Company (Lincoln, Nebr.). Single yellowish-orange crystals of the sulfate salt of the compound of formula (IIa) were obtained as thin plates from $H_2O$/isopropanol (dimensions: 0.09 mm×0.33 mm×0.46 mm) and were, at −80±2° C., monoclinic, space group $P2_1$–$C_2^2$ (No. 4) with a=10.653 (1) Å, b=10.425 (1) Å, c=11.448 (1) Å, β=108.897 (2)°, V=1202.8 (2) Å$^3$ and Z=2 {$d_{calcd}$=1.504 g-cm$^{-3}$; $\mu_a$ (MoK$_\alpha$)=0.281 mm$^{-1}$}. A full hemisphere of diffracted intensities (ω-scan width of 0.30°) was measured by using graphite-monochromated MoKα radiation (from a normal-focus sealed X-ray tube operated at 50 kV and 40 mA) on a Bruker Single Crystal SMART CCD Area Detector Diffraction System. Lattice constants were determined with the Bruker SAINT software package using peak centers for 3134 reflections. A total of 7805 integrated reflection intensities having 2θ (MoKα. <57.470° were produced using the Bruker program SAINT. Of these, 5101 reflections were unique and gave $R_{int}$=0.036. The Bruker SHELXTL-PC software package was used to solve the structure using "direct methods" techniques. All stages of weighted full-matrix lest-squares refinement were conducted using $F_o^2$ data with the SHELTX-PC software package. Final agreement factors at convergence are: $R_1$ (unweighted, based on F)=0.051 for 3661 independent reflections have 2θ (MoKα) <57.47° and I>26(I); $R_1$ (unweighted, based on F)=0.082 and $wR_2$ (weighted, based on F$^2$)=0.120 for all 5101 independent reflections having 2° (MoKα)<57.470.

The structural model incorporated anisotropic thermal parameters for all nonhydrogen atoms and isotropic thermal parameters for all hydrogen atoms. Hydrogen atoms bonded to oxygen and nitrogen were located from a difference Fourier synthesis and included in the structural model as independent isotropic atoms. The methyl group was refined as a rigid rotor (using idealized sp$^3$-hybridized geometry and a C—H bond length of 0.96 Å) with three rotational parameters in least-squares cycles. The final refined values of these three rotational parameters gave C—C—H angles that ranged from 103° to 119°. The remaining hydrogen atoms were included in the structural model as fixed atoms (using idealized sp$^2$- or sp$^3$-hybridized geometry and C—H bond lengths of 0.95–1.00 Å) "riding" on their respective carbons. The isotropic thermal parameters for hydrogen atoms were fixed at values 1.2 (non-methyl) or 1.5 (methyl) times the equivalent isotropic thermal parameters of the carbon atoms to which they are covalently bonded.

The present invention is further directed to a sulfate salt of the compound of formula (IIa) characterized by the atomic positions, bond lengths and bond angles as determined by single crystal X-ray structure and as listed in Tables 1–4 below. The atoms are numbered according to the solid state structure as drawn in FIG. 1.

TABLE 1

Atomic Coordinates for Nonhydrogen Atoms[a]

| atom type[b] | Fractional Coordinates | | | Equivalent isotropic thermal parameter U, Å$^2$ × 10$^{3c}$ |
|---|---|---|---|---|
| | 10$^4$x | 10$^4$y | 10$^4$z | |
| CATION | | | | |
| $S_1$ | −1078 (1) | 5001 (1) | 2277 (1) | 36 (1) |
| $O_1$ | 1773 (2) | 4953 (3) | 3045 (2) | 39 (1) |
| $O_2$ | 1921 (2) | 79 (2) | 3306 (2) | 38 (1) |
| $O_3$ | −1619 (2) | −2154 (3) | 322 (2) | 34 (1) |
| $O_4$ | 3950 (2) | −799 (3) | 1904 (3) | 40 (1) |
| $N_1$ | 9332 (3) | 1103 (4) | 4794 (3) | 41 (1) |
| $N_2$ | 7183 (3) | 1702 (3) | 4553 (3) | 35 (1) |
| $N_3$ | 8910 (4) | 3070 (4) | 5444 (3) | 44 (1) |
| $N_4$ | −681 (3) | 2536 (3) | 2261 (3) | 34 (1) |
| $N_5$ | 2040 (3) | 1847 (3) | 2198 (3) | 24 (1) |
| $N_6$ | 1859 (3) | −1470 (3) | 1269 (3) | 31 (1) |
| $C_1$ | 8474 (3) | 1960 (4) | 4928 (3) | 32 (1) |
| $C_2$ | 6175 (3) | 2667 (4) | 4485 (3) | 37 (1) |
| $C_3$ | 4792 (3) | 2107 (3) | 3998 (3) | 32 (1) |
| $C_4$ | 3770 (3) | 3197 (4) | 3653 (3) | 30 (1) |
| $C_5$ | 2337 (3) | 2725 (3) | 3242 (3) | 24 (1) |
| $C_6$ | 1380 (3) | 3857 (4) | 2941 (3) | 28 (1) |
| $C_7$ | −75 (3) | 3639 (3) | 2503 (3) | 27 (1) |
| $C_8$ | −2454 (3) | 4019 (4) | 1790 (3) | 33 (1) |
| $C_9$ | −2057 (4) | 2730 (4) | 1849 (3) | 36 (1) |
| $C_{10}$ | −2998 (4) | 1752 (5) | 1506 (4) | 48 (1) |
| $C_{11}$ | −4323 (4) | 2106 (5) | 1098 (4) | 55 (1) |
| $C_{12}$ | −4697 (4) | 3389 (6) | 1031 (4) | 57 (1) |
| $C_{13}$ | −3792 (4) | 4374 (5) | 1366 (4) | 46 (1) |
| $C_{14}$ | 1824 (3) | 598 (3) | 2317 (3) | 28 (1) |
| $C_{15}$ | 1382 (3) | −132 (3) | 1104 (3) | 28 (1) |
| $C_{16}$ | −136 (3) | −299 (3) | 640 (3) | 29 (1) |
| $C_{17}$ | −386 (3) | −1622 (3) | 1071 (3) | 28 (1) |
| $C_{18}$ | 774 (3) | −2410 (4) | 987 (4) | 32 (1) |
| $C_{19}$ | 3160 (4) | −1711 (4) | 1694 (3) | 34 (1) |
| $C_{20}$ | 3603 (4) | −3081 (4) | 1895 (4) | 45 (1) |
| ANION | | | | |
| $S_2$ | 7295 (1) | −1876 (1) | 3101 (1) | 42 (1) |
| $O_5$ | 6261 (3) | −993 (4) | 3355 (3) | 56 (1) |
| $O_6$ | 8439 (4) | −1077 (5) | 3356 (5) | 139 (3) |
| $O_7$ | 7584 (8) | −2855 (5) | 3943 (4) | 178 (3) |
| $O_8$ | 6858 (3) | −2291 (3) | 1847 (2) | 54 (1) |

[a]The numbers in parentheses are the estimated standard deviations in the last significant digit.
[b]Atoms are labeled in agreement with FIG. 1.
[c]This is one-third of the trace of the orthogonalized $U_{ij}$ tensor.

TABLE 2

Atomic Coordinates for Hydrogen Atoms[d]

| atom type[e] | Fractional Coordinates | | |
|---|---|---|---|
| | 10$^4$x | 10$^4$y | 10$^4$z |
| CATION | | | |
| $H_{30}$[f] | −1977 (35) | −2220 (36) | 829 (32) |
| $H_{1N1}$[f] | 9041 (41) | 412 (47) | 4365 (40) |
| $H_{1N2}$[f] | 10110 (49) | 1221 (49) | 5073 (42) |
| $H_{2N}$[f] | 6891 (37) | 1033 (41) | 4180 (34) |
| $H_{3N1}$[f] | 9812 (47) | 3317 (44) | 5666 (38) |
| $H_{3N2}$[f] | 8443 (42) | 3622 (46) | 5636 (39) |
| $H_{5N}$[f] | 1954 (31) | 2087 (31) | 1450 (32) |
| $H_{2a}$ | 6260 | 3373 | 3937 |
| $H_{2b}$ | 6319 | 3029 | 5318 |
| $H_{3a}$ | 4625 | 1555 | 4635 |
| $H_{3b}$ | 4709 | 1572 | 3262 |
| $H_{4a}$ | 3918 | 3769 | 4376 |
| $H_{4b}$ | 3913 | 3709 | 2978 |
| $H_5$ | 2200 | 2250 | 3949 |
| $H_{10}$ | −2741 | 876 | 1550 |
| $H_{11}$ | −4987 | 1461 | 861 |
| $H_{12}$ | −5616 | 3593 | 741 |
| $H_{13}$ | −4061 | 5246 | 1312 |
| $H_{15}$ | 1687 | 314 | 470 |
| $H_{16a}$ | −566 | 369 | 994 |
| $H_{16b}$ | −486 | −241 | −272 |
| $H_{17}$ | −366 | −1578 | 1950 |
| $H_{18a}$ | 982 | −3118 | 1597 |
| $H_{18b}$ | 591 | −2773 | 149 |
| $H_{20a}$ | 4553 | −3061 | 2115 |
| $H_{20b}$ | 3360 | −3327 | 2601 |
| $H_{20c}$ | 3250 | −3691 | 1242 |
| ANION | | | |
| $H_{50}$[f] | 5458 (52) | −1073 (58) | 2835 (46) |

[d]Hydrogen atoms bonded to oxygen and nitrogen ($H_{30}$, $H_{50}$, $H_{1N1}$, $H_{1N2}$, $H_{2N}$, $H_{3N1}$, $H_{3N2}$, and $H_{5N}$) were located from a difference Fourier synthesis and included in the structural model as independent isotropic atoms. The methyl group ($C_{20}$ and its hydrogens) was refined as a rigid rotor (using idealized sp$^3$-hybridized geometry and a C—H bond length of 0.96 Å) with three rotational parameters in least-squares cycles. The final refined values of these three rotational parameters gave C—C—H angles which ranged from 103° to 119°. The remaining hydrogen atoms were included in the structural model as fixed atoms (using idealized sp$^2$- or sp$^3$-hybridized geometry andC—H bond lengths of 0.95–1.00 Å) "riding" on their respective carbons. The isotropic thermal parameters for $H_{30}$, $H_{50}$, $H_{1N1}$, $H_{1N2}$, $H_{2N}$, $H_{3N1}$, $H_{3N2}$, and $H_{5N}$ refined to final $U_{iso}$ values of 0.02(1), 0.08(2), 0.05(1), 0.05(1), 0.03(1), 0.06(1), 0.05(1), and 0.02(1) Å$^2$, respectively. The isotropic thermal parameters of the remaining hydrogen atoms were fixed at values 1.2 (nonmethyl) or 1.5 (methyl) times the equivalent isotropic thermal parameters of the carbonatoms to which they are covalently bonded.
[e]Hydrogen atoms which are covalently bonded to carbon are labeled with the same numerical subscripts as their carbon atoms, with an additional literal subscript (a, b or c), where necessary, to distinguish between hydrogens bonded to the same carbon atom.Hydrogen atoms bonded to oxygen and nitrogen are labeled with the same numerical subscript as their oxygen or nitrogen, a literal subscripted O or N, and an additional subscripted 1 or 2, where necessary, to distinguish between hydrogens bonded to the same nitrogen.
[f]The numbers in parentheses are the estimated standard deviations in the last significant digit.

TABLE 3

Bond Lengths[g]

| bond type[h] | length, Å | bond type[h] | length, Å |
|---|---|---|---|
| CATION | | | |
| $S_1$—$C_7$ | 1.745 (4) | $N_2$—$C_2$ | 1.454 (5) |
| $S_1$—$C_8$ | 1.726 (4) | $N_4$—$C_9$ | 1.401 (5) |
| | | $N_5$—$C_5$ | 1.456 (4) |

TABLE 3-continued

Bond Lengths[g]

| bond type[h] | length, Å | bond type[h] | length, Å |
|---|---|---|---|
| $O_1$—$C_6$ | 1.210 (4) | $N_6$—$C_{18}$ | 1.470 (4) |
| $O_2$—$C_{14}$ | 1.228 (4) | $N_6$—$C_{15}$ | 1.476 (5) |
| $O_4$—$C_{19}$ | 1.241 (4) | | |
| | | $C_2$—$C_3$ | 1.513 (5) |
| $O_3$—$C_{17}$ | 1.428 (4) | $C_3$—$C_4$ | 1.534 (5) |
| $O_3$—$H_{3O}$ | 0.79 (3) | $C_4$—$C_5$ | 1.526 (5) |
| | | $C_5$—$C_6$ | 1.524 (5) |
| $N_1$—$C_1$ | 1.323 (5) | $C_{15}$—$C_{16}$ | 1.540 (5) |
| $N_2$—$C_1$ | 1.329 (5) | $C_{16}$—$C_{17}$ | 1.517 (5) |
| $N_3$—$C_1$ | 1.314 (5) | $C_{17}$—$C_{18}$ | 1.513 (5) |
| $N_4$—$C_7$ | 1.304 (5) | | |
| $N_5$—$C_{14}$ | 1.338 (4) | $C_6$—$C_7$ | 1.485 (5) |
| $N_6$—$C_{19}$ | 1.335 (5) | $C_{14}$—$C_{15}$ | 1.518 (5) |
| | | $C_{19}$—$C_{20}$ | 1.499 (5) |
| $N_1$—$H_{1N1}$ | 0.87 (5) | | |
| $N_1$—$H_{1N2}$ | 0.80 (5) | $C_8$—$C_{13}$ | 1.398 (5) |
| $N_2$—$H_{2N}$ | 0.82 (4) | $C_8$—$C_9$ | 1.403 (6) |
| $N_3$—$H_{3N2}$ | 0.83 (5) | $C_9$—$C_{10}$ | 1.394 (6) |
| $N_3$—$H_{3N1}$ | 0.95 (5) | $C_{10}$—$C_{11}$ | 1.385 (6) |
| $N_5$—$H_{5N}$ | 0.87 (3) | $C_{11}$—$C_{12}$ | 1.390 (7) |
| | | $C_{12}$—$C_{13}$ | 1.375 (7) |
| ANION | | | |
| $S_2$—$O_5$ | 1.535 (3) | $S_2$—$O_6$ | 1.426 (4) |
| | | $S_2$—$O_7$ | 1.368 (4) |
| $O_5$—$H_{5O}$ | 0.87 (5) | $S_2$—$O_8$ | 1.425 (3) |

[g]The numbers in parentheses are the estimated standard deviations in the last significant digit.
[h]Atoms are labeled in agreement with FIG. 1.

TABLE 4

Bond Angles[j]

| angle type[k] | angle, (deg) | angle type[k] | angle, (deg) |
|---|---|---|---|
| CATION | | | |
| $C_8S_1C_7$ | 88.9 (2) | $O_1C_6C_5$ | 121.6 (3) |
| $C_7N_4C_9$ | 109.6 (3) | $O_1C_6C_7$ | 117.9 (3) |
| | | $C_7C_6C_5$ | 120.5 (3) |
| $N_1C_1N_2$ | 120.5 (4) | $N_4C_7S_1$ | 116.7 (3) |
| $N_3C_1N_1$ | 119.3 (4) | $C_6C_7S_1$ | 116.6 (3) |
| $N_3C_1N_2$ | 120.1 (4) | $N_4C_7C_6$ | 126.7 (3) |
| $C_1N_2C_2$ | 123.1 (3) | $C_{13}C_8S_1$ | 128.2 (4) |
| $C_1N_1H_{1N1}$ | 119 (3) | $C_{13}C_8C_9$ | 121.8 (4) |
| $C_1N_1H_{1N2}$ | 121 (4) | $N_4C_9C_8$ | 114.9 (3) |
| $H_{1N1}N_1H_{1N2}$ | 119 (5) | $C_{10}C_9N_4$ | 124.6 (4) |
| $C_1N_2H_{2N}$ | 121 (3) | $C_{10}C_9C_8$ | 120.6 (4) |
| $C_2N_2H_{2N}$ | 114 (3) | $C_{11}C_{10}C_9$ | 117.5 (5) |
| $C_1N_3H_{3N1}$ | 123 (3) | $C_{10}C_{11}C_{12}$ | 121.2 (4) |
| $C_1N_3H_{3N2}$ | 125 (3) | $C_{13}C_{12}C_{11}$ | 122.7 (4) |
| $H_{3N2}N_3H_{3N1}$ | 112 (4) | $C_{12}C_{13}C_8$ | 116.3 (4) |
| $C_{17}O_3H_{3O}$ | 99 (3) | $O_2C_{14}N_5$ | 123.8 (3) |
| | | $O_2C_{14}C_{15}$ | 122.1 (3) |
| $C_{14}N_5C_5$ | 121.8 (3) | $N_5C_{14}C_{15}$ | 114.0 (3) |
| $C_5N_5H_{5N}$ | 124 (2) | $O_4C_{19}N_6$ | 119.1 (3) |
| $C_{14}N_5H_{5N}$ | 114 (2) | $O_4C_{19}C_{20}$ | 122.7 (3) |
| $C_{18}N_6C_{15}$ | 112.9 (3) | $N_6C_{19}C_{20}$ | 118.2 (3) |
| $C_{19}N_6C_{15}$ | 119.8 (3) | | |
| $C_{19}N_6C_{18}$ | 127.2 (3) | $N_6C_{15}C_{14}$ | 111.4 (3) |
| | | $N_6C_{15}C_{16}$ | 102.5 (3) |
| $N_2C_2C_3$ | 111.5 (3) | $C_{14}C_{15}C_{16}$ | 110.6 (3) |
| $C_2C_3C_4$ | 109.5 (3) | $C_{17}C_{16}C_{15}$ | 105.4 (3) |
| $C_5C_4C_3$ | 113.3 (3) | $O_3C_{17}C_{16}$ | 112.4 (3) |
| $N_5C_5C_4$ | 112.7 (3) | $O_3C_{17}C_{18}$ | 111.2 (3) |
| $N_5C_5C_6$ | 110.5 (3) | $C_{18}C_{17}C_{16}$ | 103.9 (3) |
| $C_6C_5C_4$ | 110.5 (3) | $N_6C_{18}C_{17}$ | 103.0 (3) |
| $C_9C_8S_1$ | 109.9 (3) | | |

TABLE 4-continued

Bond Angles[j]

| angle type[k] | angle, (deg) | angle type[k] | angle, (deg) |
|---|---|---|---|
| ANION | | | |
| $O_6S_2O_5$ | 103.2 (2) | $O_8S_2O_6$ | 111.2 (3) |
| $O_7S_2O_5$ | 109.0 (3) | $O_7S_2O_8$ | 114.1 (3) |
| $O_8S_2O_5$ | 110.7 (2) | | |
| $O_7S_2O_6$ | 108.0 (4) | $S_2O_5H_{5O}$ | 115 (4) |

[j]The numbers in parentheses are the estimated standard deviations in the last significant digit.
[k]Atoms are labeled in agreement with FIG. 1.

The present invention is further directed to a sulfate salt of the compound of formula (IIa) comprising the following X-ray diffraction peaks:

TABLE 5

X-Ray Diffraction Pattern, Sulfate Salt

| Position (°2θ) | d-spacing (Å) | Relative Intensity (%) |
|---|---|---|
| 8.718 | 10.144 | 32.15 |
| 11.736 | 7.541 | 8.59 |
| 12.155 | 7.282 | 5.52 |
| 12.920 | 6.852 | 42.47 |
| 13.795 | 6.419 | 7.67 |
| 16.328 | 5.429 | 28.67 |
| 16.688 | 5.313 | 14.53 |
| 16.933 | 5.236 | 50.11 |
| 17.509 | 5.065 | 15.13 |
| 17.900 | 4.956 | 16.95 |
| 18.744 | 4.734 | 7.28 |
| 18.852 | 4.707 | 6.79 |
| 19.087 | 5.398 | 6.61 |
| 19.579 | 4.534 | 9.74 |
| 21.391 | 4.154 | 4.95 |
| 21.915 | 4.056 | 7.46 |
| 22.655 | 3.925 | 8.02 |
| 23.296 | 3.819 | 14.21 |
| 23.616 | 3.767 | 10.81 |
| 24.752 | 3.597 | 100.00 |
| 26.094 | 3.415 | 6.04 |
| 26.346 | 3.383 | 4.66 |
| 26.839 | 3.322 | 5.28 |
| 27.054 | 3.296 | 7.23 |
| 27.413 | 3.254 | 3.94 |
| 27.772 | 3.212 | 8.41 |
| 28.398 | 3.143 | 2.51 |
| 28.848 | 3.095 | 3.01 |
| 29.135 | 3.065 | 2.48 |
| 30.072 | 2.972 | 2.80 |
| 30.664 | 2.916 | 3.68 |
| 31.220 | 2.865 | 13.61 |
| 31.843 | 2.810 | 1.37 |
| 32.421 | 2.762 | 3.89 |
| 32.643 | 2.743 | 4.35 |
| 33.662 | 2.663 | 2.43 |
| 34.196 | 2.622 | 2.94 |
| 34.862 | 2.574 | 5.22 |

In an embodiment of the present invention is a crystalline sulfate salt of the compound of formula (IIa) comprising XRD peaks as listed in Table 5, wherein the peaks have a measured peak intensity of greater than or equal to about 10%.

The present invention is further directed to a nitrate salt of the compound of formula (IIa) comprising the following X-ray diffraction peaks:

TABLE 6

| X-Ray Diffraction Pattern, Nitrate Salt | | |
|---|---|---|
| Position (°2θ) | d-spacing (Å) | Relative Intensity (%) |
| 3.0923 | 28.5717 | 1.88 |
| 3.3292 | 26.5392 | 1.94 |
| 3.4458 | 25.6421 | 3.64 |
| 4.4707 | 19.7656 | 1.29 |
| 5.0793 | 17.3985 | 0.49 |
| 5.8742 | 15.0458 | 0.42 |
| 8.1393 | 10.8630 | 19.41 |
| 8.5028 | 10.3994 | 4.39 |
| 9.9822 | 8.8612 | 21.85 |
| 11.4205 | 7.7483 | 11.01 |
| 12.6056 | 7.0224 | 18.01 |
| 14.7390 | 6.0104 | 100.00 |
| 15.3862 | 5.7590 | 3.90 |
| 16.5158 | 5.3676 | 25.50 |
| 17.4104 | 5.0937 | 9.51 |
| 18.3459 | 4.8360 | 11.28 |
| 18.9361 | 4.6866 | 45.55 |
| 19.7319 | 4.4994 | 12.06 |
| 20.1146 | 4.4146 | 11.77 |
| 20.9453 | 4.2414 | 66.50 |
| 21.6840 | 4.0985 | 4.61 |
| 22.3001 | 3.9867 | 17.47 |
| 23.5479 | 3.7782 | 29.73 |
| 24.0340 | 3.7028 | 49.70 |
| 24.8049 | 3.5895 | 24.39 |
| 25.2993 | 3.5204 | 23.05 |
| 26.0528 | 3.4203 | 11.69 |
| 27.1754 | 3.2815 | 19.01 |
| 28.1124 | 3.1742 | 15.33 |
| 29.1864 | 3.0598 | 6.31 |
| 29.6919 | 3.0089 | 6.45 |
| 30.2053 | 2.9589 | 3.86 |
| 30.7701 | 2.9059 | 6.70 |
| 31.1020 | 2.8756 | 10.74 |
| 32.1021 | 2.7883 | 11.27 |
| 33.3334 | 2.6880 | 8.15 |
| 34.1781 | 2.6235 | 5.12 |

In an embodiment of the present invention is a crystalline nitrate salt of the compound of formula (IIa) comprising the XRD peaks as listed in Table 6, wherein the peaks have a measured peak intensity of greater than or equal to about 10%.

The X-ray diffraction pattern with peaks as listed in Tables 5 and 6 above were obtained as follows. The sample was backloaded into a conventional X-ray Diffraction (XRD) holder. The sample was scanned from 3 to 35° 2θ at a step size of 0.0165° 2θ and a time per step of 10.16 seconds. The effective scan speed was 0.2067°/s. Instrument voltage and current settings of 45 kV and 40 mA were employed.

The present invention is further directed to a process for the preparation of a sulfate salt of the compound of formula (II)

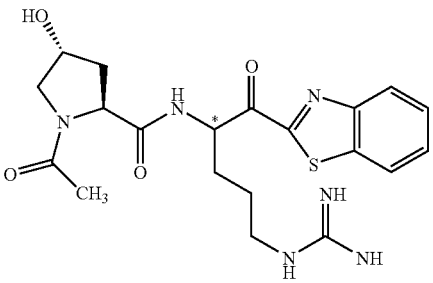

wherein the (1S) diastereomer predominates comprising (a) treating a solution comprising an acid addition salt, preferably a pharmaceutically acceptable acid addition salt, of the compound of formula (II) and water or a polar organic solvent or mixture thereof; with a weakly basic ion-exchange resin; wherein the weakly basic ion-exchange resin is present in amount greater than or equal to about 1 equivalent relative to the acid of the acid addition salt; to yield the corresponding compound of formula (II);

(b) reacting the compound of formula (II) with sulfuric acid; wherein the sulfuric acid is present in an amount equal to about 1 molar equivalent relative to the amount of the compound of formula (II); to yield the corresponding sulfate salt of the compound of formula (II), wherein the (1S) diastereomer predominates.

The present invention is further directed to a process for the preparation of a crystalline nitrate or sulfate salt of the compound of formula (IIa).

A nitrate salt of the compound of formula (IIa) may be prepared by reacting the compound of formula (IIa) or an acid addition salt of the compound of formula (IIa) such as a trifluoroacetic acid addition salt, hydrobromic acid addition salt, hydrochloric acid addition salt, and the like; wherein the acid addition salt of the compound of formula (IIa) is not a nitrate or sulfate salt of the compound of formula (IIa); with nitric acid, in an organic solvent or mixture thereof such as methanol, ethanol, IPA, and the like, followed by addition of an anti-solvent such as acetonitrile, acetone, THF, and the like, as necessary, to yield the corresponding nitrate salt of the compound of formula (IIa).

A sulfate salt of the compound of formula (IIa) may be prepared by reacting the compound of formula (IIa) or an acid addition salt of the compound of formula (IIa); wherein the acid addition salt of the compound of formula (IIa) is not a sulfate salt of the compound of formula (IIa) such as a trifluoroacetic acid addition salt, hydrobromic acid addition salt, hydrochloric acid addition salt, nitric acid addition salt, and the like; with sulfuric acid, in an organic solvent or mixture thereof such as methanol, ethanol, IPA, and the like, followed by addition of an anti-solvent such as acetonitrile, acetone, THF, and the like, as necessary, to yield the corresponding nitrate salt of the compound of formula (IIa).

Preferably, the nitrate or sulfate salt of the compound of formula (IIa) is recrystallized according to known methods from an organic solvent or mixture thereof such as IPA/water, ethanol/water, butanol/water 1-propanol/water, and the like, preferably from a mixture of IPA/water.

Alternatively, a salt of the compound of formula (IIa), such as a hydrochloride salt, a trifluoroacetic acid salt, toluenesulfonic acid, nitric acid, sulfuric acid, and the like, is reacted with an ion exchange resin capable of neutralizing the salt of the compound of formula (IIa), such as a weakly basic anion-exchange resin, wherein the active group on such a weakly basic anion-exchange resin is a weak base such as dimethylamine, a tertiary amine, trimethylammonium, and the like, such as Dowex MWA-1, Dowex 66, Amberlyst A 21, Amberlite IRA-67, and the like; preferably a high capacity weakly basic anion-exchange resin; more preferably, Dowex 66; in a polar solvent or mixture thereof such as acetonitrile, ethanol, methanol, methanol/acetonitrile, methanol/IPA, methanol/THF, methanol/1-butanol, methanol/acetone, and the like, preferably in a polar solvent or mixture thereof in which the solubility of the compound of formula (IIa) is the highest, more preferably, methanol; to yield the free base of the compound of formula (II).

The above process will also result in epimerization of the compound of formula (IIa) to yield a mixture of the (1S) and (1R) diastereomers of the compound of formula (II).

The epimerized free base of the compound of formula (II) is reacted with an acid such as nitric acid, sulfuric acid, hydrochloric acid, trifluoroacetic acid, benzene sulfonic acid, and the like; preferably nitric or sulfuric acid; to yield the corresponding acid addition salt of the compound of formula (II). Preferably, the compound of formula (II) as a free base is reacted with an acid which selectively crystallizes the corresponding salt of the desired diastereomer of the compound of formula (IIa), more preferably the compound of formula (II) as a free base is reacted with nitric or sulfuric acid.

Preferably, the ion exchange resin capable of epimerizing the compound of formula (II) is selected to yield a mixture of diastereomers wherein the desired diastereomer is present in an amount greater than or equal to about 50%. Preferably, the desired diastereomers is present in an amount greater than or equal to 60%.

One skilled in the art will recognize that the undesired diastereomers of the compound of formula (II), the compound of formula (IIb)

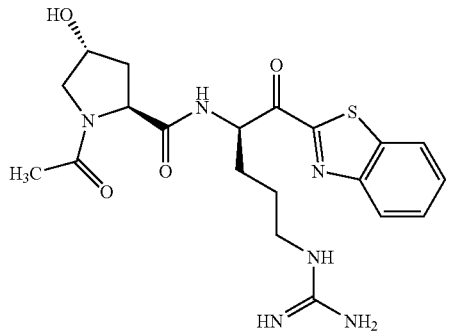

(IIb)

(which preferably remains in solution upon crystallization of the sulfate or nitrate salt of the desired diastereomer, the compound of formula (IIa)) may be further reacted according to the process described above (i.e. reacting with a suitable ion-exchange resin followed by reaction with an acid) to produce more of the sulfate or nitrate salt of the desired diatereomer, the compound of formula (IIa).

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral or an enatioselective HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following examples describe the invention in greater detail and are intended to illustrate the invention, but not to limit it.

EXAMPLE 1

[(3S)-1-(Benzyloxycarbonylamino-imino-methyl)-2-oxo-piperidin-3-yl]-carbamic Acid tert-butyl Ester

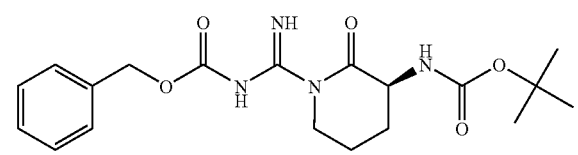

To a mixture of L-arginine (156 g), water (840 g) and tert-butanol (500 g) was added at 15° C. di-tert-butyl dicarbonate (225 g). The mixture was allowed to warm to 25° C. and then an aqueous sodium hydroxide solution (235 g, 30%-ww) was added to the reaction mixture. After stirring overnight, the mixture was cooled to −5° C. An aqueous sodium hydroxide solution (810 g, 30%-ww) and subsequent benzyl chloroformate (483.3 g) were added. The aqueous phase was discarded and a solution of potassium hydroxide (25 g) in methanol (270 g) was added to the organic phase. The mixture was stirred at ambient temperature for 5 hours. The reaction mixture was hydrolyzed with water (500 g) and a saturated aqueous sodium chloride solution (500 g). The water phase was discarded. To the organic phase were added a 1:1 mixture of tetrahydrofuran and water (900 g) and subsequently at 0° C. triethylamine (135.5 g). Isobutyl chloroformate (182 g) was then added to the reaction mixture, at a rate such that the temperature did not exceed 10° C. After completion of the cyclization reaction, the mixture was allowed to heat to ambient temperature. The aqueous phase was discarded. To the organic phase were added water (200 g) and a saturated aqueous sodium chloride solution (300 g). The aqueous phase was discarded, the organic phase was cooled to 10° C. and to this mixture was added methanol (450 g). The reaction mixture was cooled to 0° C. After stirring at 0° C., the product was filtered and dried under reduced pressure to yield the title compound as colorless crystalline solid. The crude product was recrystallized from methanol.

M.P.: 160–163° C.;
MS: m/z=391 (M+1)+

EXAMPLE 2

(2S,4R)-1-Acetyl-N-[(1S)-1-(2-benzothiazolylcarbonyl)-4-[[imino[(benzyloxycarbonyl)amino]methyl]amino]butyl]-4-hydroxypyrrolidine-2-carboxamide

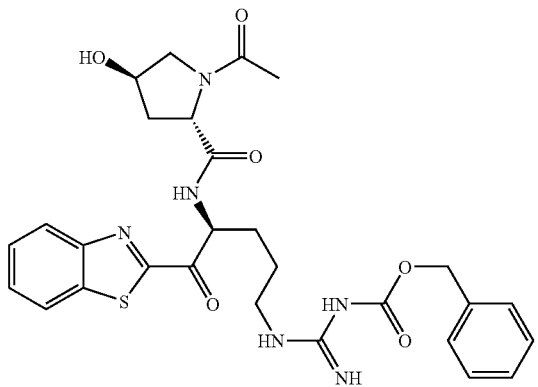

To a solution of tert-butylmagnesium chloride in tetrahydrofuran (1.6 M) (2200 g) was added benzothiazole (17.4 g) dropwise. The mixture was stirred for 40 min. A suspension of [(3S)-1-(benzyloxycarbonylamino-imino-methyl)-2-oxo-piperidin-3-yl]-carbamic acid tert-butyl ester (20 g) (prepared as in Example 1) in tetrahydrofuran (60 g) was added at –10° C. over about 15 min. The reaction mixture was maintained, with stirring at –10° C. for 2 hours. To the reaction mixture was then added a mixture of ice (160 g), concentrated hydrochloric acid (77 g) and ethyl acetate (120 g). The organic layer was washed twice with a 1:1 mixture of concentrated aqueous sodium chloride solution:2M hydrochloric acid. Subsequently the organic phase was treated with hydrogen chloride gas and a 3.5M solution of hydrogen chloride in 1,4-dioxane. The mixture was stirred at ambient temperature overnight. After completion of the debocylation step (i.e. removal of Boc group) the mixture was evaporated in vacuum to yield a resiude, which was suspended in acetonitrile (50 g).

In a separate reaction vessel, a mixture of N-acetyl-trans-4-hydroxy-L-proline (10.16 g), N-methylmorpholine (5.93 g) and acetonitrile (110 g) was cooled to –20° C. Over about 5 min isobutylchloroformate (8.15 g) was added and the reaction mixture was stirred for 30 min at –20° C. To this mixture were added the above prepared acetonitrile suspension and simultaneously N-methylmorpholine (10 g) at –20° C. After stirring at –15° C. for 30 min, the reaction mixture was quenched with 2M hydrochloric acid (200 g). The organic solvents were evaporated and the aqueous residue was treated with methanol (100 g). After stirring for 30 min the product was filtered and dried in vacuum at 40° C. to yield the title compound as colorless crystalline solid, which was recrystallized from a mixture of acetonitrile and 2M aqueous hydrochloric acid.

M.P.: 197° C.;
MS: m/z=581 (M+1)+

EXAMPLE 3

(2S, 4R)-1-Acetyl-N-[(1S)-1-(2-benzothiazolylcarbonyl)-4-[[imino(amino)methyl]-amino]butyl]-4-hydroxypyrrolidine-2-carboxamide

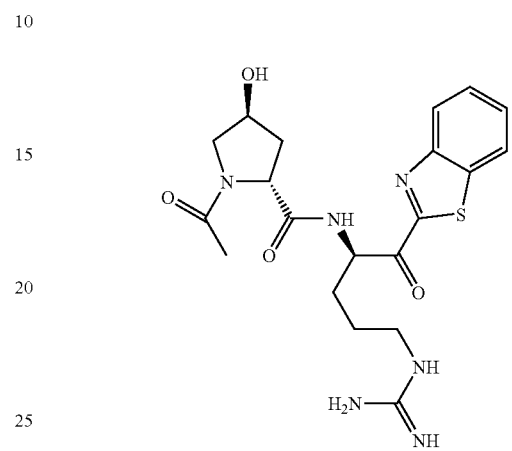

The title compound was obtained by stirring a solution of (2S, 4R)-1-acetyl-N-[(1S)-1-(2-benzothiazolylcarbonyl)-4-[[imino[(benzyloxycarbonyl)amino]methyl]amino]butyl]-4-hydroxypyrrolidine-2-carboxamide (prepared as in Example 2 above) in concentrated hydrobromic acid at 10° C. for 3 hours.

MS: m/z=447 (M+1)+

EXAMPLE 4

(4R)-1-Acetyl-4-[[(1,1-dimethylethyl)dimethylsilyl]oxy]-L-proline]

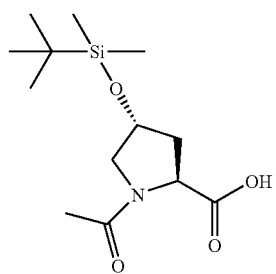

A 1 L 3-necked round bottom flask was flame dried and then cooled under nitrogen. To the RBF was added TBDM-SCl (93.1 g), which was dissolved into acetonitrile (350 mL). The solution was cooled to about 5–10° C. using an ice bath, yielding a suspension. To the reaction was then added N-Acetyl-L-hyroxyproline (50.0 g) and then DBU (92 mL), dropwise, while stirring the reaction at about 0–5° C. The reaction was observed to convert to a clear faint yellow solution. The solution was removed from the ice bath and let stir for 1 hour, then cooled to 0° C. using an ice bath. To the reaction was then added water (50 mL) and solution let stir for 25 minutes, over which time the solution was observed to change to an opaque suspension. The suspension was transferred to a 2 L flask. Water (2000 mL) was added, resulting in a thick suspension, the solution was filtered, and flask rinsed with additional water (400 mL). The filter cake was washed with AcN:H$_2$O (1:7, 2×500 mL) to yield a solid, which was air dried for 10 minutes and then dried overnight under vacuum at 40° C., to yield the title compound as a white powder

EXAMPLE 5

(2S)-2-[[(1,1-Dimethylethoxy)carbonyl]amino]-5-[[imino[[(4-methoxy-2,3,6-trimethylphenyl)sulfonyl]-amino]methyl]amino]pentanethioic acid, S-phenyl Ester

STEP A:

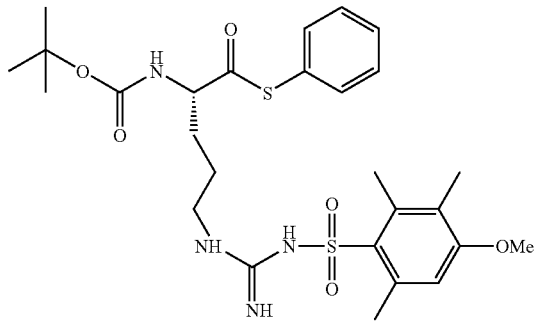

To a 1 L 3-necked round bottom flask were added Boc-Arg-Mtr-OH.MtBE (50 g) and then EtOAC (300 mL). The resulting suspension was stirred under argon and cooled to 0° C. using an ice bath. To the solution was then added Et$_3$N (26.7 mL) by syringe, resulting in a clear solution.

Step B:

In a separate reaction vessel Ph$_2$POCl (22. g) was dissolved in EtOAC (50.0 mL) and transferred to a 125 mL addition funnel. The solution was then added dropwise, while maintaining the reaction temperature between 0–5° C. to the solution prepared in Step A. The reaction mixture was then stirred at 0° C. for 30 minutes. To the reaction mixture was then added thiophenol (9.8 mL), via syringe, while maintaining the reaction temperature between 0–5° C. The reaction mixture was then stirred cold for 15 minutes and filtered over a pad of celite. The RBF was rinsed with EtOAC (3×20 mL) and the pad of celite washed with EtOAc (2×50 mL). The combined EtOAc washes were transferred to a 1 L separatory funnel, washed with 1N HCl (3×200 mL), NaHCO$_3$ (3×200 mL) gently with water (2×200 mL), and then saturated NaCl (1×200 mL). The organics were transferred to a 1 L Erlemeyer flask and dried over MgSO$_4$ for 30 minutes. The resulting solution was filtered over a pad of celite and the dried solution transferred to a 1-L RBF. The EtOAc solvent was removed in vacuo to yield an oil which was placed under high vacuum overnight to yield the title compound as a crude white foam.

Step C: Recrystallization

The crude foam was dissolved in toluene (260 mL). To the solution was then added methylcyclohexane (771 mL), dropwise with vigorous stirring. The product precitated as a white powder and produced a thick slurry. The slurry was vacuum filtered and the filter cake washed with methylcyclohexane (3×100 mL). The filter cake was dried overnight under vacuum at 40° C. to yield the title compound as a white powder.

EXAMPLE 6

[(1S)-1-(2-benzothiazolylcarbonyl)-4-[[imino[[(4-methoxy-2,3,6-trimethylphenyl)sulfonyl]amino]methyl]amino]butyl]-carbamic Acid 1,1-dimethylethyl Ester

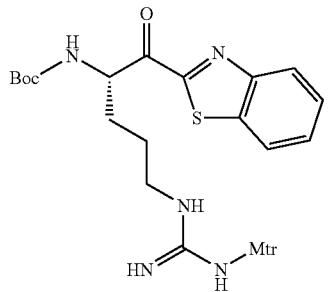

Step A:

To a slurry of 1,1'-carbonyldiimidazole (6.48 g, 40 mmol) in THF (23 mL) at room temperature was added as solution of Boc-Arg(Mtr)-OH (2-[(1,1-dimethylethoxy)carbonyl]-5-[imino[[(4-methoxy-2,3,6-trimethyl)phenyl]sulfonyl] amino]methyl]-L-ornithine) (18.00 g, 33.3 mmol) in THF (54 mL) via a cannula over 2 minutes. The gentle evolution of CO$_2$ was observed and the internal reaction temperature was observed to increase by 2° C. The resulting clear light yellow solution was stirred at room temperature for 5 minutes and then under slight vacuum for 30 minutes.

Step B:

In a separate reaction vessel, to a solution of CH$_3$CH$_2$—MgCl (200 mL, 400 mmol) in THF (100 mL) at 4° C. (cool water bath, 3–5° C.) was added a solution of benzothiazole (55.70 g, 400 mmol) in THF (100 mL), slowly over 2 h. The internal temperature was maintained at about 6–8° C. The resulting dark brown solution was stirred at 8° C. for 10 minutes.

Step C:

The solution from Step A was transferred into an addition funnel and added slowly into the solution from Step B over about 25 minutes. The internal reaction temperature was around 8–12° C. The resulting dark reddish solution was stirred at 10° C. for 15 minutes. The reaction mixture was then transferred into a cold (5–10° C.) mixture of 2M HCl solution (300 mL, 600 mmol) and EtOAC (150 mL) over 2 minutes with vigorous stirring. The internal temperature reached about 25° C. during the quench. After addition, the brown mixture was stirred for 5 minutes in a cool water bath (7–10° C.). The layers were separated and the aqueous layer was extracted with EtOAc (150 mL). The combined brownish organic layers were washed with a saturated NaHCO$_3$ solution (150 mL), water (150 mL) and brine (150 mL), then dried over MgSO$_4$ (20 g) for 2 h. After filtration and concentration of the solution to about 140 mL in vacuo, the crude mixture (some solid formed) was transferred to an addition funnel and the flask was rinsed with EtOAc (40 mL) to the total volume of 180 mL. The mixture was added in a steady stream to a mixture of heptane (600 mL) and EtOAc (60 mL) while stirring. After stirring for 15–30 minutes, the solid product was collected by vacuum filtration and washed with EtOAc/heptane (¼) (100 mL×3) and air-dried overnight (ca. 16 h) to yield the title compound as a tan solid.
MS: m/z=604 (M+H)+

EXAMPLE 7

N-[[[4-amino-5-(2-benzothiazolyl)-5-oxopentyl]amino]iminomethyl]-4-methoxy-2,3,6-trimethyl-benzenesulfonamide Dihydrochloride

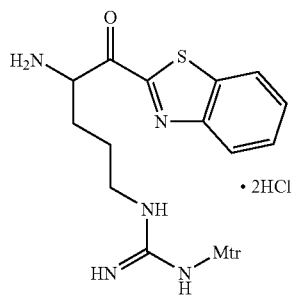

To a cold solution (15° C.) of THF (8 L) in a 12 L 4-necked round-bottomed flask (ice-water bath) was bubbled through HCl gas via two frit-tipped glass tubes and the internal temperature was raised to 25° C. The HCl gas flow rate was controlled to ensure the internal temperature did not exceed 25° C. After 4–5 h, the temperature was stabilized around 11° C. and the titration showed the concentration of HCl solution was 9M.

A 22 L 4-necked round-bottomed flask was charged with [(1S)-1-(2-benzothiazolylcarbonyl)-4-[[imino[[(4-methoxy-2,3,6-trimethylphenyl)sulfonyl]amino]methyl]amino]butyl]-carbamic acid 1,1-dimethylethyl ester, prepared in Example 6 (1.897 kg, 1.38 mol) and THF (2 L) was added. The thick suspension was stirred in a cooling bath (ice-water bath) and the internal temperature was around 20° C. Cold HCl/THF solution (11 L) was transferred into the suspension over 30 min. The suspension became a clear dark-brown solution and the internal temperature became 25–28° C. After 5 minutes, TLC and HPLC analysis showed a complete reaction. The reaction solution was purged with bubbled N₂ via two frit-tipped glass tubes at ambient temperature for 3 h.

The reaction solution was transferred to a 120 L reactor and cooled with chilled water. After the internal temperature reached below 8° C., MTBE (48 L) was added in a steady stream while the solution was stirred vigorously. After addition of MTBE, the internal temperature reached 12° C. and chilled water was removed. The yellow suspension was stirred at ambient temperature for 15 minutes. The stirring was stopped, the solid settled down and the top clear layer was siphoned out (about 20 L). Additional MTBE (24 L) was added and the suspension was stirred at ambient temperature for 15 minutes. The stirring was stopped, the solid settled down and the top clear layer was siphoned out (about 24 L). EtOAc (20 L) was added and the slurry was stirred at 50° C. for 15 minutes. After cooling down to 30° C., the solid was collected by vacuum filtration and washed with EtOAc (8 L). The resulting title product was obtained as a yellow solid and immediately dried in a vacuum oven at room temperature for 24 hours and 45° C. for 16 hours to yield the tile compound as a brown solid.
MS: m/z=504 (M+H)+

EXAMPLE 8

(2S,4R)-1-Acetyl-N-[1-(2-benzothiazolylcarbonyl)-4-[[imino[[(4-methoxy-2,3,6-trimethylphenyl)sulfonyl]amino]methyl]amino]butyl]-4-[[(1,1-dimethylethyl)dimethylsilyl]oxy]-2-pyrrolidinecarboxamide

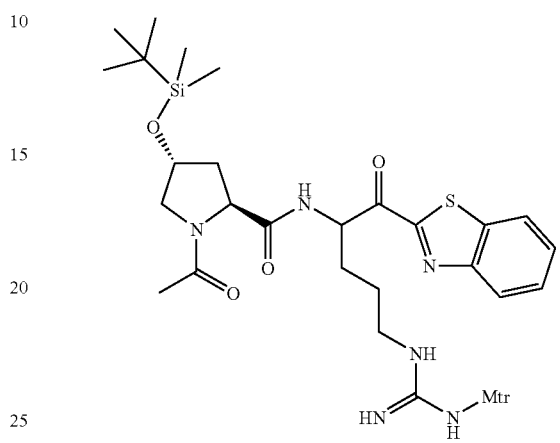

To a solution of (4R)-1-Acetyl-4-[[(1,1-dimethylethyl)dimethylsilyl]oxy]-L-proline], prepared as in Example 4 (81.15 g, 282.3 mmol) and NMM (56.5 mL, 513.7 mmol) in THF (1000 mL) at 0–5° C. (ice-water bath) was added a solution of isobutylchloroformate (36.6 mL, 282.3 mmol) in THF (200 mL), dropwise over 15 minutes. After addition, the white suspension was stirred at 0–5° C. for 30 minutes. Additional NMM (56.5 mL, 513.7 mmol) was added, followed by the portion-wise addition of the solid N-[[[4-amino-S-(2-benzothiazolyl)-5-oxopentyl]amino]iminomethyl]-4-methoxy-2,3,6-trimethyl-benzenesulfonamide dihydrochloride, prepared as in Example 7 (148.0 g, 256.6 mmol) over 10 minutes. The residual solid in the container and funnel was rinsed with THF (100 mL). The internal temperature reached 15° C. after addition. The brownish suspension was then stirred at 10–15° C. for 15 minutes. HPLC analysis indicated the completion of the reaction. The reaction mixture was quenched with a mixture of NH₄Cl saturated aqueous solution (400 mL) and water (200 mL). After separation of layers, the organic layer was washed with a mixture of NH₄Cl saturated aqueous solution (200 mL) and water (100 mL). The combined aqueous layer (pH=6.5) was extracted with EtOAc (200 mL). After separation of layers, the combined organic layer was washed with saturated NaHCO₃ solution (150 mL), water (2×150 mL) and then brine (150 mL). The combined H₂O and brine wash was back-extracted with EtOAc (200 mL). The combined organic layer was dried over MgSO₄ and the crude solution concentrated to near dryness. The crude oil was re-dissolved in EtOAc (800 mL), and transferred to an addition funnel. The flask was rinsed with EtOAc (50 mL) and combined into the addition funnel. The EtOAc solution was slowly added to a vigorously stirred heptane solution (3500 mL) over 30 minutes. The resulting light orange suspension was stirred at room temperature for 15 minutes. The solid was collected by a vacuum filtration, washed with heptane (500 mL) and air-dried for 24 h to yield the title compound as a light brown solid.
MS: m/z=773 (M+H)+

EXAMPLE 9

(2S,4R)-1-Acetyl-N-[(1S)-1-(2-benzothiazolylcarbonyl)-4-[[imino(amino)methyl]amino]butyl]-4-hydroxypyrrolidine-2-carboxamide

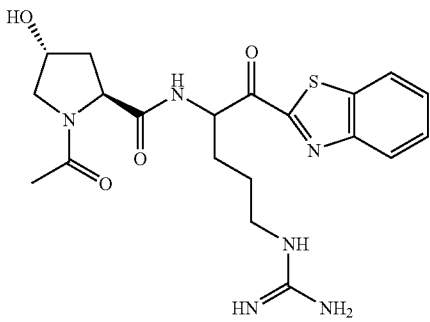

To a suspension of (2S, 4R)-1-acetyl-N-[(1S)-1-(2-benzothiazolylcarbonyl)-4-[[imino(amino)methyl]-amino]butyl]-4-hydroxypyrrolidine-2-carboxamide, the compound prepared as in Example 8 (26.00 g) in m-cresol (39 mL) and water (13 mL) was slowly added TFA (208 mL) at room temperature. After addition, the brownish solution was stirred at 50° C. for 1.5 hours. HPLC analysis of the reaction mixture showed the completion of the reaction. The volatiles were removed under reduced pressure and the crude residue was diluted with MeOH (20 mL). The crude solution was slowly added to a stirred MTBE solution (1500 mL) room temperature. The resulting beige suspension was stirred at room temperature for 30 minutes. After the solid settled down, the top clear yellow solution (about 1000 mL) was siphoned off and another, fresh solution of MTBE (1000 mL) was added. The suspension was stirred for 15 minutes. The solid was collected by vacuum filtration, washed with MTBE (200 mL) and then dried in vacuum oven at room temperature for 16 hours to yield the title product as a brown solid.

MS: m/z=447 (M+H)$^+$

EXAMPLE 10

(2s,4R)-1-Acetyl-N-[(1s)-1-(2-benzothiazolylcarbonyl)-4-[[imino(amino)methyl]amino]butyl]-4-hydroxypyrrolidine-2-carboxamide nitrate Salt

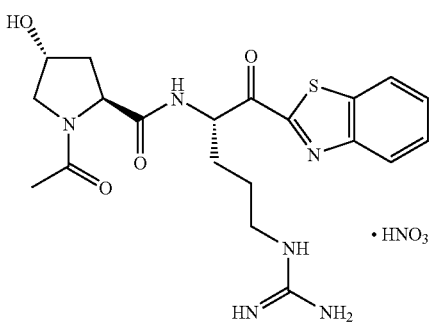

To a solution of the TFA salt of the single diastereomer (2S,4R)-1-acetyl-N-[(1S)-1-(2-benzothiazolylcarbonyl)-4-[[imino(amino)methyl]amino]butyl]-4-hydroxypyrrolidine-2-carboxamide (0.30 g, 0.493 mmol) in acetonitrile (4 mL) was added the solution of nitric acid (43.7 mg, 0.493 mmol) in acetonitrile (1 mL). A suspension formed upon mixing. The suspension was heated to partially dissolve the solid and then cooled to precipitate the title compound as a solid. The solid nitrate salt was filtered and dried in a vacuum oven at 30° C.

mp: 175–179° C.

Elemental Analysis: $C_{20}H_{26}N_6O_4S.1HNO_3.0.2H_2O$

| Calc.: | C46.78, H6.09, N19.10, S6.25, |
| --- | --- |
| | KF = 0.79% |
| Meas.: | C46.92, H5.40, N19.14, S6.20, F0.35, |
| | KF = 0.81% |

EXAMPLE 11

(2S,4R)-1-Acetyl-N-[(1s)-1-(2-benzothiazolylcarbonyl)-4-[[imino(amino)methyl]amino)butyl]-4-hydroxypyrrolidine-2-carboxamide Sulfate Salt

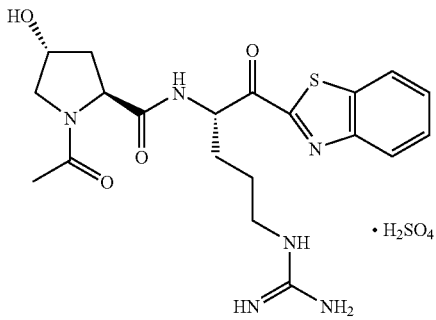

To a solution of the TFA salt of the single diastereomer (2S,4R)-1-Acetyl-N-[(1S)-1-(2-benzothiazolylcarbonyl)-4-[[imino(amino)methyl]amino]butyl]-4-hydroxypyrrolidine-2-carboxamide (0.30 g, 0.493 mmol) in acetonitrile (4 mL) was added a solution of sulfuric acid (48.3 mg, 0.493 mmol) in acetonitrile (1 mL). A suspension formed upon mixing. The suspension was heated to partially dissolve the solid, then cooled to precipitate the title compound as a solid. The solid was filtered and dried in a vacuum oven at 30° C.

m.p.: 214–216° C.

Elemental Analysis: $C_{20}H_{26}N_6O_4S.1H_2SO_4.0.29H_2O$

| Calc.: | C43.69, H5.24, N15.29, S11.67, |
| --- | --- |
| | KF = 0.96% |
| Meas.: | C44.18, H5.32, N15.22, S10.73, F1.15, |
| | KF = 0.96% |

EXAMPLE 12

(2S,4R)-1-Acetyl-N-[(1S)-4-[(aminoiminomethyl)amino]-1-(2-benzothiazolylcarbonyl)butyl]-4-hydroxy-2-pyrrolidinecarboxamide Sulfate Salt

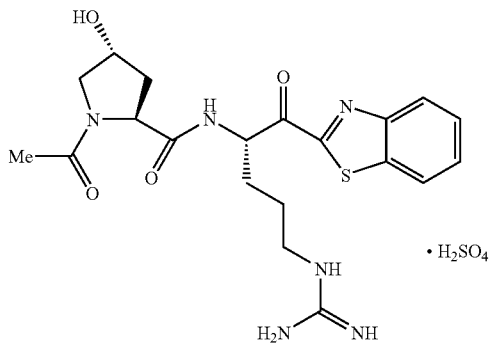

(2S,4R)-1-Acetyl-N-[(1S)-1-(2-benzothiazolylcarbonyl)-4-[[imino(amino)methyl]-amino]butyl]-4-hydroxypyrrolidine-2-carboxamide, the compound prepared as in Example 8, (700 g, 0.638 mol), THF (4000 ml), m-cresol (2000 ml) and anisole (35 ml) were charged to a 12 L 3-necked glass reaction flask equipped with mechanical stirrer, condenser, thermocouple, 1000 ml addition funnel and nitrogen inlet. To the reaction mixture was then added sulfuric acid (700 ml, 12.6 mol) from the addition funnel at the rate which maintained the temperature below 60° C. (total addition time was about 1 hour). After the addition, the reaction was heated to 60° C. and completed after 6 hrs, as determined by HPLC monitoring. Methanol (350 ml) was added to the reaction and heating was continued at 60° C. for 1 hour. The reaction mixture (diastereomeric ratio=30:70) was allowed to stand at room temperature over night.

Distilled water (5500 ml) was added to the reaction, followed by ethyl acetate (7500 ml). The layers were allowed to separate for 30 minutes. The separated organic layer was extracted with distilled water (2000 ml). The combined aqueous layers (diastereomeric ratio=32:68) were washed once with ethyl acetate (2000 ml).

Dowex 66 resin (9.8 Kg) was washed 3 times with distilled water (9000 ml). The damp resin was then added to the above water solution. The reaction mixture was stirred for 45 minutes and the pH reached pH 1.6. The solution was removed from the resin through a gas dispersion tube under reduced pressure. The resin was washed 3 times with distilled water/MeOH (5:1) (4600 ml). The combined cloudy solution was then filtered through a filter paper to remove particles. The resulting solution (diastereomeric ratio=33:67) was concentrated to glassy oil under reduced pressure at about 45–55° C.

$1^{st}$ Crop Crystallization:

The residual oil (prepared as above) was dissolved in warm MeOH (1500 mL). One equivalent of $H_2SO_4$ (61 g, 0.6 mol) was added to the solution. The MeOH solvent was removed (about 900 mL) under reduced pressure until about 750 g of the solution was left. To the solution was then added acetonitrile (750 mL) to adjust the solution to the cloud point. The solution was then seeded with the title compound (prepared as in Example 11). The reaction mixture was stirred at room temperature. After 4 days, the diastereomeric ratio of the filtrate was 68:31. Additional acetonitrile (150 mL) was added dropwise. After 2 more days stirring at room temperature, the diastereomeric ratio of the filtrate was 80:20. The solid was filtered and washed with MeOH/acetonitrle (1:1) (400 mL), then dried in a vacuum oven at 60° C. overnight to yield the title product as a light yellow solid.

mp 205–207° C.

diastereomeric ratio of isolated solid: 1.9:98.1

Original attempts to obtain a $2^{nd}$ crop by epimerization of the mother liquor of the $1^{st}$ crop were unsuccessful. However, attempts on the $1^{st}$ crop mother liquors of subsequent batches using chromatography proved successful in obtaining $2^{nd}$ and $3^{rd}$ crops. Below is described the procedure used on the 1st crop mother liquor from a separate synthesis.

EXAMPLE 13

Epimerization and Crystallization of Sulfate Salt ($2^{nd}$ Crop)

To the mother liquor of a $1^{st}$ crop from the preparation of (2S,4R)-1-Acetyl-N-[(1S)-4-[(aminoiminomethyl)amino]-1-(2-benzothiazolylcarbonyl)butyl]-4-hydroxy-2-pyrrolidinecarboxamide sulfate salt was added Dowex 66 resin until the pH of the solution reached about pH 7.2 to 7.6. The resin suspension was stirred overnight and the diastereomeric ratio reached equilibrium at about 44:56. The solution was removed from resin through a gas dispersion tube. The resin was then washed 4 times with MeOH. The combined solution was filtered and concentrated to dryness under reduced pressure at 25° C. for chromatography. The material was purified by reverse phase chromatography to yield fractions containing a diasteromeric mixture of (2S,4R)-1-Acetyl-N-[(1R)-4-[(aminoiminomethyl)amino]-1-(2-benzothiazolylcarbonyl)butyl]-4-hydroxy-2-pyrrolidinecarboxamide and (2S,4R)-1-Acetyl-N-[(1S)-4-[(aminoiminomethyl)amino]-1-(2-benzothiazolylcarbonyl)butyl]-4-hydroxy-2-pyrrolidinecarboxamide.

The combined fractions from the chromatography (2.95 L) containing a mixture of (2S,4R)-1-Acetyl-N-[(1R)-4-[(aminoiminomethyl)amino]-1-(2-benzothiazolylcarbonyl)butyl]-4-hydroxy-2-pyrrolidinecarboxamide and (2S,4R)-1-Acetyl-N-[(1S)-4-[(aminoiminomethyl)amino]-1-(2-benzothiazolylcarbonyl)butyl]-4-hydroxy-2-pyrrolidinecarboxamide as free base at a diastereomeric ratio 44:56 was concentrated to dryness to yield an oil. The oil was dissolved into MeOH (40 mL).

In a separate reaction vessel, $H_2SO_4$ (3.4 g, 0.0344 mol, approx. 1.2 mole eq.) was dissolved into acetonitrile (30 mL) and then added into the above MeOH solution with stirring. The solution started to turn cloudy during the addition. Additional acetonitrile (15 mL) was added to the true cloudy point, followed by addition of seeds of the sulfate salt of (2S,4R)-1-Acetyl-N-[(1S)-4-[(aminoiminomethyl)amino]-1-(2-benzothiazolylcarbonyl)butyl]-4-hydroxy-2-pyrrolidinecarboxamide. Solid was observed to precipitate out with stirring and the stirring was continued for 4 hours. The solid ($2^{nd}$ crop) was filtered and washed with AcN/MeOH (same ratio as in the mother liquor) (25 mL), then dried in a vacuum oven at 60° C. overnight to yield the sulfate salt of (2S,4R)-1-Acetyl-N-[(1S)-4-[(aminoiminomethyl)amino]-1-(2-benzothiazolylcarbonyl)butyl]-4-hydroxy-2-pyrrolidinecarboxamide as a light yellow solid.

diastereomeric ratio:5:95

EXAMPLE 14

[(3S)-1-(Benzyloxycarbonylamino-imino-methyl)-2-oxo-piperidin-3-yl]-carbamic Acid tert-butyl Ester

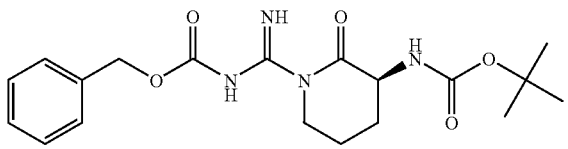

To a mixture of L-arginine (156 g), water (840 g) and tert-butanol (500 g) was added at 15° C. di-tert-butyl dicarbonate (225 g). The mixture was allowed to warm to 25° C. and an aqueous sodium hydroxide solution (30%-ww, 235 g) was added at this temperature. After stirring overnight, the mixture was cooled to –5° C. An aqueous sodium hydroxide solution (30%-ww, 810 g) and benzyl chloroformate (483.3 g) were then added in sequence. The aqueous phase was discarded and a solution of potassium hydroxide (25 g) in methanol (270 g) was added to the organic phase. The mixture was stirred at ambient temperature for 5 hours. The reaction mixture was then hydrolyzed with water (500 g) and a saturated aqueous sodium chloride solution (500 g). The water phase was discarded. To the organic phase was added a 1:1 mixture of tetrahydrofuran and water (900 g total). The reaction mixture was cooled to 0° C., followed by addition of triethylamine (135.5 g). isobutyl chloroformate (182 g), added at a rate such that the temperature did not exceed 10° C. After completion of the reaction, the mixture was allowed to heat to ambient temperature. The aqueous phase was discarded. To the organic phase were added water (200 g) and a saturated aqueous sodium chloride solution (300 g). The aqueous phase was discarded, the organic phase was cooled to 10° C. and to this mixture was added methanol (450 g). After stirring at 0° C., the product was filtered and dried under reduced pressure. The title compound was obtained as colorless crystalline solid.

M.P.: 160–163° C.
MS: m/z=391 (M+1)$^+$

EXAMPLE 15

(2S, 4R)-1-Acetyl-N-[(1S)-1-(2-benzothiazolylcarbonyl)-4-[[imino[(benzyloxycarbonyl)-amino]methyl]amino]butyl]-4-hydroxypyrrolidine-2-carboxamide

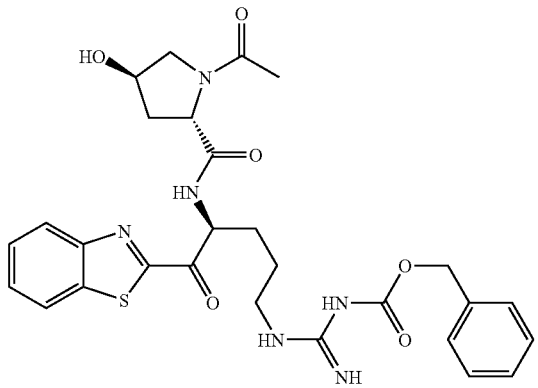

To a solution of tert-butylmagnesium chloride (200 g) in tetrahydrofuran (1.6 M) was added benzothiazole (17.4 g) dropwise. The mixture was stirred for 40 min. A suspension of [(3S)-1-(benzyloxycarbonylamino-imino-methyl)-2-oxo-piperidin-3-yl]-carbamic acid tert-butyl ester (20 g) in tetrahydrofuran (60 g) was added at –10° C. over 15 min. After 2 hours at –10° C. the reaction mixture was added to a mixture of ice (160 g), concentrated hydrochloric acid (77 g) and ethyl acetate (120 g). The organic layer was washed twice with a 1:1 mixture of concentrated aqueous sodium chloride solution and 2 M hydrochloric acid. Subsequently the organic phase was treated with hydrogen chloride gas and a 3.5 M solution of hydrogen chloride in 1,4-dioxane. The mixture was stirred at ambient temperature overnight. After completion of the reaction, the mixture was evaporated in vacuum. The residue was suspended in acetonitrile (50 g).

A mixture of N-acetyl-trans-4-hydroxy-L-proline (10.16 g), N-methylmorpholine (5.93 g) and acetonitrile (110 g) was cooled to –20° C. Over 5 min isobutylchloroformate (8.15 g) was added and the reaction mixture was stirred for 30 min at –20° C. To this mixture were added the compound prepared in Step A above in the prepared acetonitrile suspension and, simultaneously, N-methylmorpholine (10 g) at –20° C. After stirring at –15° C. for 30 min the reaction mixture was quenched with 2 M hydrochloric acid (200 g). The organic solvents were evaporated and the aqueous residue was treated with methanol (100 g). After stirring for 30 min the product was filtered and dried in vacuum at 40° C. The title compound was obtained as a colorless crystalline solid.

M.P.: 197° C.
MS: m/z=581 (M+1)$^+$

EXAMPLE 16

(2S, 4R)-1-Acetyl-N-[(1S)-1-(2-benzothiazolylcarbonyl)-4-[[imino(amino)methyl]-amino]butyl]-4-hydroxypyrrolidine-2-carboxamide

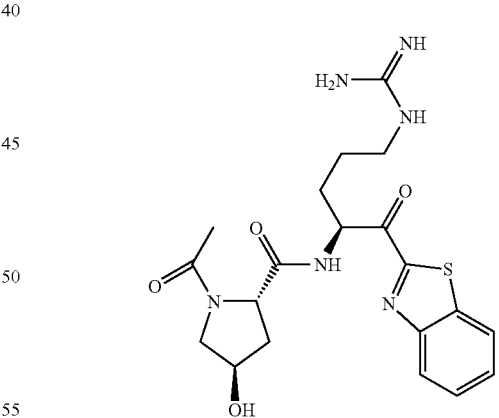

The title compound was obtained by stirring a solution of (2S, 4R)-1-acetyl-N-[(1S)-1-(2-benzothiazolylcarbonyl)-4-[[imino[(benzyloxycarbonyl)-amino]methyl]amino]butyl]-4-hydroxypyrrolidine-2-carboxamide (66 g) in concentrated hydrobromic acid (62% of HBr in water, 33 g) at ambient temperature for 6 h. The solution was then added to IPA (3237 g) at ambient temperature and then sulfuric acid (50 g) was added dropwise at ambient temperature. The title compound aws crystallized as a colorless solid over a period of 2 days at ambient temperature.

MS: m/z=447 (M+1)$^+$

EXAMPLE 17

(2S,4R)-1-Acetyl-N-[(1S)-4-[(aminoiminomethyl)amino]-1-(2-benzothiazolylcarbonyl)butyl]-4-hydroxy-2-pyrrolidinecarboxamide Nitrate Salt

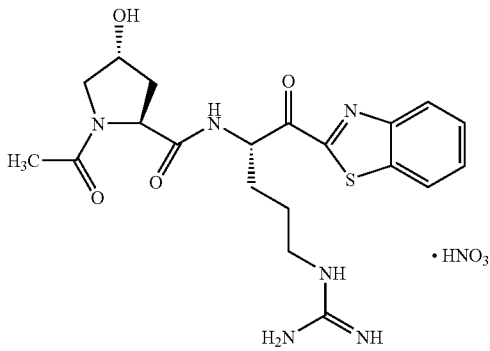

(2S,4R)-1-Acetyl-N-[(1S)-4-[(aminoiminomethyl)amino]-1-(2-benzothiazolylcarbonyl)butyl]-4-hydroxy-2-pyrrolidinecarboxamide as a free base in a diastereomeric ratio of 40:60 (591 mg, 1.27 mmol) was dissolved into a mixture of acetonitrile (6 mL) and ethanol (8 mL). To the mixture was added a solution of nitric acid (113 mg, 1.27 mmol) in acetonitrile (2 mL). Additional acetonitrile was then added until the cloud point. To the mixture were then added seeds of the desired nitrate salt. (The seeds were prepared by reacting chromatographed single diastereomer of the corresponding TFA salt with nitric acid, as described in Example 10). The mixture was then stirred for 18 hours at ambient temperature. The solid was filtered, washed with acetonitrile and dried in a vacuum oven to yield the title compound as an off-white solid.

Diastereomeric ratio: 21:79

EXAMPLE 18

(4S)-N-(4-Amino-5-benzothiazolyl-5-oxo-pentyl)-guanidine

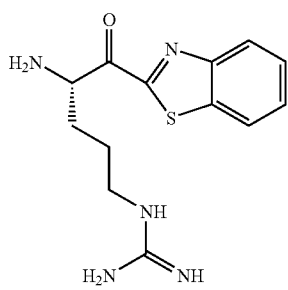

[4-([Amino-(4-methoxy-2,3,6-trimethyl-benzenesulfonylimino)-methyl]-amino}-1-(benzothiazole-2-carbon yl)-butyl]-carbamic acid tert-butyl ester (0.500 g, 0.0083 mole) was added to a solution (10 mL) of 0.3M CH$_3$SO$_3$H in a mixture of TFA/thioanisole (9:1) in an ice-bath. The reaction mixture was stirred at 0° C. for 50 min and then warmed to ambient temperature. To the reaction mixture was then added an additional amount of the 9:1 solution of 0.3M MeSO$_3$H in TFA/thioanisole (5 mL) at room temperature. The reaction mixture was then stirred at room temperature. At 4.5 hours an additional amount of the 9:1 solution of 0.3M MeSO$_3$H in TFA/thioanisole (5 mL) was added to the reaction mixture at room temperature and the reaction mixture then stirred at room temperature.

After a total of 5.2 hours, to the reaction mixture was added MTBE (50 mL) which resulted in the precipitation of a yellow solid. The solvent was decanted. To the residue was again added MTBE (50 mL) and the solvent decanted. This was repeated for a total of 5 additions of MTBE.

The title product as a yellow solid was collected and stored under vacuum in a desiccator.

Loop LC-MS(ES+): 292.2(100%, MH$^+$), 233.17(40%), 157.25(80%).

EXAMPLE 19

(4S)-N-(4-Amino-5-benzothiazolyl-5-oxo-pentyl)-guanidine

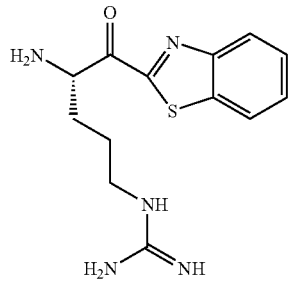

[4-{[Amino-(4-methoxy-2,3,6-trimethyl-benzenesulfonylimino)-methyl]-amino}-1-(benzothiazole-2-carbonyl)-butyl]-carbamic acid tert-butyl ester (0.200 g, 0.33 moles) was added to a solution (4 mL) of 0.3M TsOH.H$_2$O in a mixture of TFA/thioanisole (9:1) at 0° C. to yield a red-orange solution, which was then warmed to room temperature for 3 hours.

To the reaction mixture was slowly added MTBE (30 mL) which resulted in the precipitation of a light yellow solid. The solvent was decanted. To the residue was again added MTBE (25 mL) and the solvent decanted. This was repeated a second time with an additional amount of MTBE (25 mL).

The title product as a yellow solid was collected, dried in a vacuum dessicator. The product was used in the next step without further purification.

EXAMPLE 20

(2S,4R)-1-Acetyl-N-[(1S)-1-(2-benzothiazolylcarbonyl)-4-[[imino(amino)methyl]-amino]butyl]-4-hydroxypyrrolidine-2-carboxamide

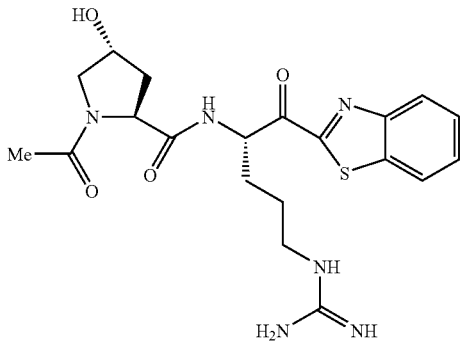

N-(4-Amino-5-benzothiazol-2-yl-5-oxo-pentyl)-guanidine (1.06 g, 3.6 mmol) was dissolved in THF (20 mL) and water (5 mL). To the reaction mixture was added hydroxylacetyl proline (0.63 g, 3.6 mmol) to yield a pH 1.2 solution, which was cooled to 0° C. To the reaction mixture was then added 4% of NaHCO$_3$ (3.5 mL) to adjust the solution pH to 6. To the reaction mixture was then added 1-ethyl-dimethylaminopropyl)carbodiimide hydrochloride (0.84 g, 4.4 mmol) and the reaction maintained at 0° C. for 1 hr. During this time, the pH of the solution was observed to increase. To maintain the pH at about 6, one or two drops of 1N TsOH were added as necessary. The reaction mixture was stirred at ambient temperature for an additional 3.5 hours.

The crude reaction mixture was purified by reverse phase chromatography (Kromasil C18 eluted with the gradient of 5 to 22% in 30 min of acetonitrile in a mixture of acetonitrile and water with 0.1% TFA) to yield the TFA salt of 1-acetyl-4-hydroxy-pyrrolidine-2-carboxylic acid [1-(benzothiazole-2-carbonyl)-4-guanidino-butyl]-amide.

$^1$H NMR (CD$_3$OD) δ 1.85 (2H), 1.85 (1H), 2.04 (1H), 2.08 (3H), 2.23 (1H), 2.24 (1H), 3.29 (2H), 3.55 (1H), 3.75 (1H), 4.46 (1H), 4.57 (1H), 5.74 (1H), 7.61 (1H) 7.64 (1H), 8.10 (1H), 8.20 (1H)

$^{13}$C NMR (CD$_3$OD): δ 22.38, 26.21, 29.89, 39.31, 41.89, 55.82, 57.47, 60.04, 70.87, 123.70, 126.35, 128.46, 129.29, 138.28, 154.64, 158.49, 165.36, 172.21, 174.66, 193.38.

EXAMPLE 21

(2S, 4R)-1-Acetyl-N-[(1S)-1-(2-benzothiazolylcarbonyl)-4-[[imino(amino)methyl]-amino]butyl]-4-hydroxypyrrolidine-2-carboxamide

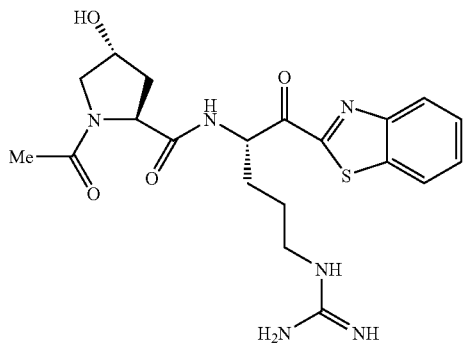

A solid mixture of N-(4-amino-5-benzothiazol-2-yl-5-oxo-pentyl)-guanidine (0.24 g, 0.83 mmol) and 1-acetyl-4-hydroxy-pyrrolidine-2-carboxylic acid (0.14 g, 0.83 mmol) was dissolved in THF (10 mL) and water (2 mL). To the reaction mixture was then added N,N'-diisopropyl carbodiimide to yield a reaction mixture of pH 1.8 at 0° C. The pH of the reaction mixture was adjusted to about 5.5 with 8% NaHCO$_3$. The reaction mixture was stirred at ambient temperature for 4 hours. The title compound was detected by HPLC (180 mg) and assayed by weight analysis.

EXAMPLE 22

{1-[Imino-(4-methoxy-2,3,6-trimethyl-benzenesulfonylamino)-methyl]-2-oxo-piperidin-3-yl}-carbamic Acid tert-butyl Ester

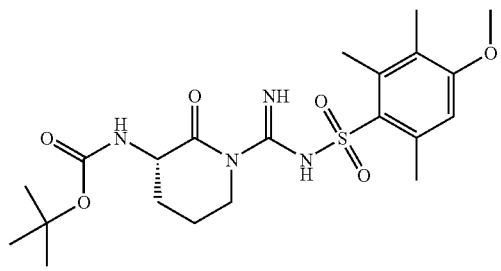

To a solution of Boc-Arg(Mtr)-OH (0.973 g, 2 mmol) and triethylamine (2.02 g, 20 mmol) in CH$_2$Cl$_2$ was added SOCl$_2$ (2.38 g, 20 mmol) at 0° C. The resulting dark brown slurry was stirred at room temperature for 2 hours. The reaction mixture was sampled into methanol and analyzed by HPLC and MS analysis. The major product was identified as the title compound.

EXAMPLE 23

{1-[Imino-(4-methoxy-2,3,6-trimethyl-benzenesulfonylamino)-methyl]-2-oxo-piperidin-3-yl}-carbamic Acid tert-butyl Ester

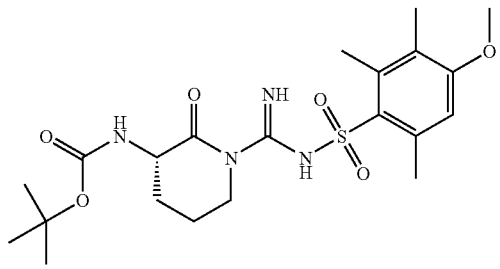

To a solution of Boc-Arg(Mtr)-OH (6.81 g, 14 mmol) and pyridine (1.11 g, 14 mmol) in CH$_2$Cl$_2$ (50 mL) at −20° C. was added cyanuric fluoride (9.45 g, 70 mmol). After addition, the reaction mixture was stirred at −10° C. for 1.5 hours. The reaction mixture was quenched with an ice-H$_2$O mixture and CH$_2$Cl$_2$ (50 mL), the resulting suspension was filtered through a pad of Celite and the two clear layers were separated. The aqueous layer was extracted with CH$_2$Cl$_2$ (50 mL)). The combined organic layer was washed with H$_2$O (50 mL), and dried over MgSO$_4$. After filtration and concentration, the crude oil was dissolved in CH$_2$Cl$_2$ and triturated in hexane. The title product was obtained as a white solid by vacuum filtration.

MS (ESI) m/z=469.2 (MH)$^+$

EXAMPLE 24

(2S, 4R)-1-Acetyl-N-[(1S)-1-(2-benzothiazolylcarbonyl)-4-[[imino(amino)methyl]-amino]butyl]-4-hydroxypyrrolidine-2-carboxamide Sulfate Salt

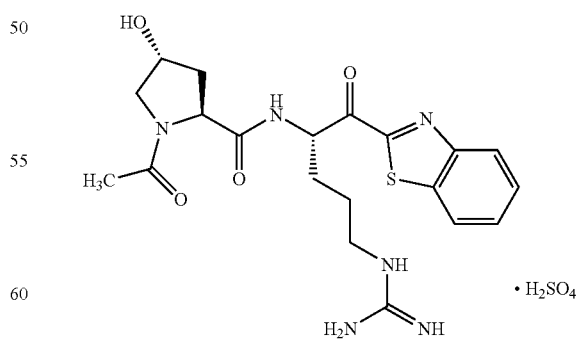

Crude (2S,4R)-1-acetyl-N-[(1S)-1-(2-benzothiazolylcarbonyl)-4-[[imino(amino)methyl]-amino]butyl]-4-hydroxypyrrolidine-2-carboxamide (430 g) was suspended in isopropanol (1050 mL) and heated to reflux. Distilled water (900 mL) was added in portions until all the solid was observed to dissolve in the solution. A solution of IPA:water (88:12, 300 mL) was then added. The solution was concentrated by distilling off the solvents. The addition of the IPA:water solution and concentration were repeated four times (The total volume of solvents distilled off was 1400 mL). After the fourth distillation, the remaining solution was stirred under $N_2$ and heated to 75° C. IPA (2450 mL) was then added to the solution slowly, over about one hour, while maintaining the temperature of the solution at greater than 60° C. The resulting amber colored solution was stirred, seeded and allowed to cool to room temperature. The mixture was then stirred for an additional 24 hours at room temperature. The resulting pale yellow solid was collected by filtration, then washed once with IPA. The solid was air dried for 2 hours, then dried in a vacuum oven at 60° C. for 16 hours, to yield the title compound as a pale yellow solid.

m.p.: 218–219° C.

| Calc: | C, 44.04%, H, 5.19%, N, 15.41%, S, 11.76% |
| --- | --- |
| | KF = 0.16% |
| Meas: | C, 44.08%, H, 5.15%, N, 15.39%, S, 11.77% |
| | KF = 0.28% |

ESI/MS: m/z 344.2, 447.2 [M+H]$^+$, 479.2 (MH+ CH$_3$OH)$^+$ $^1$H NMR of major rotomer (DMSO-d$_6$): δ 1.65 (2H), 1.76 (1H), 1.84 (1H), 1.94 (3H), 1.97 (1H), 1.99 (1H), 3.17 (1H), 3.34 (1H), 3.60 (1H), 4.30 (1H), 4.42 (1H), 5.10 (1H), 5.44 (1H), 6.86 abd 7.25 (4H), 7.44 (1H), 7.66 (1H), 7.69 (1H), 8.25 (1H), 8.27 (1H), 8.62 (1H)

EXAMPLE 25

(2S,4R)-1-Acetyl-N-[(1S) 4-[(aminoiminomethyl) amino]-1-(2-benzothiazolylcarbonyl)-butyl]-4-hydroxy-2-pyrrolidinecarboxamide

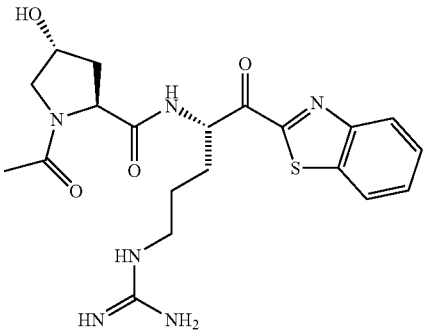

Acetyl chloride (3.3 mL, 46 mmol) was added dropwise to a solution of O-benzyl-L-4-trans-hydroxyproline methyl ester hydrochloride (12.5 g, 46 mmol), triethylamine (6.4 mL, 46 mmol) in pyridine (150 mL) at 0° C. while stirring under argon (Scheme 1). The reaction mixture was stirred for 30 min at 0° C. then slowly warmed to room temperature over 16 h. The reaction mixture was concentrated in vacuo, diluted with CH$_2$Cl$_2$, washed with 1 N HCl (3×), 10% aqueous Na$_2$CO$_3$, saturated aqueous NaHCO$_3$, brine, dried (MgSO$_4$) and concentrated in vacuo. The residue was purified by chromatography on silica gel (CH$_2$Cl$_2$/MeOH, 49:1) to give 7.12 g (55%) of Ac-Hyp(OBzl)-OMe as an oil. This oil (5.38 g, 19.4 mmol) was dissolved in tetrahydrofuran (260 mL), cooled to 0° C., treated dropwise with 0.15 M LiOH (260 mL, 39 mmol), and stirred for 30 min. The reaction mixture was concentrated in vacuo, acidified with 1 N HCl, and extracted three times with ethyl acetate. The combined organic extracts were dried (Na$_2$SO$_4$) and concentrated in vacuo to give 3.79 g (73%) of trans-1-acetyl-4-benzyloxy-L-proline as a white solid.

N-[[[(4S)-4-amino-5-(2-benzothiazolyl)-5-hydroxypentyl]amino]iminomethyl]-4-methyl-benzenesulfonamide (12.12 g, 0.027 mol), trans-1-acetyl-4-benzyloxy-L-proline (7.13 g, 0.027 mol), and 1-hydroxybenzotriazole hydrate (HOBT; 9.16 g, 0.068 mol) were combined in N,N-dimethylformamide (DMF, 270 mL), then treated with 1,3-dicyclohexylcarbodiimide (DCC; 13.99 g, 0.068 mol). The reaction was stirred under argon at room temperature for 18 h and filtered. The filtrate was diluted with water (ca. 800 mL), extracted with ethyl acetate (3×), washed with water, dried (Na$_2$SO$_4$) and concentrated in vacuo. The residue was purified by chromatography on silica gel (CH$_2$Cl$_2$/MeOH, 19:1) to yield, (2S,4R)-1-acetyl-N-[(1S)-1-(2-benzothiazolylhydroxymethyl)-4-[[imino[[(4-methylphenyl)sulfonyl]amino]methyl]amino]butyl]-4-(phenylmethoxy)-2-pyrrolidinecarboxamide as a white solid.

Dess-Martin reagent (also known as Dess-Martin periodinane) (18.7 g, 0.044 mol) was added to a solution of (2S,4R)-1-acetyl-N-[(1S)-1-(2-benzothiazolylhydroxymethyl)-4-[[imino[[(4-methylphenyl)sulfonyl]amino]methyl]amino]butyl]-4-(phenylmethoxy)-2-pyrrolidinecarboxamide (14.9 g, 0.022 mol) in CH$_2$Cl$_2$ (220 mL) under argon at room temperature and stirred for 1 h. The reaction mixture was quenched with a solution containing 20% Na$_2$S$_2$O$_3$ (w/w) in saturated aqueous NaHCO$_3$ and the mixture was allowed to epimerize by stirring at 23° C. for 2 h. The organic layer was separated, washed with brine, dried (Na$_2$SO$_4$) and concentrated in vacuo to furnish a white solid. This solid was dissolved in anhydrous anisole (ca. 12 mL) in a Teflon reaction vessel, placed on a HF apparatus, and cooled to −78° C. Anhydrous HF (ca. 38 mL) was condensed into the reaction vessel and the reaction was warmed to 0° C. The reaction was stirred at 0° C. for 6 h, concentrated in vacuo, and triturated with ethyl ether (3×) to furnish a white solid. This solid was purified by reverse-phase HPLC eluting with a gradient of water/acetonitrile/trifluoroacetic acid (90:10:0.2 to 70:30:0.2) on six PrepPak cartridges connected in series (Bondapak C-18; 40×300 mm; 15–20 µm, 125 Å) eluting at 40 mL/min over 60 min. The fractions containing both diastereomers of (2S,4R)-1-Acetyl-N-[4-[(aminoiminomethyl)amino]-1-(2-benzothiazolylcarbonyl)-butyl]-4-hydroxy-2-pyrrolidinecarboxamide were combined and lyophilized to yield a mixture of the diastereomers of (2S,4R)-1-acetyl-N-[(1S)-4-[(aminoiminomethyl)amino]-1-(2-benzothiazolylcarbonyl)-butyl]-4-hydroxy-2-pyrrolidinecarboxamide (diastereomeric ratio 1S/1R=1.1:1) as the trifluoroacetate (TFA) salt, which was converted to the HCl salt by dissolving the TFA salt into 0.1 N HCl and concentrating in vacuo three times in succession. The resulting glass was dissolved in water and lyophilized twice to yield the HCl salt of the title compound as a light yellow solid with 95% purity by HPLC and an L/D-arginine epimeric ratio of 1.2:1 by HPLC.

$^1$H NMR δ 1.50–2.40 (ov m, 9H), 3.10–3.90 (ov m, 3H), 4.22–4.90 (ov m, 3H), 5.52–5.63 (m, 0.4H), 5.63–5.74 (m, 0.6H), 7.50–7.80 (m, 2H), 8.00–8.28 (m, 2H);

MS (ES) m/z 447 (MH)$^+$

EXAMPLE 26

(2S,4R)-1-Acetyl-N-[(1R)-4-[(aminoiminomethyl)amino]-1-(2-benzothiazolylcarbonyl)-butyl]-4-hydroxy-2-pyrrolidinecarboxamide Nitrate Salt

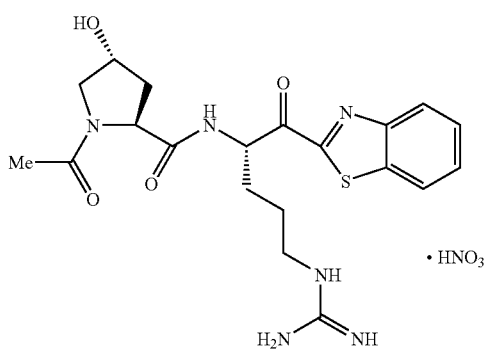

The process as described in Example 25 was repeated and the product was purified by reverse phase HPLC eluting with a gradient of water/MeCN/CF$_3$CO$_2$H (90:10:0.2 to 70:30:0.2) over 60 min. The fractions containing the earlier eluting diastereomers were combined and lyophilized to give the title compound as a TFA salt. This material (160 mg, 0.258 mmol) was dissolved into 3.8 mL of warm MeCN/MeOH (3.8:1) and treated with a solution of HNO$_3$ (23 mg, 0.258 mmol) in MeCN. The clear solution was concentrated under a stream of nitrogen to yield an oil, which was dissolved in water and lyophilized to yield the title compound as a white hygroscopic solid.

$^1$H NMR δ 1.60–2.00 (ov m, 4H), 2.08 (s, 3H), 2.10–2.30 (m, 2H), 3.45–3.60 (m, 1H), 3.74 (dd, 1H, J=4.4, 11.1 Hz), 4.35–4.40 (m, 1H), 4.53 (t, 1H, J=8.2 Hz) 5.59 (dd, 1H, J=3.7, 9.2 Hz), 7.55–7.70 (m, 2H), 8.08 (d, 1H, J=7.4 Hz), 8.18 (d, 1H, J=6.8);

MS (ES) m/z 447 (MH)$^+$

EXAMPLE 27

(2S,4R)-1-Acetyl-N-[(1S)-4-[(aminoiminomethyl)amino]-1-(2-benzothiazolylcarbonyl)-butyl]-4-hydroxy-2-pyrrolidinecarboxamide Nitrate Salt

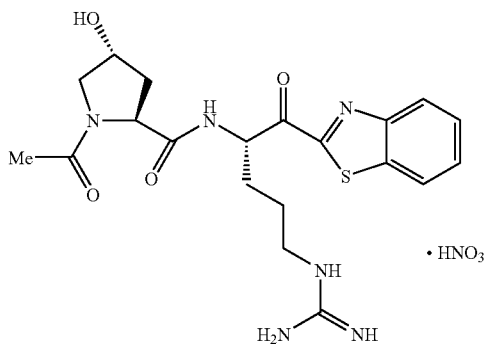

The process as described in Example 25 was repeated, except the Dess-Martin oxidation was processed immediately after quenching with 20% Na$_2$S$_2$O$_3$ (w/w) in saturated aqueous NaHCO$_3$ to minimize epimerization. The product was purified by reverse-phase HPLC (water/MeCN/CF$_3$CO$_2$H, 90:10:0.2 to 70:30:0.2) over 60 min and the fractions containing the slower-eluting diastereomers were combined and lyophilized to yield the title compound as a TFA salt. The purified salt (1.5 g, 2.42 mmol) was dissolved into warm MeCN with a small amount of MeOH and treated with a solution of HNO$_3$ (0.21 g, 2.42 mmol) in MeCN. The white crystalline solid that formed on cooling was washed with MeCN and dried in vacuo to yield the title compound.

mp 174.5–176.5° C.;

$^1$H NMR δ 1.50–2.08 (ov m, 4H), 2.10 (s, 3H), 2.12–2.30 (m, 2H), 3.54 (d, 1H, J=11.1 Hz), 3.76 (dd, 1H, J=4.1, 11.1 Hz), 4.40–4.49 (m, 1H), 4.57 (t, 1H, J=8.1 Hz) 5.70–5.82 (m, 1H), 7.55–7.70 (m, 2H), 8.08 (d, 1H, J=7.4 Hz), 8.18 (d, 1H, J=6.8);

MS (ES) m/z 447 (MH)$^+$

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A process for the preparation of a compound of formula (IIa)

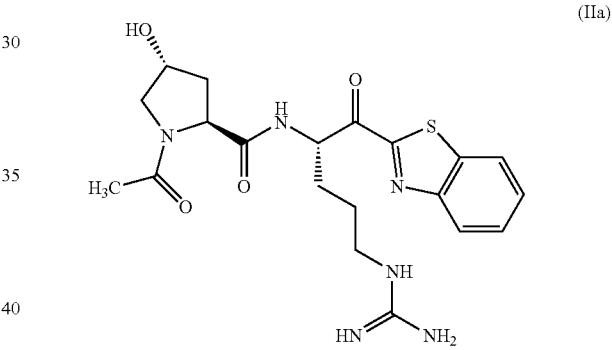

comprising

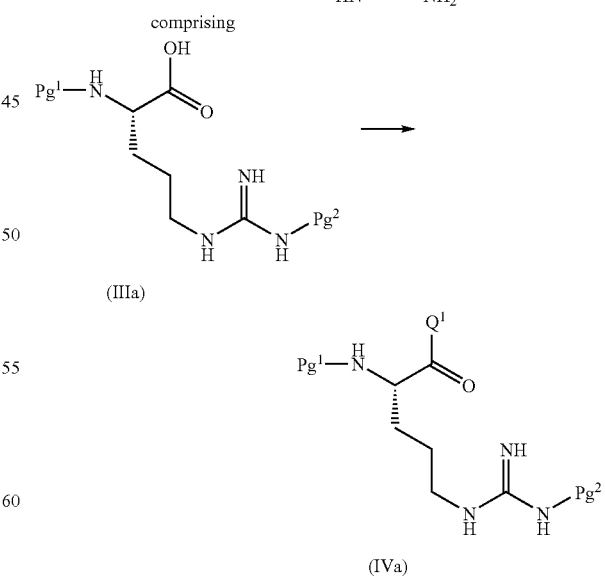

reacting a compound of formula (IIIa), wherein Pg$^1$ is a first nitrogen protecting group and Pg$^2$ is a second nitrogen protecting group; and wherein Pg$^1$ and Pg² are selected such that the Pg¹ protecting group may be removed under conditions which do not remove the Pg² protecting group; with a suitable activating agent;

to yield the corresponding compound of formula (IVa), wherein Q¹ is a leaving group;

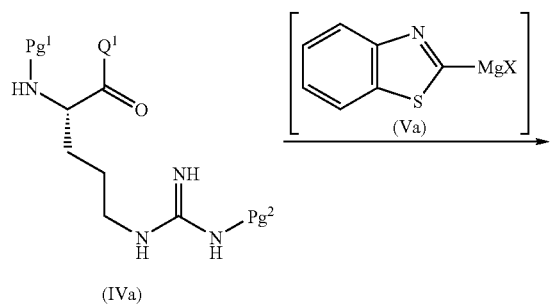

(IVa)

reacting the compound of formula (IVa) with a solution or suspension of a compound of formula (Va), wherein X is selected from the group consisting of Cl, Br and I; in an anhydrous organic solvent which is inert to the compound of formula (Va);

to yield the corresponding compound of formula (VIa);

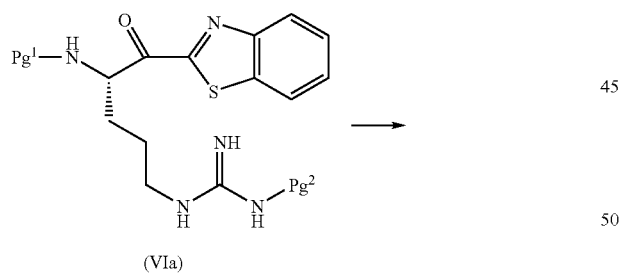

subjecting the compound of formula (VIa) to selective de-protection, to yield the corresponding compound of formula (VIIa) or its corresponding acid addition salt;

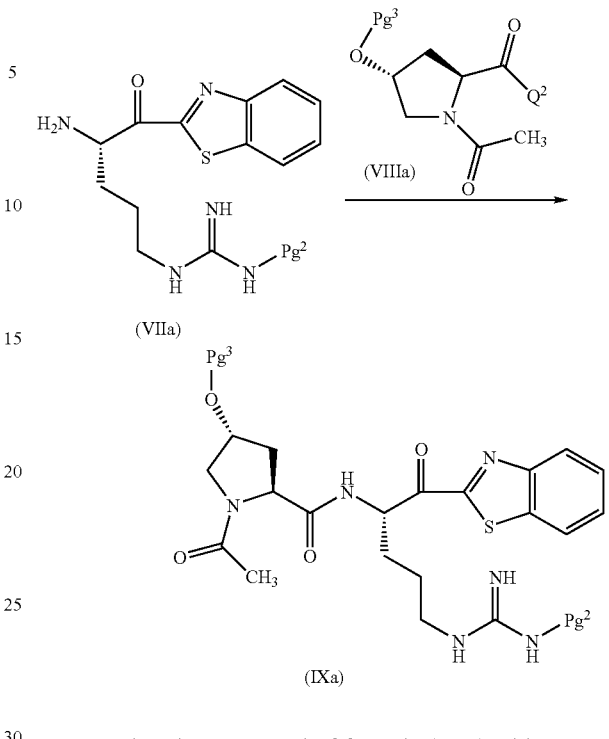

reacting the compound of formula (VIIa) with a compound of formula (VIIIa), wherein Pg³ is an oxygen protecting group; and wherein Q² is a leaving group; in the presence of a tertiary amine base; in an aprotic organic solvent;

to yield the corresponding compound of formula (IXa);

de-protecting the compound of formula (IXa), to yield the corresponding compound of formula (IIa).

2. A process for the preparation of a compound of formula (IIa)

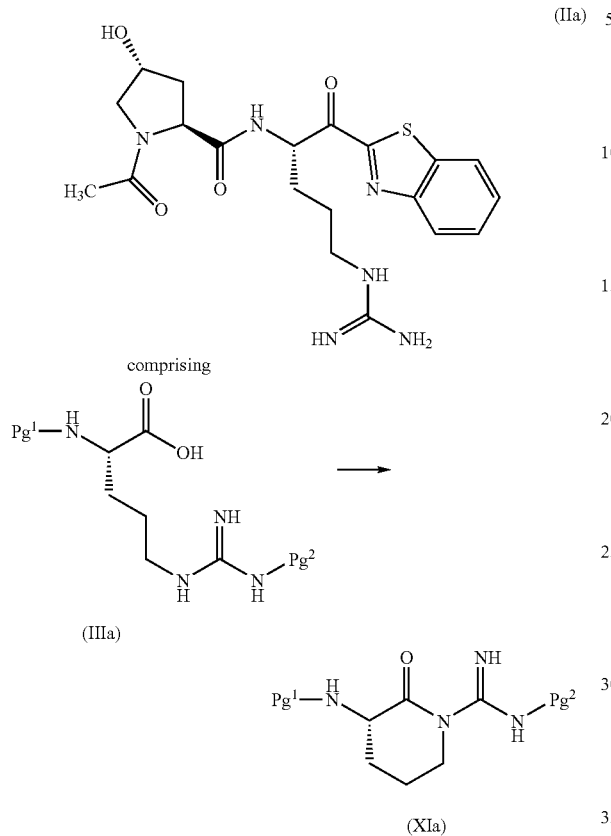

comprising

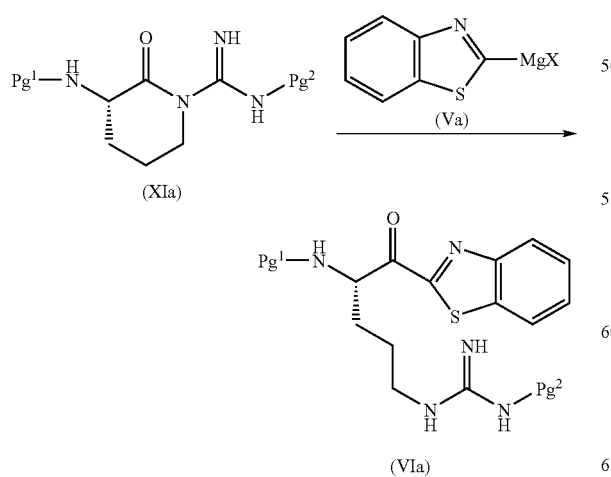

reacting a compound of formula (IIIa),
wherein Pg¹ is a first nitrogen protecting group and Pg² is a second nitrogen protecting group; and wherein Pg¹ and Pg² are selected such that the Pg¹ protecting group may be removed under conditions which do not remove the Pg² protecting group; with an activating agent capable of cyclizing the compound of formula (IIIa),
to yield the corresponding compound of formula (XIa);

reacting the compound of formula (XIa) with a solution or suspension of a suitably substituted compound of formula (Va),
wherein X is selected from the group consisting of Cl, Br and I; in an anhydrous organic solvent which is inert to the compound of formula (Va);
to yield the corresponding compound of formula (VIa);

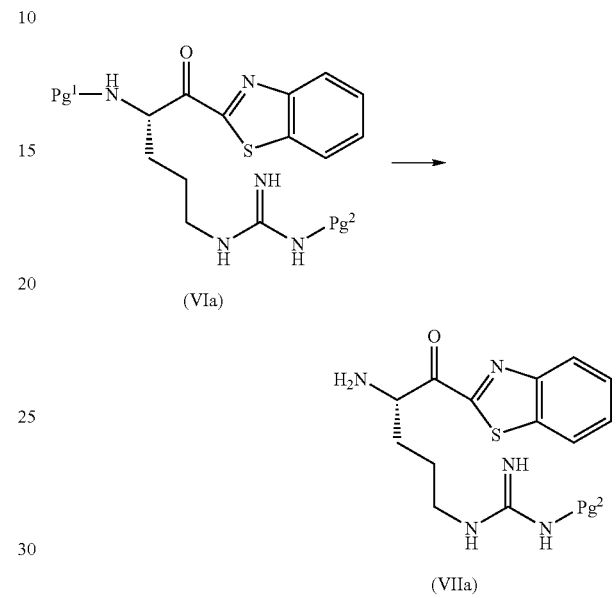

subjecting the compound of formula (VIa) to selective de-protection, to yield the corresponding compound of formula (VIIa) or its corresponding acid addition salt;

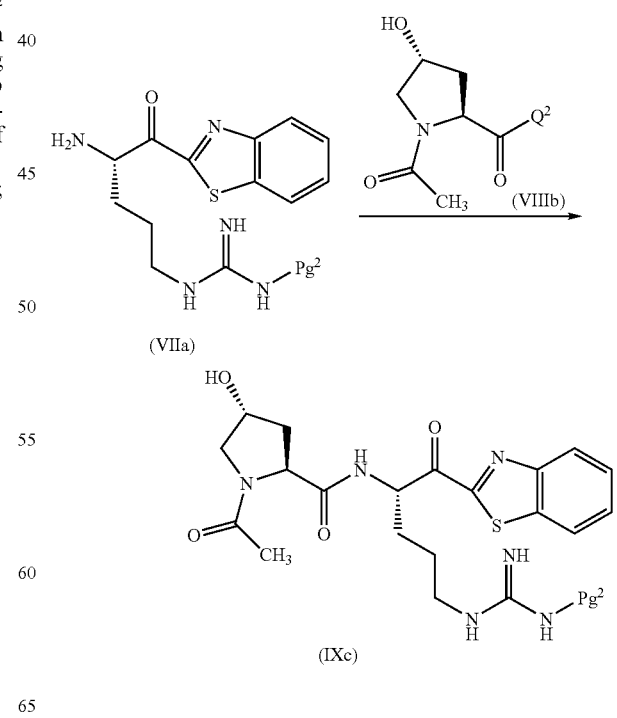

reacting the compound of formula (VIIa) with a compound of formula (VIIIb), wherein $Q^2$ is a leaving group; in the presence of a tertiary amine base; in an aprotic organic solvent; to yield the corresponding compound of formula (IXc);
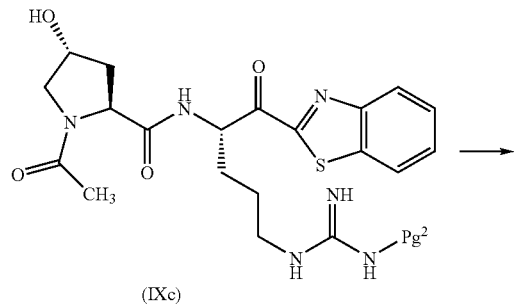
(IXc)
-continued
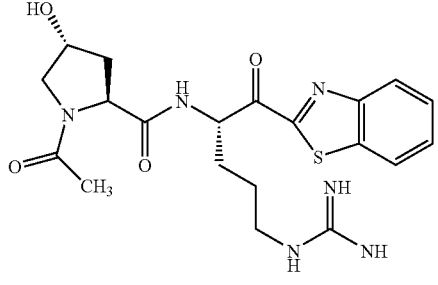
(IIa)
subjecting the compound of formula (IXe) to de-protection, to yield the corresponding compound of formula (IIa).
* * * * *